US011191768B2

(12) United States Patent
Arancio et al.

(10) Patent No.: US 11,191,768 B2
(45) Date of Patent: Dec. 7, 2021

(54) HISTONE ACETYLTRANSFERASE ACTIVATORS AND USES THEREOF

(71) Applicant: The Trustees of Columbia University in the City of New York, New York, NY (US)

(72) Inventors: Ottavio Arancio, New York, NY (US); Shixian Deng, White Plains, NY (US); Donald W. Landry, New York, NY (US); Jole Fiorito, Floral Park, NY (US); Rosa Purgatorio, Bari (IT); Owen Anthony O'Connor, Scarsdale, NY (US); Jennifer Effie Amengual, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/700,693

(22) Filed: Dec. 2, 2019

(65) Prior Publication Data

US 2020/0101078 A1    Apr. 2, 2020

Related U.S. Application Data

(63) Continuation of application No. 15/868,458, filed on Jan. 11, 2018, now abandoned, which is a continuation of application No. 15/300,497, filed as application No. PCT/US2015/023258 on Mar. 30, 2015, now abandoned, which is a continuation of application No. 62/023,715, filed on Jul. 11, 2014.

(60) Provisional application No. 61/972,571, filed on Mar. 31, 2014.

(51) Int. Cl.
| | |
|---|---|
| *C07D 209/46* | (2006.01) |
| *A61K 31/536* | (2006.01) |
| *C07C 235/64* | (2006.01) |
| *C07C 235/42* | (2006.01) |
| *C07C 237/40* | (2006.01) |
| *C07D 265/22* | (2006.01) |
| *C07D 265/26* | (2006.01) |
| *C07D 209/34* | (2006.01) |
| *C07D 209/38* | (2006.01) |
| *A61K 31/166* | (2006.01) |
| *A61K 31/403* | (2006.01) |

(52) U.S. Cl.
CPC .......... *A61K 31/536* (2013.01); *A61K 31/166* (2013.01); *A61K 31/403* (2013.01); *C07C 235/42* (2013.01); *C07C 235/64* (2013.01); *C07C 237/40* (2013.01); *C07D 209/34* (2013.01); *C07D 209/38* (2013.01); *C07D 209/46* (2013.01); *C07D 265/22* (2013.01); *C07D 265/26* (2013.01); *A61K 2121/00* (2013.01)

(58) Field of Classification Search
CPC .. C07D 209/46; C07D 209/48; C07C 235/42; C07C 235/64
See application file for complete search history.

(56) References Cited

U.S. PATENT DOCUMENTS

| | | | |
|---|---|---|---|
| 3,449,420 A | * | 6/1969 | Duwel .................. C07C 233/12 564/179 |
| 6,492,425 B1 | | 12/2002 | Callahan et al. |
| 8,705,109 B2 | | 4/2014 | Aso |
| 9,266,872 B2 | | 2/2016 | Kim et al. |
| 9,969,677 B2 | | 5/2018 | Francis et al. |
| 2009/0076155 A1 | | 3/2009 | Kundu et al. |
| 2010/0144885 A1 | | 6/2010 | Pandey |
| 2010/0166781 A1 | | 7/2010 | Setiadi et al. |
| 2011/0166155 A1 | | 7/2011 | Van Wagenen et al. |
| 2013/0121919 A1 | | 5/2013 | Feng et al. |
| 2017/0121276 A1 | | 5/2017 | Francis et al. |
| 2018/0021273 A1 | | 1/2018 | O'Connor et al. |

FOREIGN PATENT DOCUMENTS

| | | |
|---|---|---|
| CN | 103347392 A | 10/2013 |
| EP | 2509590 A1 | 10/2012 |
| GB | 1124613 A | 8/1968 |
| JP | 2013-513618 A | 4/2013 |
| JP | 2014-501763 A | 1/2014 |
| WO | WO-2004/053140 A2 | 6/2004 |
| WO | WO-2004/089470 A2 | 10/2004 |
| WO | WO-2011/038572 A1 | 4/2011 |
| WO | WO-2011/072243 | 6/2011 |
| WO | WO-2012/081570 A1 | 6/2012 |
| WO | WO-2012/088420 | 6/2012 |
| WO | WO-2012/171008 A1 | 12/2012 |

(Continued)

OTHER PUBLICATIONS

Chemical Abstracts Registry No. 20788-13-0, indexed in the Registry file on STN CAS Online Nov. 16, 1984. (Year: 1984).*

(Continued)

*Primary Examiner* — Laura L Stockton

(74) *Attorney, Agent, or Firm* — Wilmer Cutler Pickering Hale and Dorr LLP

(57) ABSTRACT

The invention provides compounds and compositions comprising compounds that modulate histone acyl transferase (HAT). The invention further provides methods for treating neurodegenerative disorders, conditions associated with accumulated amyloid-beta peptide deposits, Tau protein levels, and/or accumulations of alpha-synuclein as well as cancer by administering a compound that modulates HAT to a subject.

4 Claims, 18 Drawing Sheets

(56) References Cited

FOREIGN PATENT DOCUMENTS

| WO | WO-2013/058613 A2 * | 4/2013 | ............ C07C 235/84 |
| WO | WO-2013/130807 A1 | 9/2013 | |

OTHER PUBLICATIONS

Alamed et al., "Two-day radial-arm water maze learning and memory task; robust resolution of amyloid-related memory deficits in transgenic mice," Nat. Protoc., 1(4), pp. 1671-1679 (2006).
Bailey and Chen, "Morphological basis of long-term habituation and sensitization in Aplysia," Science, 220(4592), pp. 91-93 (1983).
Balasubramanyam et al. "Small molecule modulators of histone acetyltransferase p300," J. Biol. Chem., 278(21): p. 19134-19140 (2003).
Berge et al., "Pharmaceutical salts," J. Pharm. Sci., 66(1): pp. 1-19 (1977).
Chen et al., "Impairment of hippocampal long-term potentiation by Alzheimer amyloid beta-peptides," J. Neurosci. Res., 60(1), pp. 65-72 (2000).
Cleary et al., "Natural oligomers of the amyloid-beta protein specifically disrupt cognitive function," Nat. Neurosci., 8(1), pp. 79-84 (2005).
Colton et al., "NO synthase 2 (NOS2) deletion promotes multiple pathologies in a mouse model of Alzheimer's disease," Proceedings of the National Academy of Sciences, 103, p. 12867-12872 (2006).
Cullen et al., "Block of LTP in rat hippocampus in vivo by beta-amyloid precursor protein fragments," Neuroreport, 8(15), pp. 3213-3217 (1997).
Dash et al., "Injection of the cAMP-responsive element into the nucleus of Aplysia sensory neurons blocks long-term facilitation," Nature, 345(6277), pp. 718-721 (1990).
Database Registry [Online], Chemical Abstracts Service, Columbus, Ohio, US, Benzamide, "-chloro-N-[4-chloro-3-(trifluoromethyl)phenyl]-6-fluoro-,"XP002772362, Database accession No. 1004056-14-7, 1 page (2008).
Database Registry [Online], Chemical Abstracts Service, Columbus, Ohio, US, "Benzamide, 2,6-dichloro-N-(3,4-dibromophenyl)-," XP002772365, Database accession No. 904622-09-9, 1 page (2006).
Database Registry [Online], Chemical Abstracts Service, Columbus, Ohio, US, "Benzamide, 2,6-dichloro-N-(3,4-dichlorophenyl)-," XP002772372, Database accession No. 348603-97-4, 1 page (2001).
Database Registry [Online], Chemical Abstracts Service, Columbus, Ohio, US, "Benzamide, 2,6-dichloro-N-(3,4-difluorophenyl)-," XP002772370, Database accession No. 405147-78-6, 1 page (2002).
Database Registry [Online], Chemical Abstracts Service, Columbus, Ohio, US, "Benzamide, 2,6-dichloro-N-(3-chloro-4-fluorophenyl)-," XP002772371, Database accession No. 405147-75-3, 1 page (2002).
Database Registry [Online], Chemical Abstracts Service, Columbus, Ohio, US, "Benzamide, 2,6-dichloro-N-[ 4-chloro-3-(trifluoromethyl)phenyl]-," XP002772369, Database accession No. 692290-31-6, 1 page (2004).
Database Registry [Online], Chemical Abstracts Service, Columbus, Ohio, US, "Benzamide, 2-chloro-6-fluoro-N-[4-fluoro-3-(trifluoromethyl)phenyl]-," XP002772359, Database accession No. 1370888-59-7, 1 page (2012).
Database Registry [Online], Chemical Abstracts Service, Columbus, Ohio, US, "Benzamide, 2-chloro-N-(3,4-dichlorophenyl)-6-fluoro-," XP002772361, Database accession No. 1037912-92-7, 1 page (2008).
Database Registry [Online], Chemical Abstracts Service, Columbus, Ohio, US, "Benzamide, 2-chloro-N-(3,4-difluorophenyl)-6-fluoro-," XP002772363, Database accession No. 1001971-32-9, 1 page (2008).
Database Registry [Online], Chemical Abstracts Service, Columbus, Ohio, US, "Benzamide, 2-chloro-N-(3-chloro-4-fluorophenyl)-6-fluoro-," XP002772360, Database accession No. 1038026-66-2, 1 page (2008).
Database Registry [Online], Chemical Abstracts Services, Columbus, Ohio, US, "Benzamide, N-(4-bromo-3-fl uorophenyl)-2-fluoro-6-methocy-" XP002772351, Database accession No. 1498238-78-0, 1 page (2013).
Database Registry [Online], Chemical Abstracts Service, Columbus, Ohio, US, "Benzamide, N-(-3-bromo-4-chlorophenyl)-2,6-dichloro-," XP002772352, Database accession No. 1537042-44-6, 1 page (2014).
Database Registry [Online], Chemical Abstracts Service, Columbus, Ohio, US, "Benzamide, N-(3,4-dichlorophenyl)-2,6-difluoro-," XP002772364, Database accession No. 937648-21-0, 1 page (2007).
Database Registry [Online], Chemical Abstracts Service, Columbus, Ohio, US, "Benzamide, N-(3,4-dichlorophenyl)-2-hydroxy-6-methoxy," XP002772349, Database accession No. 883802-63-9, 1 page (2006).
Database Registry [Online], Chemical Abstracts Service, Columbus, Ohio, US, "Benzamide, N-(3-bormo-4-chlorophenyl)-2-chloro-6-fluoro-," XP002772353, Database accession No. 15095454-88-3, 1 page (2014).
Database Registry [Online], Chemical Abstracts Service, Columbus, Ohio, US, "Benzamide, N-(3-bromo-4-chlorophenyl)-2-fluoro-6-methoxy-," XP002772350, Database accession No. 1500685-94-8, 1 page (2013).
Database Registry [Online], Chemical Abstracts Service, Columbus, Ohio, US, "Benzamide, N-(3-bromo-4-chlorophynel)-2,6-difluoro," XP002772354, Database accession No. 1499147-11-3, 1 page (2013).
Database Registry [Online], Chemical Abstracts Service, Columbus, Ohio, US, "Benzamide, N-(3-chloro-4-fluorophenyl)-2-fluoro-6-(trifluoromethyl)-," XP002772358, Database accession No. 1446248-89-0, 1 page (2013).
Database Registry [Online], Chemical Abstracts Service, Columbus, Ohio, US, "Benzamide, N-(4-bromo-3-chlorophenyl)-2,6-dichloro-," XP002772366, Database accession No. 881815-48-1, 1 page (2006).
Database Registry [Online], Chemical Abstracts Service, Columbus, Ohio, US, "Benzamide, N-(4-bromo-3-fluorophenyl)-2,6-dichloro-," XP002772355, Database accession No. 1487503-14-9, 1 page (2013).
Database Registry [Online], Chemical Abstracts Service, Columbus, Ohio, US, "Benzamide, N-(4-bromo-3-fluorophenyl)-2,6-difluoro-," XP002772357, Database accession No. 1483281-17-9, 1 page (2013).
Database Registry [Online], Chemical Abstracts Service, Columbus, Ohio, US, "Benzamide, N-(4-bromo-3-fluorophenyl)-2-chloro-6-fluoro-," XP002772356, Database accession No. 1485429-09-1, 1 page (2013).
Database Registry [Online], Chemical Abstracts Service, Columbus, Ohio, US, "Benzamide, N-[4-bromo-3-(trifluoromethyl)phenyl]-2,6-difluoro-," XP002772373, Database accession No. 288859-85-8, 1 page (2000).
Database Registry [Online], Chemical Abstracts Service, Columbus, Ohio, US, "Benzamide, N-[4-bromo-3-(trifluoromethyl)phenyl]-2-chloro-6-fluoro-," XP002772368, Database accession No. 753469-12-4, 1 page (2004).
Database Registry [Online], Chemical Abstracts Service, Columbus, Ohio, US, "Benzamide, N-[4-chloro-3-(trifluoromethyl)phenyl]-2,6-difluoro-," XP002772367, Database accession No. 877975-67-2, 1 page (2006).
Di Rosa et al., "Calpain inhibitors: a treatment for Alzheimer's disease," Mol. Neurosci., 19(1-2): pp. 135-141 (2002).
Duff et al., "Increased amyloid-beta42(43) in brains of mice expressing mutant presenilin 1," Nature, 383(6602), pp. 710-713 (1996).
Emborg, "Evaluation of animal models of Parkinson's disease for neuroprotective strategies," Journal of Neuroscience Methods, 139: pp. 121-143 (2004).
English Translation of Office Action issued in corresponding Chinese Application No. 201580027967.1, dated Jul. 3, 2018 (3 pages).

(56) References Cited

OTHER PUBLICATIONS

Fleming et al., "Early and progressive sensorimotor anomalies in mice overexpressing wild-type human alpha-synuclein," The Journal of Neuroscience, 24( 42): pp. 9434-9440 (2004).
Francis et al., "Dysregulation of histone acetylation in the APP/PS1 mouse model of Alzheimer's disease," d. Alzheimers Dis., 18(1): pp. 131-139 (2009).
Gong et al., "Persistent improvement in synaptic and cognitive functions in an Alzheimer mouse model after rolipram treatment," J. Clin. Invest., 114, pp. 1624-1634 (2004).
Gong et al., "Ubiquitin hydrolase Uch-L1 rescues beta-amyloid-induced decreases in synaptic function and contextual memory," Cell, 126(4): pp. 775-788 (2006).
Gould, "Salt selection for basic drugs," Int. J. Pharmaceutics, 33: pp. 201-217 (1986).
Guan et al., "HDAC2 negatively regulates memory formation and synaptic plasticity," Nature, 459, pp. 55-60 (2009).
Guo et al., "Epigenetic mechanisms of amyloid-β production in anisomycin-treated SH-SY5Y cells," Neuroscience, 194, pp. 272-281 (2011).
Hodgson et al., "A YAC mouse model for Huntington's disease with full-length mutant huntingtin, cytoplasmic toxicity, and selective striatal neurodegeneration," Neuron, 23: pp. 181-192 (1999).
Hsiao et al., "Correlative memory deficits, Aβ elevation, and amyloid plaques in transgenic mice," Science, 274(5284), pp. 99-102 (1996).
Hwang et al., "3,4-dihydroxyphenylalanine reverses the motor deficits in Pitx3-deficient aphakia mice: behavioral characterization of a novel genetic model of Parkinson's disease," The Journal of Neuroscience, 25(8): pp. 2132-2137 (2005).
International Search Report and Written Opinion for International Application No. PCT/US15/23258 dated Oct. 8, 2015 (10 pages).
Itoh et al., "Impairments of long-term potentiation in hippocampal slices of beta-amyloid-infused rats," Eur. J. Pharmacol., 382(3): pp. 167-175 (1999).
Kandel, "The molecular biology of memory storage: a dialog between genes and synapses," Biosci. Rep., 21(5): pp. 565-611 (2001).
Lambert et al., "Diffusible, nonfibrillar ligands derived from Abeta1-42 are potent central nervous system neurotoxins," Proc. Natl. Acad. Sci. USA, 95(11), pp. 6448-6453 (1998).
Lane, "Animal models of Parkinson's disease and L-dopa induced dyskinesia: how close are we to the clinic?" Psychopharmacology, 199, pp. 303-312 (2008).
Langley et al., "Remodeling chromatin and stress resistance in the central nervous system: histone deacetylase inhibitors as novel and broadly effective neuroprotective agents," Curr. Drug Targets CNS Neurol. Disord., 4(1): pp. 41-50 (2005).
Levenson and Sweatt "Epigenetic mechanisms in memory formation," Nat. Rev. Neurosci., 6(2), pp. 108-118 (2005).
Malm et al., "beta-Amyloid infusion results in delayed and age-dependent learning deficits without role of inflammation or beta-amyloid deposits," Proc. Natl. Acad. Sci. USA, 103(23), pp. 8852-8857 (2006).
Mantelingu et al., "Activation of p300 histone acetyltransferase by small molecules altering enzyme structure: probed by surface-enhanced Raman spectroscopy," J. Phys. Chem. B, 111(17), pp. 4527-4534 (2007).
Masliah "Mechanisms of synaptic dysfunction in Alzheimer's disease," Histol. Histopathol., 10(2): pp. 509-519 (1995).
Meredith et al., "Animal models of Parkinson's disease progression," Acta Neuropathol., 115, pp. 385-398 (2008).
Montarolo et al., "A critical period for macromolecular synthesis in long-term heterosynaptic facilitation in Aplysia," Science, 234(4781), pp. 1249-1254 (1986).
Peterson, "Histones and histone modifications," Curr. Biol., 14(14): pp. R546-551 (2004).
Piaz et al., "The identification of a novel natural activator of p300 histone acetyltranferase provides new insights into the modulation mechanism of this enzyme," Chembiochem., 11: pp. 818-827 (2010).
Pittenger and Kandel, "In search of general mechanisms for long-lasting plasticity: Aplysia and the hippocampus," Philos. Trans. R. Soc. Land. B. Biol. Sci., 358(1432), pp. 757-763 (2003).
Puzzo et al., "Amyloid-beta peptide inhibits activation of the nitric oxide/cGMP/cAMP-responsive element-binding protein pathway during hippocampal synaptic plasticity," Neurosci., 25: pp. 6887-6897 (2005).
Puzzo et al., "Picomolar amyloid-beta positively modulates synaptic plasticity and memory in hippocampus," J. Neurosci., 28(53), p. 14537-14545 (2008).
Rakyan et al., "The marks, mechanisms and memory of epigenetic states in mammals," Biochem. J., 356(Pt 1): pp. 1-10 (2001).
Selkoe, "Alzheimer's disease is a synaptic failure," Science, 298, pp. 789-791 (2002).
Selvi et al., "Tuning acetylation levels with HAT activators: therapeutic strategy in neurodegenerative diseases," Biochim. Biophys. Acta., vol. 1799, Issue 10-12, pp. 840-853 (2010).
Silverman "The Organic Chemistry of Drug Design," Elsevier Academic Press, (Second Edition), pp. 27-33, 19 pages total (2008).
Sipos et al., "Beta-amyloid pathology in the entorhinal cortex of rats induces memory deficits: implications for Alzheimer's disease," Neuroscience, 147(1), pp. 28-36 (2007).
STN-Registry, ACS, "RN 1537042-44-6, 1509545-88-3, 1500685-94-8, 1499147-11-3, 1498238-78-0, 1487503-14-9, 1446248-89-0, 1370888-59-7, 348603-97-4, 288859-85-8," 18 pages (Feb. 4, 2014 to Sep. 13, 2000).
Sweatt, "Neuroscience. Epigenetics and cognitive aging," Science, 328(5979), pp. 701-702 (2010).
Trinchese et al., "Progressive age-related development of Alzheimer-like pathology in APP/PS1 mice," Ann. Neural., 55(6): pp. 801-814 (2004).
Vitolo et al., "Amyloid beta-peptide inhibition of the PKA/CREB pathway and long-term potentiation: reversibility by drugs that enhance cAMP signaling," Proc. Natl. Acad. Sci. USA, 99(20), p. 13217-13221 (2002).
Walsh et al., "Naturally secreted oligomers of amyloid beta protein potently inhibit hippocampal long-term potentiation in vivo," Nature, 416(6880), pp. 535-539 (2002).
Xu et al., "Targeting HDACs: A Promising Therapy for Alzheimer's Disease," Oxid. Med. Cell. Longev., vol. 2011, Article ID 143269, 5 pages (2011).

\* cited by examiner

HISTONE ACETYLTRANSFERASE ACTIVATORS AND USES THEREOF

This application is a continuation of U.S. patent application Ser. No. 15/868,458 filed on Jan. 11, 2018, entitled "Histone Acetyltransferase Activators and Uses Thereof," which is a continuation of U.S. patent application Ser. No. 15/300,497, filed Sep. 29, 2016, entitled "Histone Acetyltransferase Activators and Uses Thereof," which is a U.S. National Stage Entry of International Patent Application No. PCT/US2015/023258, filed Mar. 30, 2015, entitled "Histone Acetyltransferase Activators and Uses Thereof," which claims the benefit of and priority to U.S. Provisional Application No. 61/972,571, filed on Mar. 31, 2014 entitled "Histone Acetyltransferase Activators and Uses Thereof," and U.S. Provisional Application No. 62/023,715, filed on Jul. 11, 2014, entitled "Histone Acetyltransferase Activators and Uses Thereof," the entire content of each of these applications is incorporated herein by reference in its entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Modulation of the acetylation state of histones, transcription factors, and other regulatory proteins is known to influence their activity within cancer and inflammatory cells. The acetylation state of a protein is controlled by the activity of two main groups of enzymes, histone deacetylases (HDAC) and histone acetyl transferases (HAT). The HDAC removes acetyl-groups while the HATs transfer acetyl-groups to the protein of interest.

Classically, modulation of acctylation status is known to influence the condensation of chromatin. In cancer, histones are deacetylated maintaining a condensed chromatin structure, and a transcriptionally silenced state. This transcriptional inactivation is mediated by HDACs which remove acetyl groups from histone tails, maintain a condensed chromatic structure. Inhibitors of HDACs help maintain transcriptionally active chromatin, theoretically allowing for expression of tumor suppressor genes. One observation that has evolved is that histones are not the only targets of acetylation. It is now accepted that post-translational acetylation of intracellular proteins such as tumor suppressors (p53) and oncogenes (Bcl6) plays a critical role in influencing their activity. It has been established that there is a network of proteins and enzymes that can be modified by acetylation, now collectively referred to as the acetylome.

Cognitive neurodegenerative disorders are characterized by synaptic dysfunction, cognitive abnormalities, and/or the presence of inclusion bodies throughout the CNS containing, for example, but not limited to native beta-amyloid fragments, native and phosphorylated Tau, native and phosphorylated alpha-synuclein, lipofuscin, cleaved TARDBP (TDB-43), in various percentages and in relation to the specific disease.

Alzheimer's disease (AD) is an irreversible neurodegenerative disease characterized by memory loss, synaptic dysfunction and accumulation of amyloid β-peptides (Aβ). The pathogenesis of AD is believed to be caused by high levels and aggregation of amyloid-β (Aβ) in the brain. Aβ has been found to impair memory by reducing acetylation of specific histone lysines important for memory formation. Histones are proteins that closely associate with DNA molecules and play an important role in gene transcription.

Currently available therapies for AD are palliative and do not cure the disease. Cholinesterase inhibitors such as Razadync® (galantamine), Exclon® (rivastigmine), Aricept® (donepezil), and Cognex® (tacrine) have been prescribed for early stages of Alzheimer's disease, and may temporarily delay or prevent progression of symptoms related to AD. However, as AD progresses, the brain loses less acetylcholine, thereby rendering cholinesterase inhibitors unproductive as treatment for AD. Namenda® (memantine), an N-methyl D-aspartate (NMDA) antagonist, is also prescribed to treat moderate to severe Alzheimer's disease; however only temporary benefits are realized.

Histone Acetyltransferases (HATs) are involved in histone acetylation (leading to gene activation), chromosome decondensation, DNA repair and non-histone substrate modification. The post-translational acetylation status of chromatin is governed by the competing activities of two classes of enzymes, HATs and HDACs. The potential of inhibiting HDACs to counteract neurodegenerative disorders has been widely explored (*Curr Drug Targets CNS Neurol Disord,* 2005. 4(1): p. 41-50; hereby incorporated by reference in its entirety). HATs, however, have been investigated to a lesser extent. HAT activators have been reported, but many are neither soluble nor membrane permeant, which makes them poor candidates for therapeutics. CTPB and CTB are HAT activators that are insoluble and membrane-impermeable (*J Phys Chem B,* 2007. 111(17): p. 4527-34; *J Biol Chem,* 2003. 278(21): p. 19134-40; each hereby incorporated by reference in its entirety). Nemorosone is another HAT activator (*Chembiochem.* 11(6): p. 818-27; hereby incorporated by reference in its entirety). However, these compounds suffer from unfavorable physicochemical characteristics for use in CNS diseases.

There is a need for novel HAT activators. There is also a need for novel treatments for a variety of disease states for which HAT activity is implicated. There is a further need for novel and effective treatments for neurodegenerative diseases, neurological disorders and cancers. In particular, there is a continuing need for treatment of dementia and memory loss associated with Alzheimer's disease. There is also a continuing need for treatment of cancer.

SUMMARY OF THE INVENTION

In one aspect, the invention is directed to a compound of formula (I),

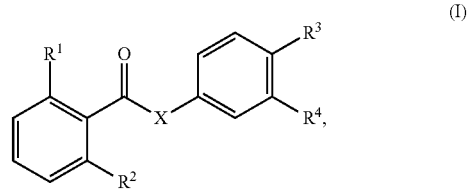

or a pharmaceutically acceptable salt or solvate thereof, wherein,

X is NH or —N(CH$_3$)—;

R$^1$ is OH, halogen, C$_1$-C$_6$-alkyl, C$_1$-C$_6$-haloalkyl, —O—(C$_1$-C$_6$-alkyl), or —O—(C$_1$-C$_6$-haloalkyl);

R$^2$ is OH, halogen, —O—(C$_2$-C$_6$-alkyl)-N(R$^5$)$_2$, —O—(C$_2$-C$_6$-alkyl)-N(R$^5$)$_3$$^+$halogen$^-$, —N(R$^5$)—(C$_2$-C$_6$-alkyl)-N(R$^5$)$_2$, or —O—(C$_1$-C$_6$-alkyl)-phenyl; wherein when R$^1$ is OH or C$_1$-C$_6$-alkyl, R$^2$ is —O—(C$_1$-C$_6$-alkyl)-phenyl or —O—(C$_2$-C$_6$-alkyl)-N(R$^5$)$_3$$^+$halogen$^-$; and wherein R$^1$ and R$^2$ are not both H; or R$^2$ and X together with the atoms to which they are attached form

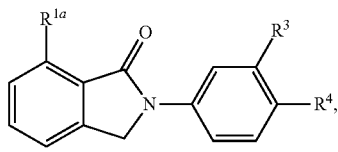

wherein R$^{1a}$ is OH; or

R$^2$ and X together with the atoms to which they are attached form

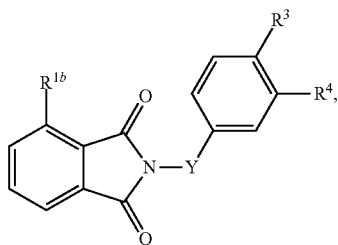

wherein Y is —(C$_1$-C$_6$-alkyl);

R$^{1b}$ is OH, O—(C$_1$-C$_6$-alkyl), —O—(C$_2$-C$_6$-alkyl)-N(R$^5$)$_2$, or —O—(C$_2$-C$_6$-alkyl)-N(R$^5$)$_3$$^+$halogen$^-$;

R$^3$ is halogen or C$_1$-C$_2$-haloalkyl;

R$^4$ is halogen or C$_1$-C$_2$-haloalkyl; or

R$^2$ and X together with the atoms to which they are attached form

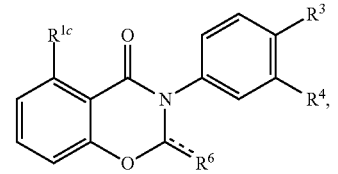

wherein

R$^{1c}$ is OH, O—(C$_1$-C$_6$-alkyl), —O—(C$_2$-C$_6$-alkyl)-N(R$^5$)$_2$, or —O—(C$_2$-C$_6$-alkyl)-N(R$^5$)$_3$$^+$halogen$^-$;

R$^3$ is halogen or C$_1$-C$_2$-haloalkyl;

R$^4$ is halogen or C$_1$-C$_2$-haloalkyl;

===== is a double bond and R$^6$ is O, or

===== is a single bond and R$^6$ is —(C$_1$-C$_6$-alkyl), —(C$_1$-C$_6$-alkyl)-N(R$^5$)$_2$, or —(C$_1$-C$_6$-alkyl)-N(R$^5$)$_3$$^+$halogen$^-$; and R$^5$ is independently H or C$_1$-C$_4$-alkyl; or a pharmaceutically acceptable salt thereof.

Another aspect of the invention provides a method for reducing amyloid beta (Aβ) protein deposits in a subject in need thereof, comprising administering to the subject a compound of formula (I), or a pharmaceutically acceptable salt or solvate thereof, or a composition comprising a compound of formula (I), or a pharmaceutically acceptable salt or solvate thereof. In some embodiments, a compound of formula (I), or a pharmaceutically acceptable salt or solvate thereof, is administered. In some embodiments, a composition comprising a compound of formula (I), or a pharmaceutically acceptable salt or solvate thereof, is administered. In some embodiments, the subject exhibits abnormally elevated levels of amyloid beta plaques. In some embodiments, the subject is afflicted with Alzheimer's disease, Lewy body dementia, inclusion body myositis, or cerebral amyloid angiopathy. In some embodiments, the Aβ protein deposit comprises an Aβ$_{40}$ isomer, an Aβ$_{42}$ isomer, or a combination of isomers.

Another aspect of the invention provides a method for treating Alzheimer's disease in a subject in need thereof, comprising administering to a subject a compound of formula (I), or a pharmaceutically acceptable salt or solvate thereof, or a composition comprising a compound of formula (I), or a pharmaceutically acceptable salt or solvate thereof. In some embodiments, a compound of formula (I), or a pharmaceutically acceptable salt or solvate thereof, is administered. In some embodiments, a composition comprising a compound of formula (I), or a pharmaceutically acceptable salt or solvate thereof, is administered. In some embodiments, a therapeutically effective amount is administered.

Another aspect of the invention provides a method for treating neurodegeneration in a subject in need thereof, comprising administering to a subject a therapeutic amount of a compound of formula (I), or a pharmaceutically acceptable salt or solvate thereof, or a composition comprising a compound of formula (I), or a pharmaceutically acceptable salt or solvate thereof. In some embodiments, a compound of formula (I), or a pharmaceutically acceptable salt or solvate thereof, is administered. In some embodiments, a composition comprising a compound of formula (I), or a pharmaceutically acceptable salt or solvate thereof, is administered. In some embodiments, memory retention in the subject is increased. In some embodiments, neurodegeneration comprises a neurodegenerative disease. In some embodiments, the neurodegenerative disease comprises Adrenolcukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy.

Another aspect of the invention provides a method for increasing synaptic plasticity in a subject afflicted with a neurodegenerative disease, comprising administering to a subject a compound of formula (I), or a pharmaceutically acceptable salt or solvate thereof, or a composition comprising a compound of formula (I), or a pharmaceutically acceptable salt or solvate thereof. In some embodiments, a compound of formula (I), or a pharmaceutically acceptable salt or solvate thereof, is administered. In some embodiments, a composition comprising a compound of formula (I), or a pharmaceutically acceptable salt or solvate thereof, is administered. In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases Progressive Supranuclear Palsy, Rett's syndrome, Tau-positive Fronto-Temporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. In some embodiments, synaptic plasticity comprises learning, memory, or a combination thereof. In some embodiments, synaptic plasticity comprises long term potentiation (LTP).

Another aspect of the invention provides a method for treating Parkinson's disease in a subject in need thereof, comprising administering to a subject a compound of formula (I), or a pharmaceutically acceptable salt or solvate thereof, or a composition comprising a compound of formula (I), or a pharmaceutically acceptable salt or solvate thereof. In some embodiments, the symptoms of Parkinson's disease are ameliorated. In some embodiments, the symptoms of Parkinson's disease comprise tremor, bradykinesia, dyskinesia, rigidity, postural instability, dystonia, akathisia, dementia, impaired gross motor coordination, or a combination of the listed symptoms. In some embodiments, the postural instability comprises impaired imbalance, impaired coordination, or a combination thereof.

Another aspect of the invention also provides a method for treating cancer in a subject in need thereof, comprising administering to a subject a compound of formula (I), or a pharmaceutically acceptable salt or solvate thereof, or a composition comprising a compound of formula (I), or a pharmaceutically acceptable salt or solvate thereof. In some embodiments, a compound of formula (I), or a pharmaceutically acceptable salt or solvate thereof, is administered. In some embodiments, a composition comprising a compound of formula (I), or a pharmaceutically acceptable salt or solvate thereof, is administered. In some embodiments, the cancer comprises B cell lymphoma, colon cancer, lung cancer, renal cancer, bladder cancer, T cell lymphoma, mycloma, leukemia, chronic mycloid leukemia, acute mycloid leukemia, chronic lymphocytic leukemia, acute lymphocytic leukemia, hematopoietic neoplasias, thymoma, lymphoma, sarcoma, lung cancer, liver cancer, non-Hodgkin's lymphoma, Hodgkin's lymphoma, uterine cancer, renal cell carcinoma, hepatoma, adenocarcinoma, breast cancer, pancreatic cancer, liver cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, astrocytoma, medulloblastoma, craniopharyngioma, ependymoma, pinealoma, hemangioblastoma, acoustic neuroma, oligodendroglioma, meningioma, retinoblastoma, leukemia, melanoma, neuroblastoma, small cell lung carcinoma, bladder carcinoma, lymphoma, multiple myeloma, follicular lymphoma or medullary carcinoma.

Another aspect of the invention provides a method for treating Huntington's disease in a subject in need thereof, comprising administering to a subject compound of formula (I), or a pharmaceutically acceptable salt or solvate thereof, or a composition comprising a compound of formula (I), or a pharmaceutically acceptable salt or solvate thereof. In some embodiments, a compound of formula (I), or a pharmaceutically acceptable salt or solvate thereof, is administered. In some embodiments, a composition comprising a compound of formula (I), or a pharmaceutically acceptable salt or solvate thereof, is administered.

Another aspect of the invention provides for a method of treating a neurodegenerative disease in a subject in need thereof, comprising administering to a subject a therapeutic amount of a compound of formula (I), or a pharmaceutically acceptable salt or solvate thereof, or a composition comprising a compound of formula (I), or a pharmaceutically acceptable salt or solvate thereof. In some embodiments, a compound of formula (I), or a pharmaceutically acceptable salt or solvate thereof, is administered. In some embodiments, a composition comprising a compound of formula (I), or a pharmaceutically acceptable salt or solvate thereof, is administered. In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases Progressive Supranuclear Palsy, Rett's syndrome, Tau-positive Fronto-Temporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy.

Another aspect of the invention provides for a method of decreasing inclusion bodies in a subject afflicted with a neurodegenerative disease, comprising administering to the subject an effective amount of a compound of formula (I), or a pharmaceutically acceptable salt or solvate thereof, or a composition comprising a compound of formula (I) or a pharmaceutically acceptable salt or solvate thereof. In some embodiments, a compound of formula (I), or a pharmaceutically acceptable salt or solvate thereof, is administered. In some embodiments, a composition comprising a compound of formula (I), or a pharmaceutically acceptable salt or solvate thereof, is administered. In some embodiments, the inclusion bodies comprise beta-amyloid peptides, native and phosphorylated Tau proteins, native and phosphorylated alpha-synuclein, lipofuscin, cleaved TARDBP (TDB-43), or a combination thereof. In other embodiments, the subject exhibits abnormally elevated levels of amyloid beta plaques. In some embodiments, the beta-amyloid peptides comprise an $A\beta_{40}$ isomer, an $A\beta_{42}$ isomer, or a combination of isomers. In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases Progressive Supranuclear Palsy, Rett's syndrome, Tau-positive Fronto-Temporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy.

DETAILED DESCRIPTION OF THE INVENTION

Figure 1:
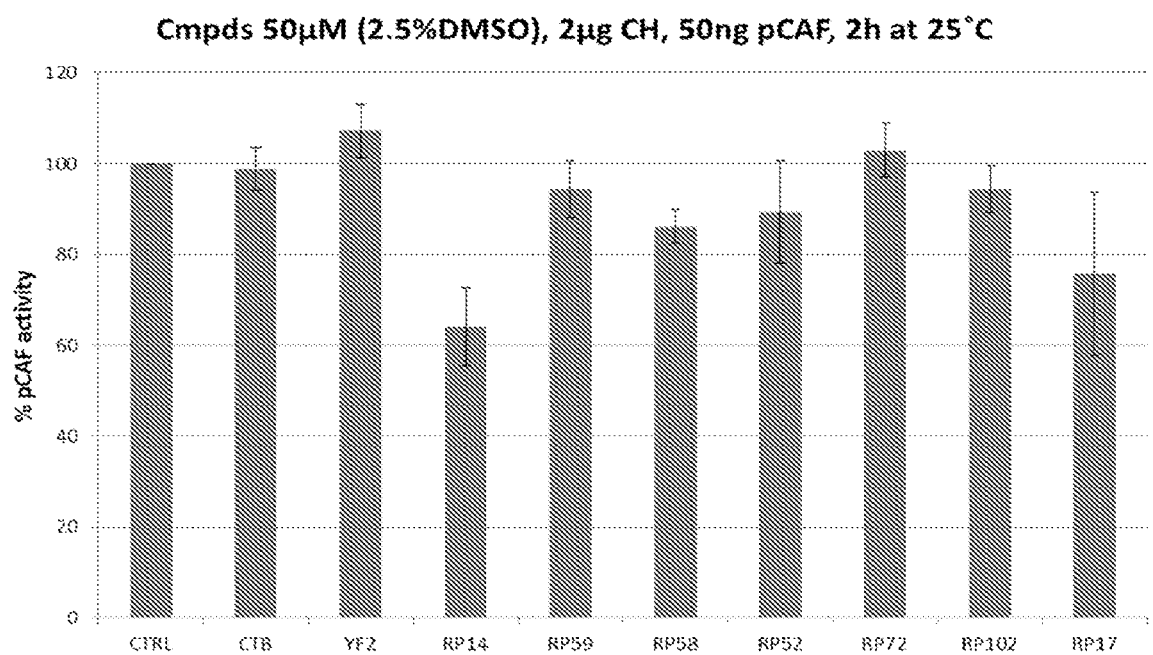
FIG. 1 shows in vitro measurement of pCAF activity for compounds.
Figure 2A:
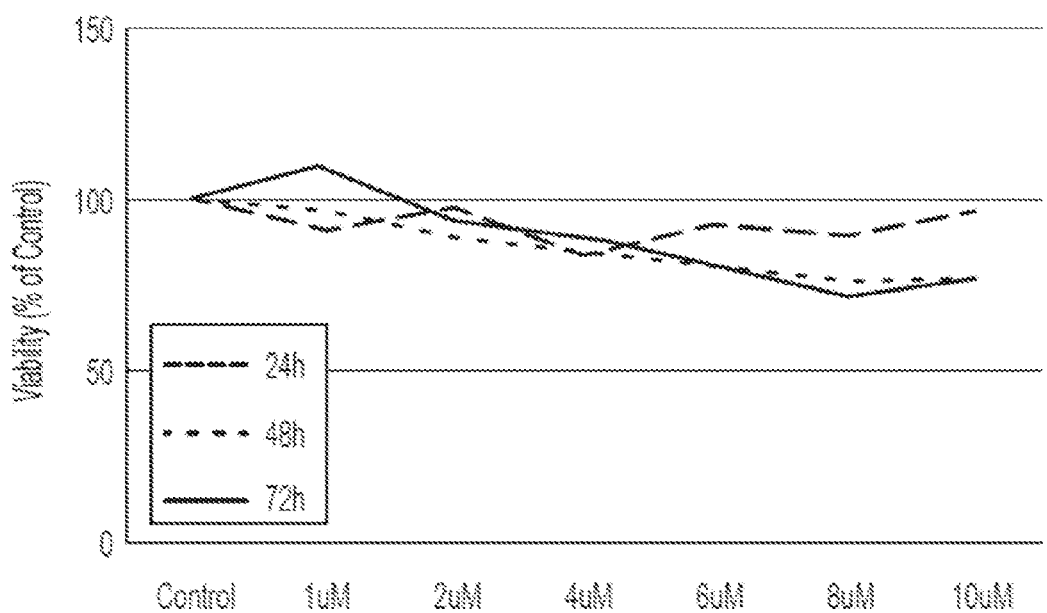
FIGS. 2A-D shows the effect relationship of RP59 for a panel of lymphoma cell lines. Cytotoxicity was evaluated using Cell-titer Glo Reagent (Promega). Cells were seeded at $0.3 \times 10^6$ cell/mL and treated with increasing concentrations of RP59 as indicated. Cytotoxicity was measured at 24 (blue line), 48 (red line), and 72 (green line) hours and compared to untreated cells. Cell lines Ly1 (A), Ly7 (B), Su-DHL6 (C), and Ly10 (D) were treated.
Figure 2B:
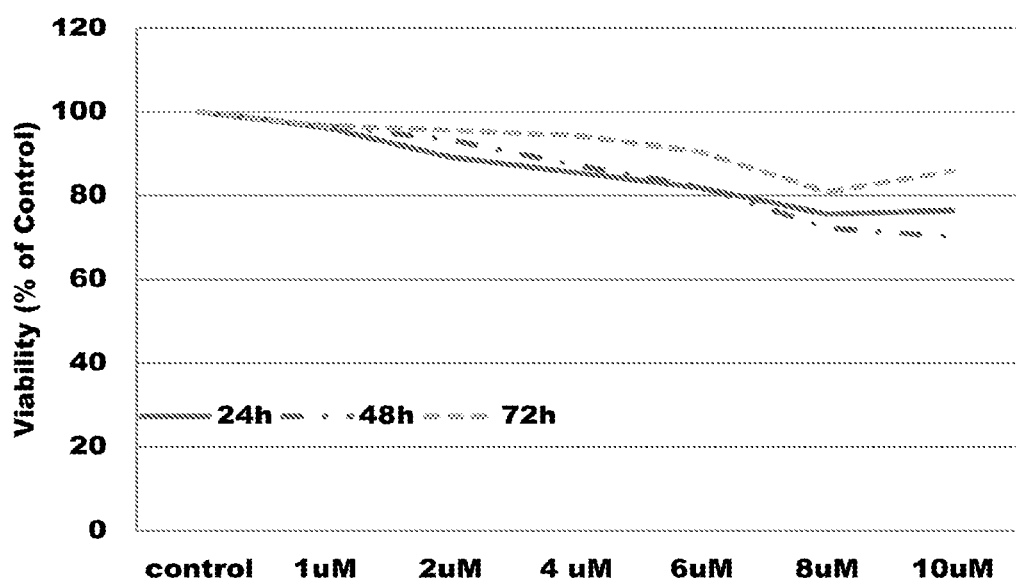
Figure 2C:
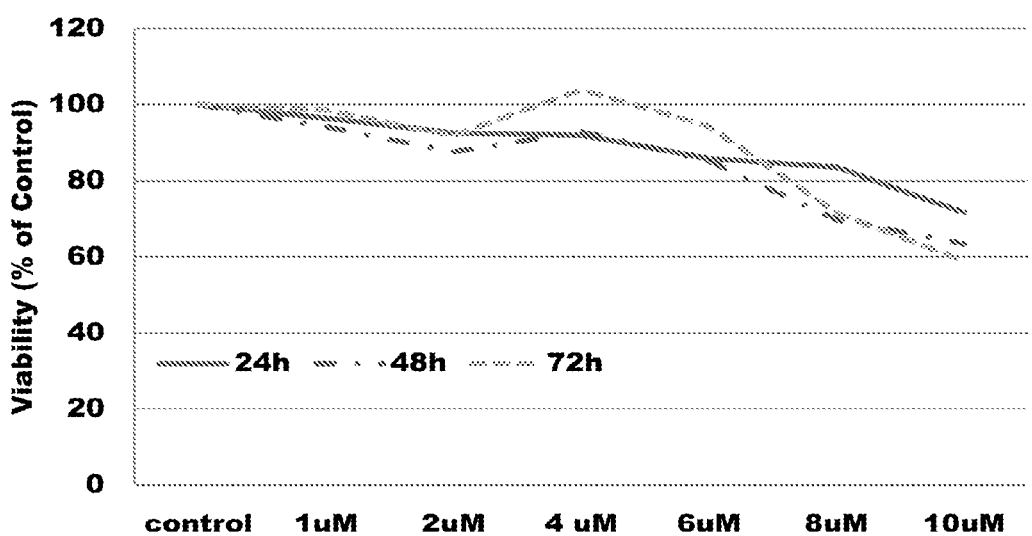
Figure 2D:
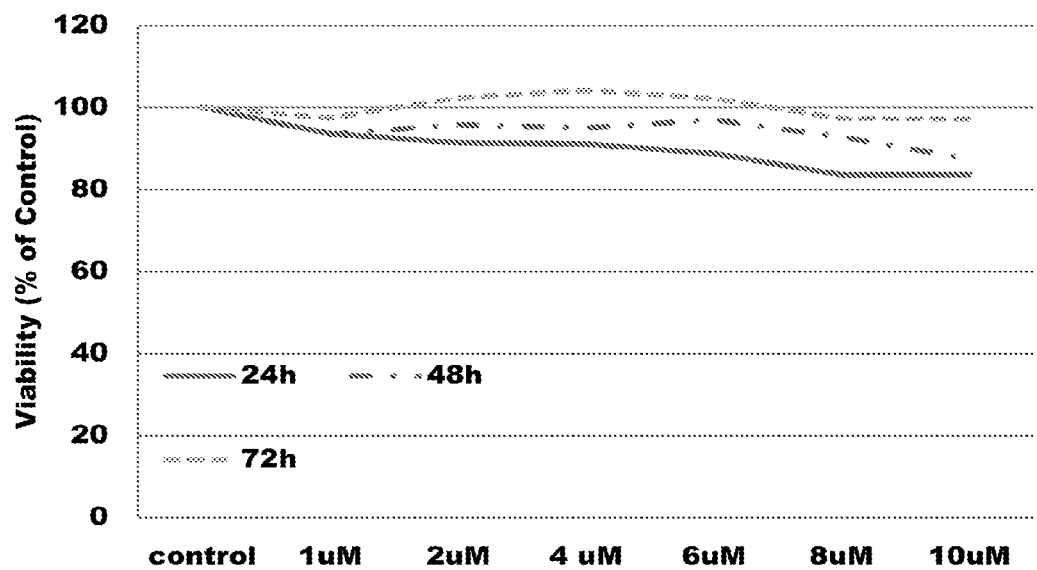
Figures 3A, 3B:
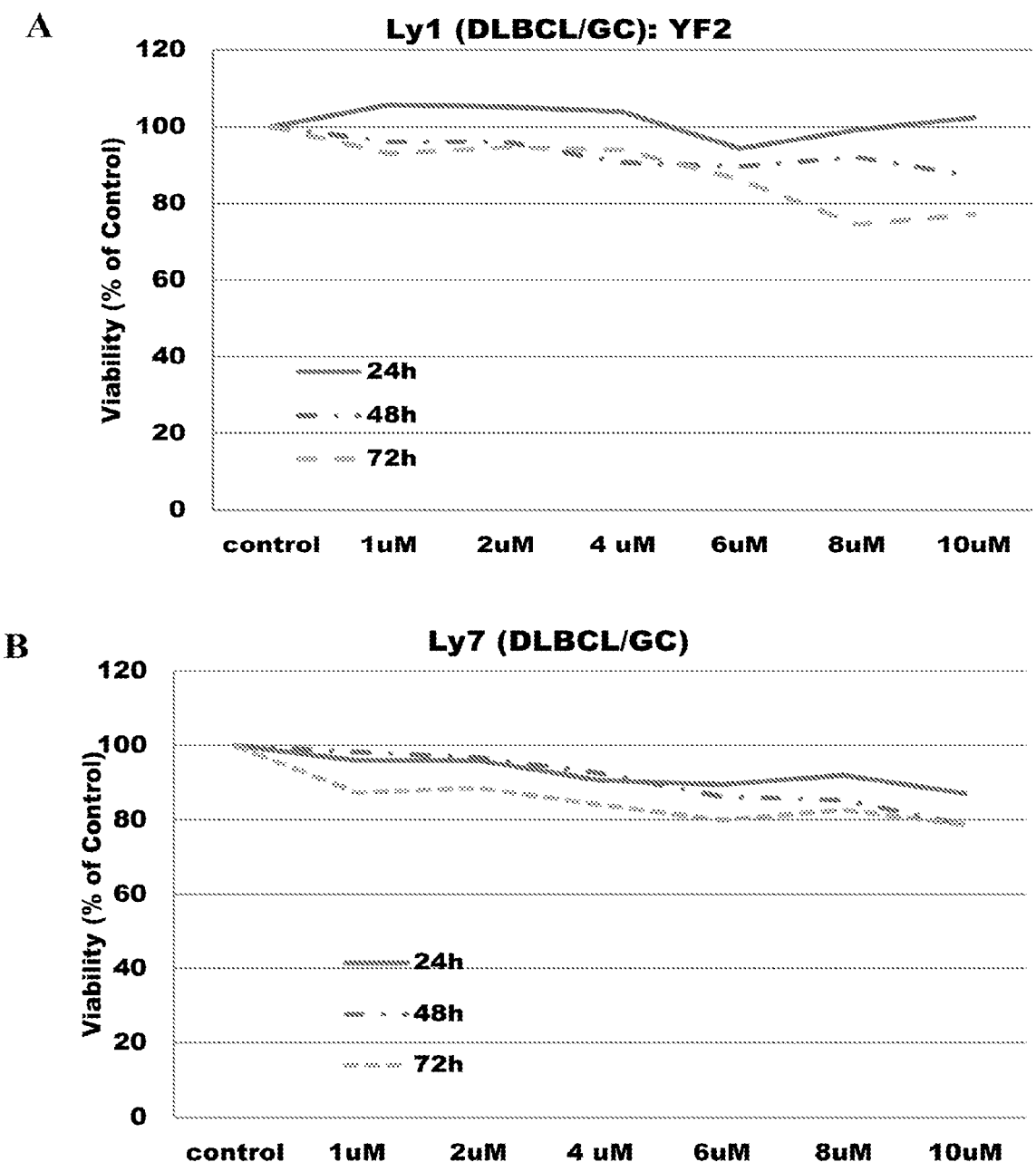
FIGS. 3A-D shows the effect relationship of YF2 for a panel of lymphoma cell lines. Cytotoxicity was evaluated using Cell-titer Glo Reagent (Promega). Cells were seeded at $0.3 \times 10^6$ cell/mL and treated with increasing concentrations of YF2 as indicated. Cytotoxicity was measured at 24 (blue line), 48 (red line), and 72 (green line) hours and compared to untreated cells. Cell lines Ly1 (A), Ly7 (B), Su-DHL6 (C), and Ly10 (D) were treated.
Figures 3C, 3D:
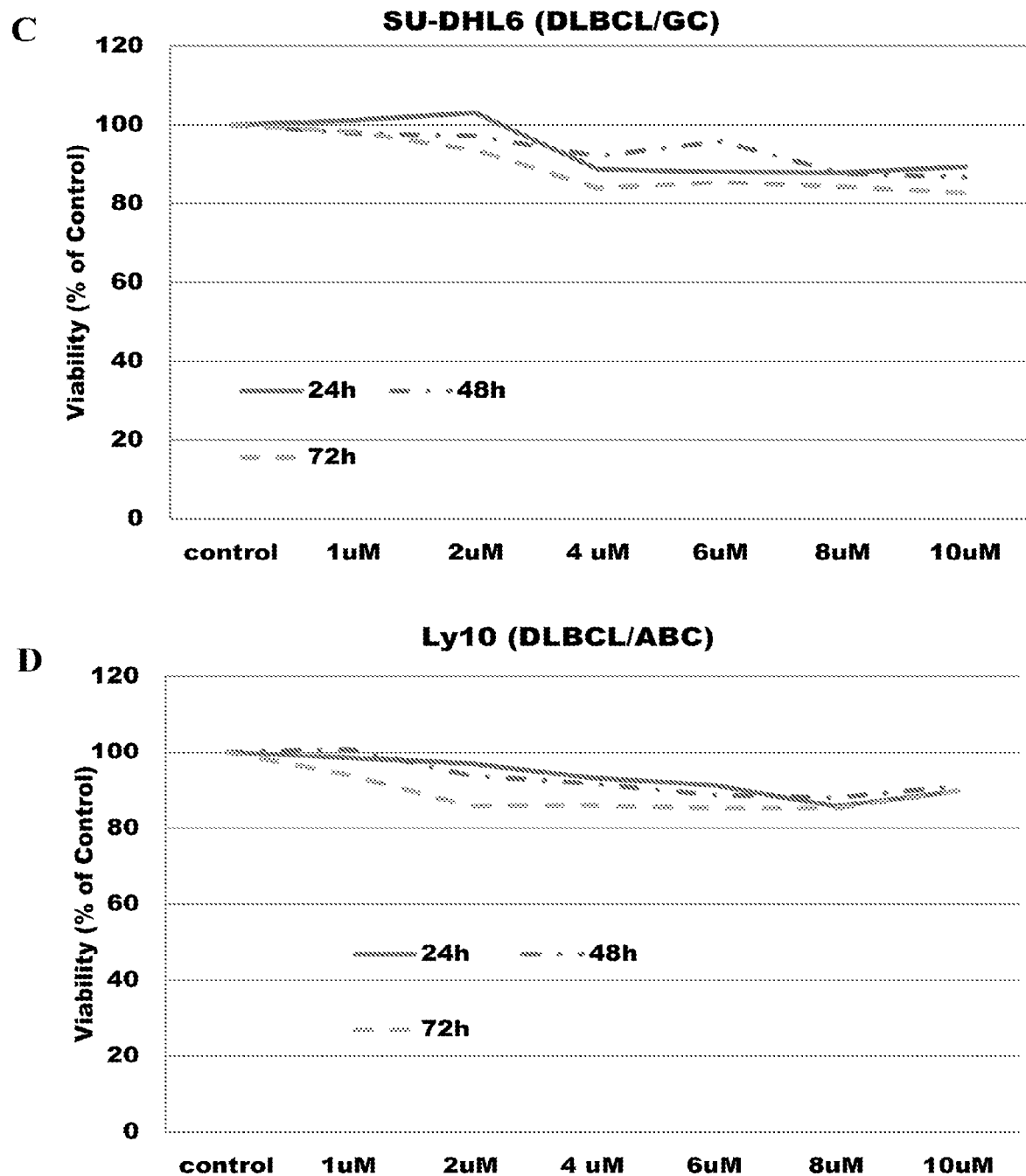
Figures 4A, 4B:
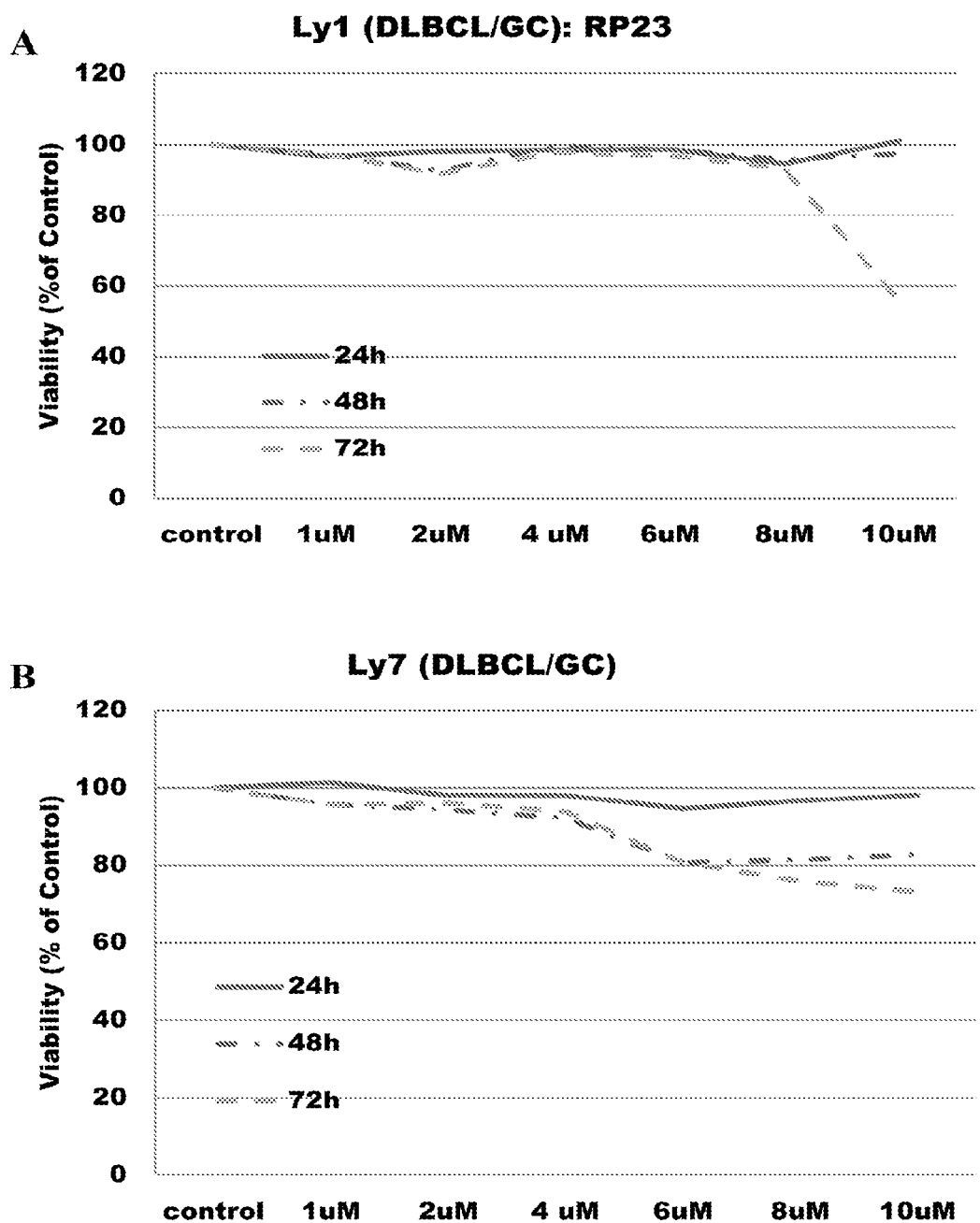
FIGS. 4A-D shows the effect relationship of RP23 for a panel of lymphoma cell lines. Cytotoxicity was evaluated using Cell-titer Glo Reagent (Promega). Cells were seeded at $0.3 \times 10^6$ cell/mL and treated with increasing concentrations of RP23 as indicated. Cytotoxicity was measured at 24 (blue line), 48 (red line), and 72 (green line) hours and compared to untreated cells. Cell lines Ly1 (A), Ly7 (B), Su-DHL6 (C), and Ly10 (D) were treated.
Figures 4C, 4D:
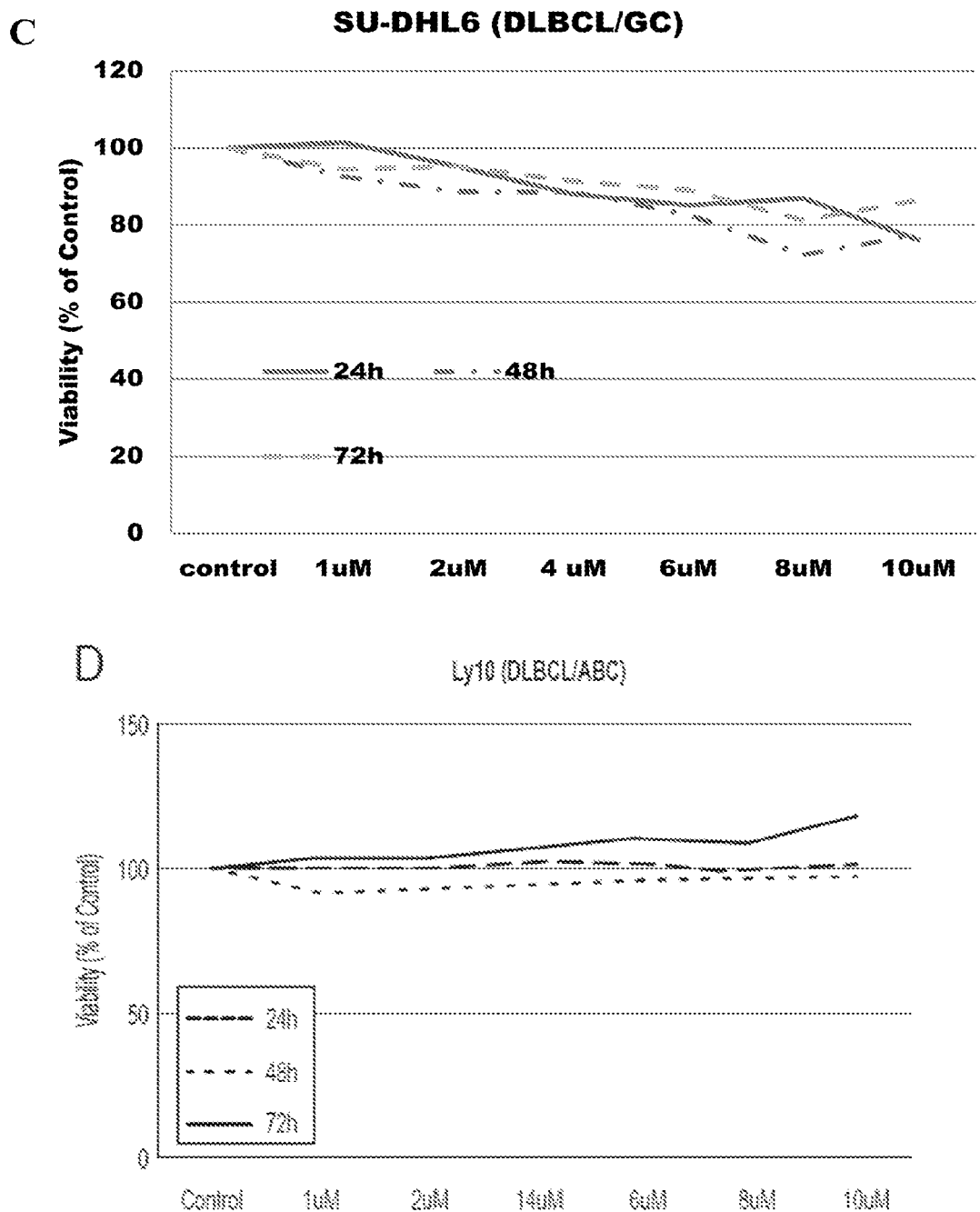
Figure 5A:
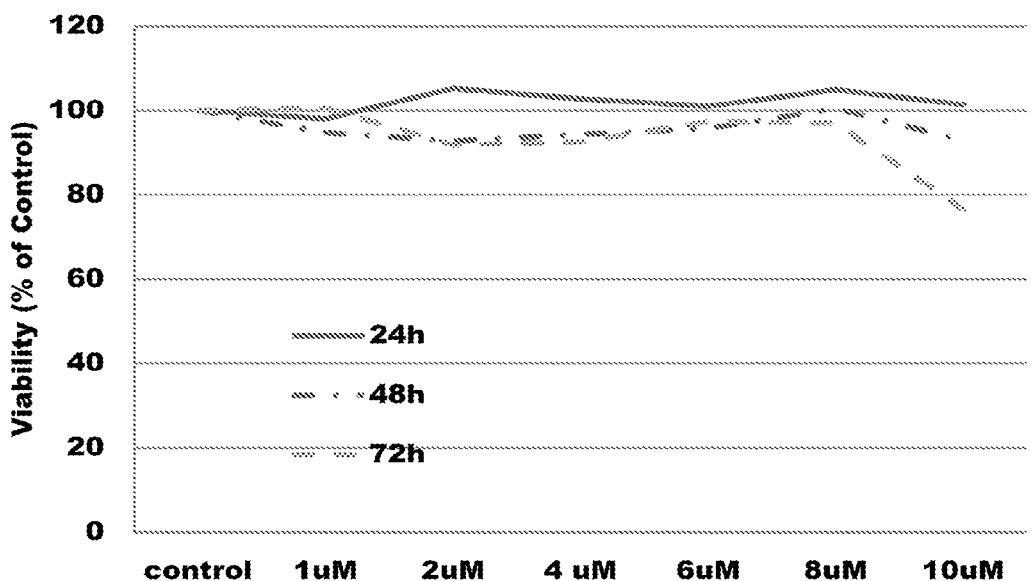
FIGS. 5A-D shows the effect relationship of RP58 for a panel of lymphoma cell lines. Cytotoxicity was evaluated using Cell-titer Glo Reagent (Promega). Cells were seeded at $0.3 \times 10^6$ cell/mL and treated with increasing concentrations of RP58 as indicated. Cytotoxicity was measured at 24 (blue line), 48 (red line), and 72 (green line) hours and compared to untreated cells. Cell lines Ly1 (A), Ly7 (B), Su-DHL6 (C), and Ly10 (D) were treated.
Figure 5B:
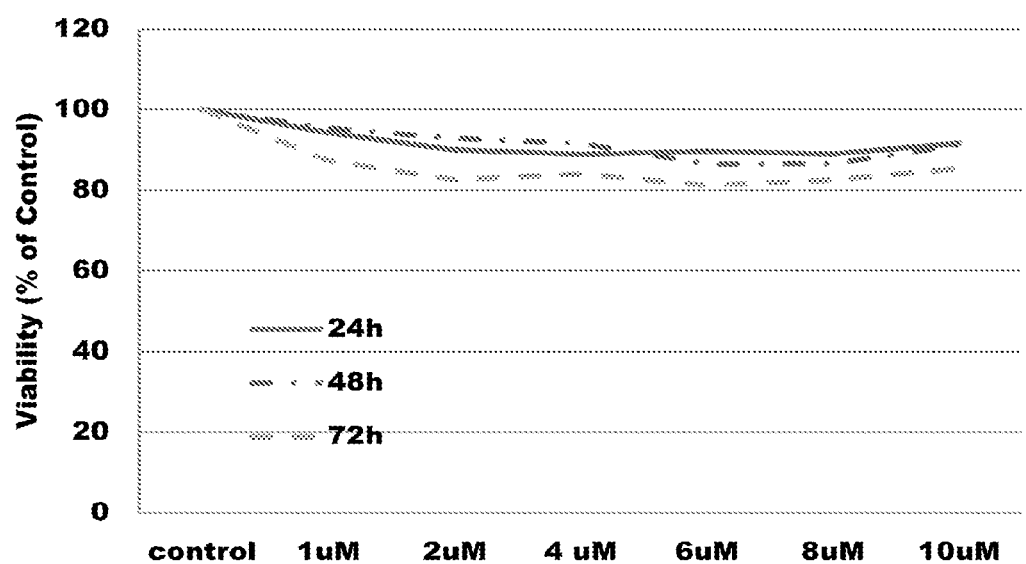
Figure 5C:
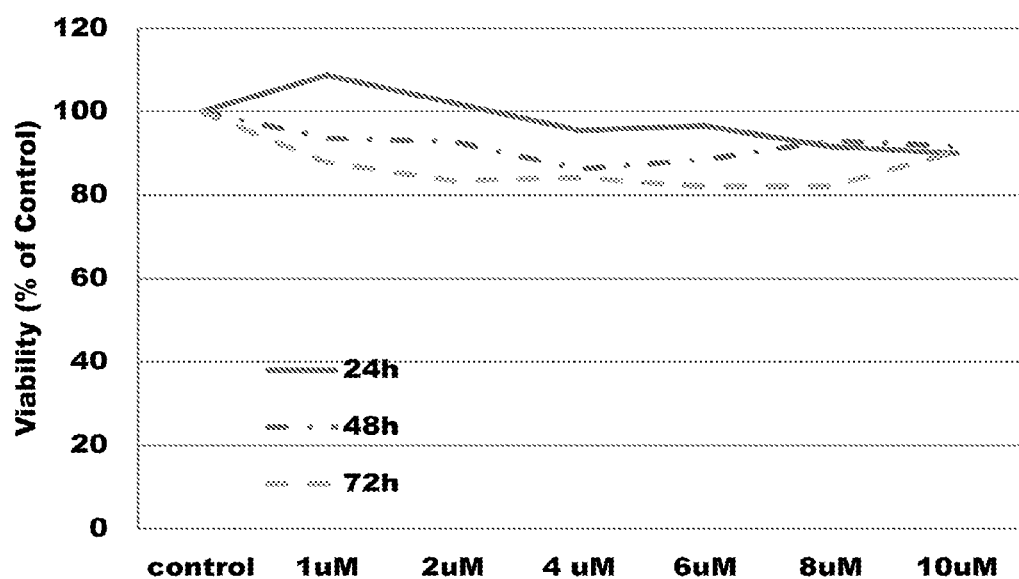
Figure 5D:
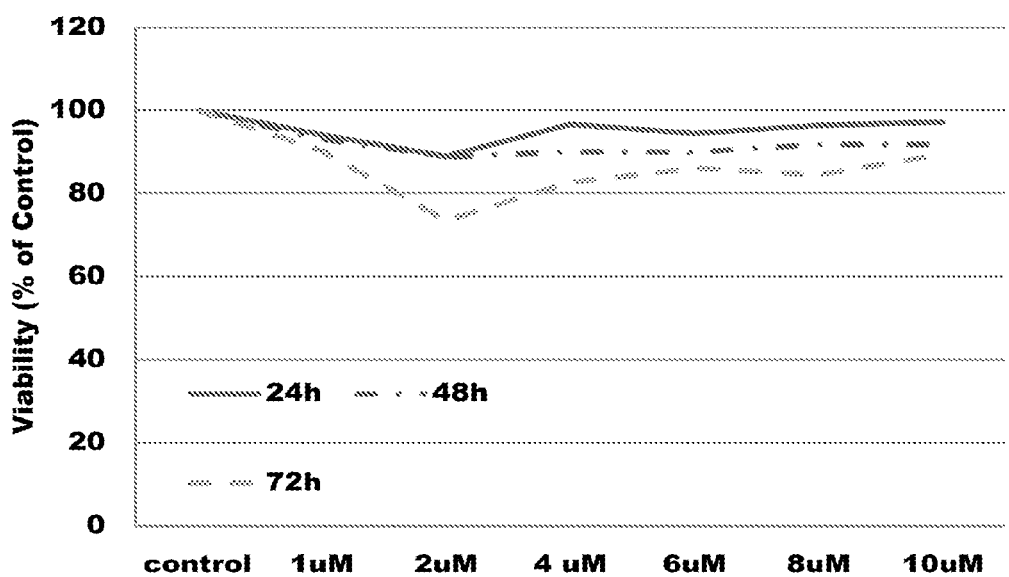

The term "compound of the invention" as used herein encompasses, for example, compound of formula (I) and any subgenera and/or species, or a pharmaceutically acceptable salt or solvate thereof.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "in need thereof" refers to the need for symptomatic or asymptomatic relief from a condition such as, for example, cancer or a neurodegenerative disease. The subject in need thereof may or may not be undergoing treatment for conditions related to, for example, cancer or a neurodegenerative disease.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, $21^{st}$ Edition (University of the Sciences in Philadelphia, ed., Lippincott Williams & Wilkins 2005); and Handbook of Pharmaceutical Excipients, $7^{th}$ Edition (Raymond Rowe et al., ed., Pharmaceutical Press 2012); each hereby incorporated by reference in its entirety.

The term "pharmaceutically acceptable" as used herein means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salt" as used herein includes both acid and base addition salts. An acid addition salt refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

A base addition salt refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The term "solvate" as used herein means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is a "hydrate." Examples of hydrate include, but are not limited to, hemihydrate, monohydrate, dihydrate, trihydrate, hexahydrate, etc. It should be understood by one of ordinary skill in the art that the present compound and/or the pharmaceutically acceptable salt of the present compound may also exist in a solvate form. The solvate is typically formed via hydration which is either part of the preparation of the present compound or through natural absorption of moisture by the anhydrous compound of the present invention.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and etc.) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted olefin isomer. When the chemical name does not specify the isomeric form of the compound, it denotes any one of the possible isomeric forms or a mixture of those isomeric forms of the compound.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S. The phrase "a single enantiomer, a mixture of enantiomers, a mixture of diastereomers, or an isotopic variant thereof; or a pharmaceutically acceptable salt, solvate, or prodrug thereof" has the same meaning as the phrase "a single enantiomer, a mixture of enantiomers, a mixture of diastereomers, or an isotopic variant of the compound referenced therein; or a pharmaceutically acceptable salt, solvate, or prodrug of the compound referenced therein, or a single enantiomer, a mixture of enantiomers, a mixture of diastereomers, or an isotopic variant of the compound referenced therein."

The compounds described herein may also exist in several tautomeric forms. The term "tautomer" as used herein refers to isomers that change into one another with great ease by a proton or an alkyl shift from one atom of a molecule to another atom of the same molecule so that they can exist together in equilibrium. For example, ketone and enol are two tautomeric forms of one compound.

The terms "animal," "subject" and "patient" as used herein includes all members of the animal kingdom including, but not limited to, mammals, animals (e.g., cats, dogs, horses, swine, etc.) and humans.

The term "alkyl" as used herein, by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined hereinbelow. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined hereinbelow. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 10 carbon atoms ($C_1$-$C_{10}$ alkylene). In still other embodiments, an alkylene group comprises from 1 to 6 carbon atoms ($C_1$-$C_6$ alkylene).

The term "alkanyl" as used herein, by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined hereinbelow. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

The term "alkenyl" as used herein, by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined hereinbelow. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

The term "alkynyl" as used herein, by itself or as part of another substituent, refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

The term "cycloalkyl" as used herein refers to a cyclic monovalent hydrocarbon radical derived by the removal of one hydrogen atom from a single carbon atom of a parent cycloalkane, cycloalkene or cycloalkyne. The term "cycloalkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "cycloalkanyl," "cycloalkenyl," and "cycloalkynyl" are used. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

An "aromatic" moiety or "aryl" moiety refers to a monocyclic or fused bicyclic moiety having the well-known characteristics of aromaticity; examples include phenyl and naphthyl.

The terms "halogen" or "halo" as used herein includes fluoro, chloro, bromo and iodo groups. The term "haloalkyl" as used herein includes an alkyl group, as defined above, where one or more H is replaced with a halogen. Non-limiting examples include monofluoromethyl, difluoromethyl, trifluoromethyl, perfluoroethyl, 2,2,2-trifluoroethyl, 2,2-difluoroethyl, 2-fluoroethyl, and the like.

Each alkyl, cycloalkyl, haloalkyl, and aryl groups may optionally be substituted with one or more substituents to the extent that such substitution makes sense chemically.

"Optionally substituted" means substituted or not substituted. As used herein, "optionally substituted" indicates that the particular group or groups being described may have no non-hydrogen substituents, or the group or groups may have one or more non-hydrogen substituents. If not otherwise specified, the total number of such substituents that may be present is equal to or less than the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Substituted," when used to modify a specified group or radical, means that one or more hydrogen atoms of the specified group or radical are each, independently of one another, replaced with the same or different substituent(s).

Substituent groups useful for substituting saturated carbon atoms in the specified group or radical include, but are not limited to —$R^a$, halo, acyl, —O—, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O$—, —$S(O)_2$ $OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)$ $OR^b$, —$C(O)NR^cR^c$, —$C(NR^b)NR^cR^c$, —OC$(O)R^b$, —OC$(S)R^b$, —OC$(O)O^-$, —OC$(O)OR^b$, —OC$(S)$ OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —NR$^c$R$^c$ is meant to include —NH$_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)OR$^b$, -alkylene-C(O)NR$^b$R$^b$, and —CH$_2$—CH$_2$—C(O)—CH$_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —R$^a$, halo, acyl, —O$^-$, —OR$^b$, —SR$^b$, —S$^-$, —NR$^c$R$^c$, trihalomethyl, —CF$_3$, —CN, —OCN, —SCN, —NO, —NO$_2$, —N$_3$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

The term "heteroalkyl" as used herein includes alkyl groups, as defined above, when heteroatoms (N, O and S typically) are allowed to replace carbon atoms. For example, the numbers describing the group, though still written as e.g. $C_1$-$C_6$, represent the sum of the number of carbon atoms in the group plus the number of such heteroatoms that are included as replacements for carbon atoms in the backbone of the ring or chain being described. When the carbon atoms of a cycloalkyl group, as defined above, are replaced with heteroatom it is referred to as "cycloheteroalkyl."

The terms "heteroaromatic" and "heteroaryl" as used herein, refer to aromatic monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic $C_5$-$C_6$ aromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl and the fused bicyclic moieties formed by fusing one of these monocyclic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms and up to four heteroatoms selected from N, O and S.

Frequently, the monocyclic heteroaryls contain 5-6 ring members and up to three such heteroatoms, and the bicyclic heteroaryls contain 8-10 ring members and up to four such heteroatoms. The number and placement of heteroatoms in such rings is in accordance with the well-known limitations of aromaticity and stability, where stability requires the heteroaromatic group to be stable enough to be exposed to water without rapid degradation.

The terms "arylalkyl" and "heteroarylalkyl" as used herein refer to aromatic and heteroaromatic ring systems which are bonded to their attachment point through a divalent alkyl group, as defined above. For example, benzyl group is an arylalkyl group.

As used herein, "acyl" encompasses groups comprising an alkyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

In some embodiments, X is NH or —N(CH$_3$)—;
R$^1$ is H, OH, halogen, $C_1$-$C_6$-alkyl, $C_1$-$C_6$-haloalkyl, —O—($C_1$-$C_6$-alkyl), or —O—($C_1$-$C_6$-haloalkyl);
R$^2$ is H, OH, halogen, —O—($C_2$-$C_6$-alkyl)-N(R$^5$)$_2$, —O—($C_2$-$C_6$-alkyl)-N(R$^5$)$_3$$^+$halogen$^-$, —N(R$^5$)—($C_2$-$C_6$-alkyl)-N(R$^5$)$_2$, or —O—($C_1$-$C_6$-alkyl)-phenyl; wherein when R$^1$ is OH or $C_1$-$C_6$-alkyl, R$^2$ is OH, —O—($C_1$-$C_6$-alkyl)-phenyl, or —O—($C_2$-$C_6$-alkyl)-N(R$^5$)$_3$$^+$halogen$^-$; when R$^1$ is H, R$^2$ is —N(R$^5$)—($C_2$-$C_6$-alkyl)-N(R$^5$)$_2$; and wherein R$^1$ and R$^2$ are not both H; or R$^2$ and X together with the atoms to which they are attached form

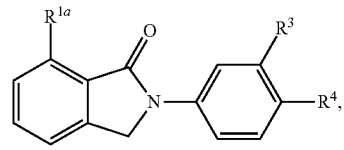

wherein R$^{1a}$ is OH or OCH$_3$; or
R$^2$ and X together with the atoms to which they are attached form

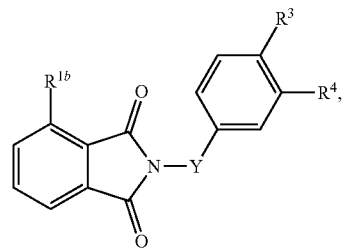

wherein Y is —($C_1$-$C_2$-alkyl);
R$^{1b}$ is OH, O—($C_1$-$C_6$-alkyl), —O—($C_2$-$C_6$-alkyl)-N(R$^5$)$_2$, or —O—($C_2$-$C_6$-alkyl)-N(R$^5$)$_3$$^+$halogen$^-$;
R$^3$ is halogen or $C_1$-$C_2$-haloalkyl;
R$^4$ is halogen or $C_1$-$C_2$-haloalkyl; or
R$^2$ and X together with the atoms to which they are attached form

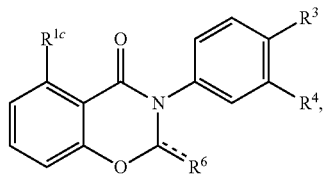

wherein
$R^{1c}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl;
$R^5$ is independently H or $C_1$-$C_4$-alkyl; and
==== is a double bond and $R^6$ is O, or
==== is a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3$$^+$halogen$^-$; or a pharmaceutically acceptable salt thereof.

In some embodiments, X is NH or —N(CH$_3$)—;
$R^1$ is OH, halogen, $C_1$-$C_6$-alkyl, $C_1$-$C_6$-haloalkyl, —O—($C_1$-$C_6$-alkyl), or —O—($C_1$-$C_6$-haloalkyl);
$R^2$ is OH, halogen, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is $C_1$-$C_6$-alkyl, $R^2$ is —O—($C_1$-$C_6$-alkyl)-phenyl or —O—($C_2$-$C_6$-alkyl)-N($R^5$)$_3$$^+$halogen$^-$; when $R^1$ is —O($C_1$-$C_6$-alkyl), $R^2$ is halogen, —O—($C_1$-$C_6$-alkyl)-phenyl, or —O—($C_2$-$C_6$-alkyl)-N($R^5$)$_3$$^+$halogen$^-$; and wherein $R^1$ and $R^2$ are not both H; or $R^2$ and X together with the atoms to which they are attached form

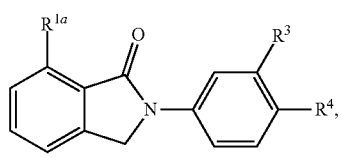

wherein $R^{1a}$ is OH; or $R^2$ and X together with the atoms to which they are attached form

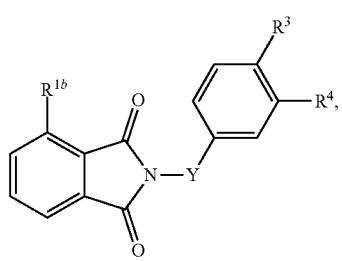

wherein Y is —($C_1$-$C_2$-alkyl);
$R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl; or $R^2$ and X together with the atoms to which they are attached form

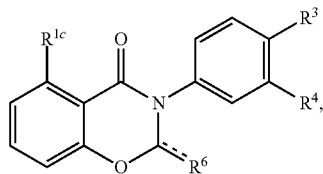

wherein
$R^{1c}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl;
$R^5$ is independently H or $C_1$-$C_4$-alkyl; and
==== is a double bond and $R^6$ is O, or
==== is a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3$$^+$halogen$^-$; or a pharmaceutically acceptable salt thereof.

In some embodiments, X is NH or —N(CH$_3$)—;
$R^1$ is H, OH, $C_1$-$C_6$-alkyl, $C_1$-$C_6$-haloalkyl, —O—($C_1$-$C_6$-alkyl), or —O—($C_1$-$C_6$-haloalkyl);
$R^2$ is H, OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH or $C_1$-$C_6$-alkyl, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is H, $R^2$ is —N($R^5$)—($C_2$-$C_6$-alkyl)-N($R^5$)$_2$; and wherein $R^1$ and $R^2$ are not both H; or $R^2$ and X together with the atoms to which they are attached form

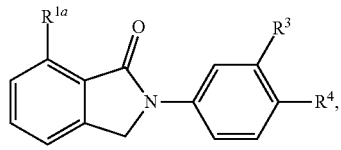

wherein $R^{1a}$ is OH or OCH$_3$; or $R^2$ and X together with the atoms to which they are attached form

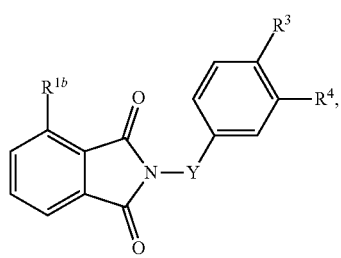

wherein Y is —($C_1$-$C_2$-alkyl);
$R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl; or $R^2$ and X together with the atoms to which they are attached form

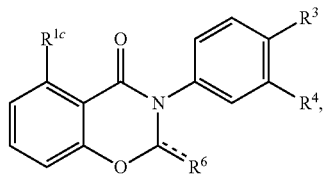

wherein
$R^{1c}$ is OH, O—($C_1$-$C_6$-alkyl), O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl;
$R^5$ is independently H or $C_1$-$C_4$-alkyl; and
===== is a double bond and $R^6$ is O, or
===== is a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3$$^+$halogen$^-$; or a pharmaceutically acceptable salt thereof.

In some embodiments, X is NH or —N(CH$_3$)—;
$R^1$ is OH, $C_1$-$C_6$-alkyl, $C_1$-$C_6$-haloalkyl, —O—($C_1$-$C_6$-alkyl), or —O—($C_1$-$C_6$-haloalkyl);
$R^2$ is OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is $C_1$-$C_6$-alkyl or —O—($C_1$-$C_6$-alkyl), $R^2$ is —O—($C_1$-$C_6$-alkyl)-phenyl or —O—($C_2$-$C_6$-alkyl)-N($R^5$)$_3$$^+$halogen$^-$; and wherein $R^1$ and $R^2$ are not both H; or $R^2$ and X together with the atoms to which they are attached form

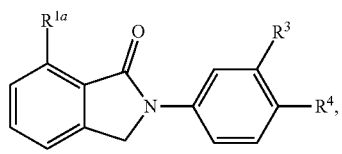

wherein $R^{1a}$ is OH; or
$R^2$ and X together with the atoms to which they are attached form

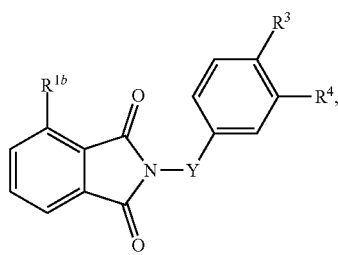

wherein Y is —($C_1$-$C_2$-alkyl);
$R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl; or
$R^2$ and X together with the atoms to which they are attached form

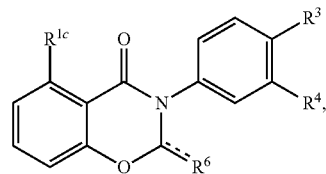

wherein
$R^{1c}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl;
$R^5$ is independently H or $C_1$-$C_4$-alkyl; and
===== is a double bond and $R^6$ is O, or
===== a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3$$^+$halogen$^-$; or a pharmaceutically acceptable salt thereof.

In some embodiments, X is NH or —N(CH$_3$)—;
$R^1$ is H, OH, halogen, $C_1$-$C_6$-alkyl, $C_1$-$C_6$-haloalkyl, —O—($C_1$-$C_6$-alkyl), or —O—($C_1$-$C_6$-haloalkyl);
$R^2$ is H, OH, halogen, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH or $C_1$-$C_6$-alkyl, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is H, $R^2$ is —N($R^5$)—($C_2$-$C_6$-alkyl)-N($R^5$)$_2$; and wherein $R^1$ and $R^2$ are not both H; or $R^2$ and X together with the atoms to which they are attached form wherein $R^{1a}$ is OH or OCH$_3$; or
$R^2$ and X together with the atoms to which they are attached form wherein $R^{1b}$ is OH, O—($C_1$-$C_6$-alkyl), or —O—($C_2$-$C_6$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is OH, halogen, $C_1$-$C_6$-alkyl, $C_1$-$C_6$-haloalkyl, —O—($C_1$-$C_6$-alkyl), or —O—($C_1$-$C_6$-haloalkyl);
$R^2$ is OH, halogen, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N ($R^5$)$_2$, or —O—($C_1$-$C_6$-alkyl)-phenyl; wherein when $R^1$ is OH, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is $C_1$-$C_6$-alkyl, $R^2$ is —O—($C_1$-$C_6$-alkyl)-phenyl or —O—($C_2$-$C_6$-alkyl)-N($R^5$)$_3$$^+$halogen$^-$; when $R^1$ is —O—($C_1$-$C_6$-alkyl), $R^2$ is halogen, —O—($C_1$-$C_6$-alkyl)-phenyl, or —O—($C_2$-$C_6$-alkyl)-N($R^5$)$_3$$^+$halogen$^-$; and wherein $R^1$ and $R^2$ are not both H; or $R^2$ and X together with the atoms to which they are attached form

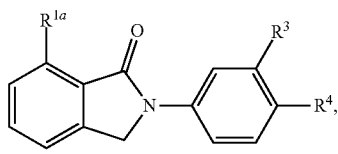

wherein $R^{1a}$ is OH; or $R^2$ and X together with the atoms to which they are attached form

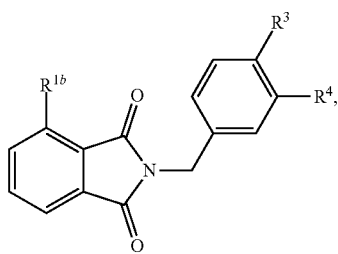

wherein $R^{1b}$ is OH, O—($C_1$-$C_6$-alkyl), or O—($C_2$-$C_6$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is H, OH, $C_1$-$C_6$-alkyl, $C_1$-$C_6$-haloalkyl, —O—($C_1$-$C_6$-alkyl), or —O—($C_1$-$C_6$-haloalkyl);
$R^2$ is H, OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH or $C_1$-$C_6$-alkyl, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is H, $R^2$ is —N($R^5$)—($C_2$-$C_6$-alkyl)-N($R^5$)$_2$; and wherein $R^1$ and $R^2$ are not both H; or $R^2$ and X together with the atoms to which they are attached form

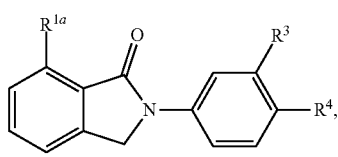

wherein $R^{1a}$ is OH or OCH$_3$; or $R^2$ and X together with the atoms to which they are attached form

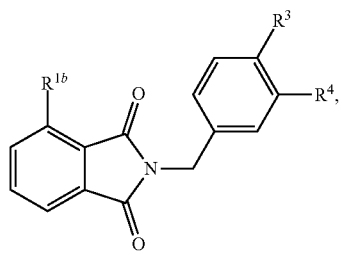

wherein $R^{1b}$ is OH, O—($C_1$-$C_6$-alkyl), or —O—($C_2$-$C_6$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is OH, $C_1$-$C_6$-alkyl, $C_1$-$C_6$-haloalkyl, —O—($C_1$-$C_6$-alkyl), or —O—($C_1$-$C_6$-haloalkyl);
$R^2$ is OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is $C_1$-$C_6$-alkyl or —O—($C_1$-$C_6$-alkyl), $R^2$ is —O—($C_1$-$C_6$-alkyl)-phenyl or —O—($C_2$-$C_6$-alkyl)-N($R^5$)$_3$$^+$halogen$^-$; and wherein $R^1$ and $R^2$ are not both H; or $R^2$ and X together with the atoms to which they are attached form

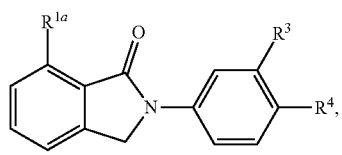

wherein $R^{1a}$ is OH; or $R^2$ and X together with the atoms to which they are attached form

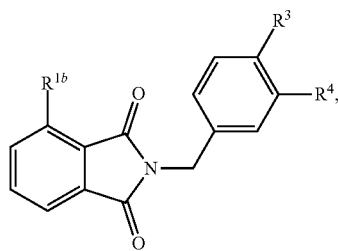

wherein $R^{1b}$ is OH, O—($C_1$-$C_6$-alkyl), or —O—($C_2$-$C_6$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is H, OH, halogen, $C_1$-$C_6$-alkyl, $C_1$-$C_6$-haloalkyl, —O—($C_1$-$C_6$-alkyl), or —O—($C_1$-$C_6$-haloalkyl);
$R^2$ is H, OH, halogen, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-

N(R$^5$)$_2$, or —O—(C$_1$-C$_6$-alkyl)-phenyl; wherein when R$^1$ is OH or C$_1$-C$_6$-alkyl, R$^2$ is OH, —O—(C$_1$-C$_6$-alkyl)-phenyl, or —O—(C$_2$-C$_6$-alkyl)-N(R$^5$)$_3$$^+$halogen$^-$; when R$^1$ is H, R$^2$ is —N(R$^5$)—(C$_2$-C$_6$-alkyl)-N(R$^5$)$_2$; and wherein R$^1$ and R$^2$ are not both H; or R$^2$ and X together with the atoms to which they are attached form wherein R$^{1a}$ is OH or OCH$_3$; or
R$^2$ and X together with the atoms to which they are attached form wherein R$^{1b}$ is OH, O—(C$_1$-C$_6$-alkyl), or —O—(C$_2$-C$_6$-alkyl)-N(R$^5$)$_2$;
R$^3$ is halogen or C$_1$-C$_2$-haloalkyl;
R$^4$ is halogen or C$_1$-C$_2$-haloalkyl; and
R$^5$ is independently H or C$_1$-C$_4$-alkyl; or a pharmaceutically acceptable salt thereof.

In some embodiments, X is NH or —N(CH$_3$)—;
R$^1$ is OH, halogen, C$_1$-C$_6$-alkyl, C$_1$-C$_6$-haloalkyl, —O—(C$_1$-C$_6$-alkyl), or —O—(C$_1$-C$_6$-haloalkyl);
R$^2$ is OH, halogen, —O—(C$_2$-C$_6$-alkyl)-N(R$^5$)$_2$, —O—(C$_2$-C$_6$-alkyl)-N(R$^5$)$_3$$^+$halogen$^-$, —N(R$^5$)—(C$_2$-C$_6$-alkyl)-N(R$^5$)$_2$, or —O—(C$_1$-C$_6$-alkyl)-phenyl; wherein when R$^1$ is OH, R$^2$ is OH, —O—(C$_1$-C$_6$-alkyl)-phenyl, or —O—(C$_2$-C$_6$-alkyl)-N(R$^5$)$_3$$^+$halogen$^-$; when R$^1$ is C$_1$-C$_6$-alkyl, R$^2$ is —O—(C$_1$-C$_6$-alkyl)-phenyl or —O—(C$_2$-C$_6$-alkyl)-N(R$^5$)$_3$$^+$halogen$^-$; when R$^1$ is —O—(C$_1$-C$_6$-alkyl), R$^2$ is halogen, —O—(C$_1$-C$_6$-alkyl)-phenyl or —O—(C$_2$-C$_6$-alkyl)-N(R$^5$)$_3$$^+$halogen$^-$; and wherein R$^1$ and R$^2$ are not both H; or R$^2$ and X together with the atoms to which they are attached form wherein R$^{1a}$ is OH; or
R$^2$ and X together with the atoms to which they are attached form wherein R$^{1b}$ is OH, O—(C$_1$-C$_6$-alkyl), or O—(C$_2$-C$_6$-alkyl)-N(R$^5$)$_2$;
R$^3$ is halogen or C$_1$-C$_2$-haloalkyl;
R$^4$ is halogen or C$_1$-C$_2$-haloalkyl; and
R$^5$ is independently H or C$_1$-C$_4$-alkyl; or a pharmaceutically acceptable salt thereof.

In some embodiments, X is NH or —N(CH$_3$)—;
R$^1$ is H, OH, C$_1$-C$_6$-alkyl, C$_1$-C$_6$-haloalkyl, —O—(C$_1$-C$_6$-alkyl), or —O—(C$_1$-C$_6$-haloalkyl);
R$^2$ is H, OH, —O—(C$_2$-C$_6$-alkyl)-N(R$^5$)$_2$, —O—(C$_2$-C$_6$-alkyl)-N(R$^5$)$_3$$^+$halogen$^-$, —N(R$^5$)—(C$_2$-C$_6$-alkyl)-N(R$^5$)$_2$, or —O—(C$_1$-C$_6$-alkyl)-phenyl; wherein when R$^1$ is OH or C$_1$-C$_6$-alkyl, R$^2$ is OH, —O—(C$_1$-C$_6$-alkyl)-phenyl, or —O—(C$_2$-C$_6$-alkyl)-N(R$^5$)$_3$$^+$halogen$^-$; when R$^1$ is H, R$^2$ is —N(R$^5$)—(C$_2$-C$_6$-alkyl)-N(R$^5$)$_2$; and wherein R$^1$ and R$^2$ are not both H; or R$^2$ and X together with the atoms to which they are attached form wherein R$^{1a}$ is OH or OCH$_3$; or
R$^2$ and X together with the atoms to which they are attached form wherein R$^{1b}$ is OH, O—(C$_1$-C$_6$-alkyl), or —O—(C$_2$-C$_6$-alkyl)-N(R$^5$)$_2$;
R$^3$ is halogen or C$_1$-C$_2$-haloalkyl;
R$^4$ is halogen or C$_1$-C$_2$-haloalkyl; and
R$^5$ is independently H or C$_1$-C$_4$-alkyl; or a pharmaceutically acceptable salt thereof.

In some embodiments, X is NH or —N(CH$_3$)—;
R$^1$ is OH, C$_1$-C$_6$-alkyl, C$_1$-C$_6$-haloalkyl, —O—(C$_1$-C$_6$-alkyl), or —O—(C$_1$-C$_6$-haloalkyl);
R$^2$ is OH, —O—(C$_2$-C$_6$-alkyl)-N(R$^5$)$_2$, —O—(C$_2$-C$_6$-alkyl)-N(R$^5$)$_3$$^+$halogen$^-$, —N(R$^5$)—(C$_2$-C$_6$-alkyl)-N(R$^5$)$_2$, or —O—(C$_1$-C$_6$-alkyl)-phenyl; wherein when R$^1$ is OH, R$^2$ is OH, —O—($C_1$-$C_6$-alkyl)-phenyl, or —O—($C_2$-$C_6$-alkyl)-N($R^5$)$_3$$^+$halogen$^-$; when $R^1$ is $C_1$-$C_6$-alkyl or —O—($C_1$-$C_6$-alkyl), $R^2$ is —O—($C_1$-$C_6$-alkyl)-phenyl or —O—($C_2$-$C_6$-alkyl)-N($R^5$)$_3$$^+$halogen$^-$; and wherein $R^1$ and $R^2$ are not both H; or $R^2$ and X together with the atoms to which they are attached form

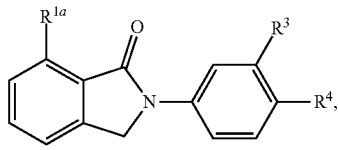

wherein $R^{1a}$ is OH; or $R^2$ and X together with the atoms to which they are attached form

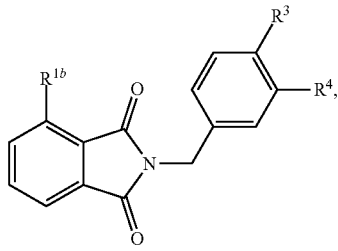

wherein $R^{1b}$ is OH, O—($C_1$-$C_6$-alkyl), or —O—($C_2$-$C_6$-alkyl)-N($R^5$)$_2$;

$R^3$ is halogen or $C_1$-$C_2$-haloalkyl;

$R^4$ is halogen or $C_1$-$C_2$-haloalkyl; and $R^5$ is independently H or $C_1$-$C_4$-alkyl; or a pharmaceutically acceptable salt thereof.

In some embodiments, X is NH or —N(CH$_3$)—;

$R^1$ is H, OH, $C_1$-$C_6$-alkyl, $C_1$-$C_6$-haloalkyl, —O—($C_1$-$C_6$-alkyl), or —O—($C_1$-$C_6$-haloalkyl);

$R^2$ is H, OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH or $C_1$-$C_6$-alkyl, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is H, $R^2$ is —N($R^5$)—($C_2$-$C_6$-alkyl)-N($R^5$)$_2$; and wherein $R^1$ and $R^2$ are not both H; or $R^2$ and X together with the atoms to which they are attached form

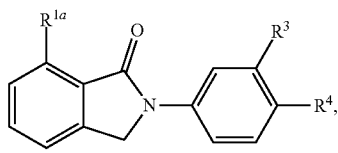

wherein $R^{1a}$ is OH or OCH$_3$; or $R^2$ and X together with the atoms to which they are attached form

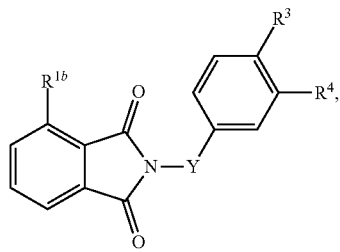

wherein Y is —($C_1$-$C_2$-alkyl);

$R^{1b}$ is OH, O—($C_1$-$C_6$-alkyl), or —O—($C_2$-$C_6$-alkyl)-N($R^5$)$_2$;

$R^3$ is halogen or $C_1$-$C_2$-haloalkyl;

$R^4$ is halogen or $C_1$-$C_2$-haloalkyl; and $R^5$ is independently H or $C_1$-$C_4$-alkyl; or a pharmaceutically acceptable salt thereof.

In some embodiments, X is NH or —N(CH$_3$)—;

$R^1$ is OH, $C_1$-$C_6$-alkyl, $C_1$-$C_6$-haloalkyl, —O—($C_1$-$C_6$-alkyl), or —O—($C_1$-$C_6$-haloalkyl);

$R^2$ is OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH or $C_1$-$C_6$-alkyl, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is $C_1$-$C_6$-alkyl or —O—($C_1$-$C_6$-alkyl), $R^2$ is —O—($C_1$-$C_6$-alkyl)-phenyl or —O—($C_2$-$C_6$-alkyl)-N($R^5$)$_3$$^+$halogen$^-$; and wherein $R^1$ and $R^2$ are not both H; or $R^2$ and X together with the atoms to which they are attached form

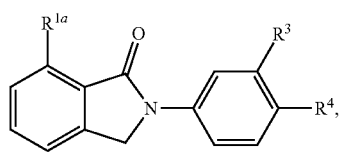

wherein $R^{1a}$ is OH; or $R^2$ and X together with the atoms to which they are attached form

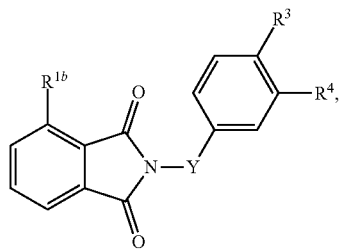

wherein Y is —($C_1$-$C_2$-alkyl);

$R^{1b}$ is OH, O—($C_1$-$C_6$-alkyl), or —O—($C_2$-$C_6$-alkyl)-N($R^5$)$_2$;

$R^3$ is halogen or $C_1$-$C_2$-haloalkyl;

$R^4$ is halogen or $C_1$-$C_2$-haloalkyl; and $R^5$ is independently H or $C_1$-$C_4$-alkyl; or a pharmaceutically acceptable salt thereof.

In some embodiments, X is NH or —N(CH$_3$)—;

$R^1$ is H, OH, $C_1$-$C_3$-alkyl, $C_1$-$C_3$-haloalkyl, —O—($C_1$-$C_3$-alkyl), or —O—($C_1$-$C_3$-haloalkyl);

$R^2$ is H, OH, —O—($C_2$-$C_4$-alkyl)-N($R^5$)$_2$, —O—($C_2$-$C_4$-alkyl)-N($R^5$)$_3{}^+$halogen$^-$, —N($R^5$)—($C_2$-$C_4$-alkyl)-N($R^5$)$_2$, or —O—($C_1$-$C_4$-alkyl)-phenyl; wherein when $R^1$ is OH or $C_1$-$C_3$-alkyl, $R^2$ is OH, —O—($C_1$-$C_4$-alkyl)-phenyl, or —O—($C_2$-$C_4$-alkyl)-N($R^5$)$_3{}^+$halogen$^-$; when $R^1$ is H, $R^2$ is —N($R^5$)—($C_2$-$C_4$-alkyl)-N($R^5$)$_2$; and wherein $R^1$ and $R^2$ are not both H; or $R^2$ and X together with the atoms to which they are attached form

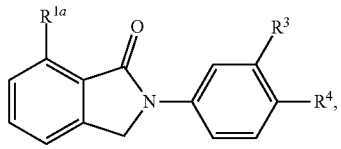

wherein $R^{1a}$ is OH or OCH$_3$; or $R^2$ and X together with the atoms to which they are attached form

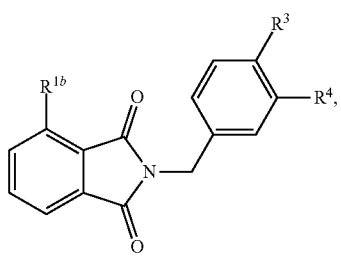

wherein $R^{1b}$ is OH, O—($C_1$-$C_3$-alkyl), or —O—($C_2$-$C_4$-alkyl)-N($R^5$)$_2$;

$R^3$ is halogen or $C_1$-$C_2$-haloalkyl;

$R^4$ is halogen or $C_1$-$C_2$-haloalkyl; and $R^5$ is independently H or $C_1$-$C_4$-alkyl; or a pharmaceutically acceptable salt thereof.

In some embodiments, X is NH or —N(CH$_3$)—;

$R^1$ is OH, $C_1$-$C_3$-alkyl, $C_1$-$C_3$-haloalkyl, —O—($C_1$-$C_3$-alkyl), or —O—($C_1$-$C_3$-haloalkyl);

$R^2$ is OH, —O—($C_2$-$C_4$-alkyl)-N($R^5$)$_2$, —O—($C_2$-$C_4$-alkyl)-N($R^5$)$_3{}^+$halogen$^-$, —N($R^5$)—($C_2$-$C_4$-alkyl)-N($R^5$)$_2$, or —O—($C_1$-$C_4$-alkyl)-phenyl; wherein when $R^1$ is OH, $R^2$ is OH, —O—($C_1$-$C_4$-alkyl)-phenyl, or —O—($C_2$-$C_4$-alkyl)-N($R^5$)$_3{}^+$halogen$^-$; when $R^1$ is $C_1$-$C_3$-alkyl or O—($C_1$-$C_3$-alkyl), $R^2$ is —O—($C_1$-$C_4$-alkyl)-phenyl or —O—($C_2$-$C_4$-alkyl)-N($R^5$)$_3{}^+$halogen$^-$; and wherein $R^1$ and $R^2$ are not both H; or $R^2$ and X together with the atoms to which they are attached form

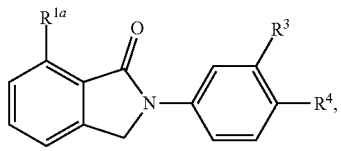

wherein $R^{1a}$ is OH; or $R^2$ and X together with the atoms to which they are attached form

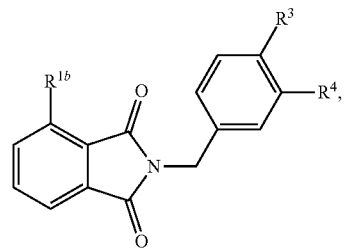

wherein $R^{1b}$ is OH, O—($C_1$-$C_3$-alkyl), or —O—($C_2$-$C_4$-alkyl)-N($R^5$)$_2$;

$R^3$ is halogen or $C_1$-$C_2$-haloalkyl;

$R^4$ is halogen or $C_1$-$C_2$-haloalkyl; and $R^5$ is independently H or $C_1$-$C_4$-alkyl; or a pharmaceutically acceptable salt thereof.

In some embodiments, X is NH or —N(CH$_3$)—;

$R^1$ is H, OH, $C_1$-$C_3$-alkyl, $C_1$-$C_3$-haloalkyl, —O—($C_1$-$C_3$-alkyl), or —O—($C_1$-$C_3$-haloalkyl);

$R^2$ is H, OH, —O—($C_2$-$C_4$-alkyl)-N($R^5$)$_2$, —O—($C_2$-$C_4$-alkyl)-N($R^5$)$_3{}^+$halogen$^-$, —N($R^5$)—($C_2$-$C_4$-alkyl)-N($R^5$)$_2$, or —O—($C_1$-$C_4$-alkyl)-phenyl; wherein when $R^1$ is OH or $C_1$-$C_3$-alkyl, $R^2$ is OH, —O—($C_1$-$C_4$-alkyl)-phenyl, or —O—($C_2$-$C_4$-alkyl)-N($R^5$)$_3{}^+$halogen$^-$; when $R^1$ is H, $R^2$ is —N($R^5$)—($C_2$-$C_4$-alkyl)-N($R^5$)$_2$; and wherein $R^1$ and $R^2$ are not both H; or $R^2$ and X together with the atoms to which they are attached form

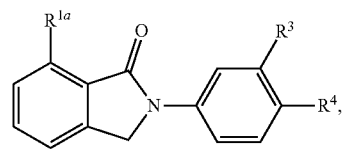

wherein $R^{1a}$ is OH or OCH$_3$; or $R^2$ and X together with the atoms to which they are attached form

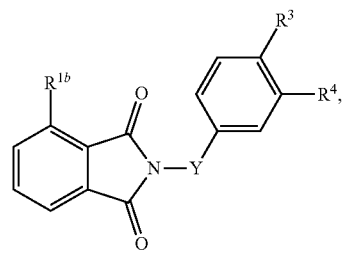

wherein Y is —($C_1$-$C_2$-alkyl);

$R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3{}^+$halogen$^-$;

$R^3$ is halogen or $C_1$-$C_2$-haloalkyl;

$R^4$ is halogen or $C_1$-$C_2$-haloalkyl; and $R^5$ is independently H or $C_1$-$C_4$-alkyl; or $R^2$ and X together with the atoms to which they are attached form

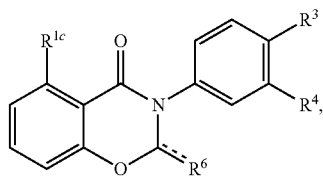

wherein
$R^{1c}$ is OH, O—($C_1$-$C_6$-alkyl), O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl;
$R^5$ is independently H or $C_1$-$C_4$-alkyl; and
==== is a double bond and $R^6$ is O, or
==== is a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3$$^+$halogen$^-$; or a pharmaceutically acceptable salt thereof.

In some embodiments, X is NH or —N(CH$_3$)—;
$R^1$ is OH, $C_1$-$C_3$-alkyl, $C_1$-$C_3$-haloalkyl, —O—($C_1$-$C_3$-alkyl), or —O—($C_1$-$C_3$-haloalkyl);
$R^2$ is OH, —O—($C_2$-$C_4$-alkyl)-N($R^5$)$_2$, —O—($C_2$-$C_4$-alkyl)-N($R^5$)$_3$$^+$halogen$^-$, —N($R^5$)—($C_2$-$C_4$-alkyl)-N($R^5$)$_2$, or —O—($C_1$-$C_4$-alkyl)-phenyl; wherein when $R^1$ is OH, $R^2$ is OH, —O—($C_1$-$C_4$-alkyl)-phenyl, or —O—($C_2$-$C_4$-alkyl)-N($R^5$)$_3$$^+$halogen$^-$; when $R^1$ is $C_1$-$C_3$-alkyl or —O—($C_1$-$C_3$-alkyl), $R^2$ is —O—($C_1$-$C_4$-alkyl)-phenyl or —O—($C_2$-$C_4$-alkyl)-N($R^5$)$_3$$^+$halogen$^-$; and wherein $R^1$ and $R^2$ are not both H; or
$R^2$ and X together with the atoms to which they are attached form

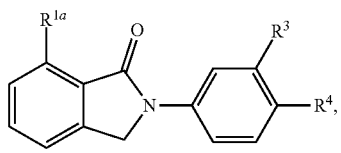

wherein $R^{1a}$ is OH; or
$R^2$ and X together with the atoms to which they are attached form

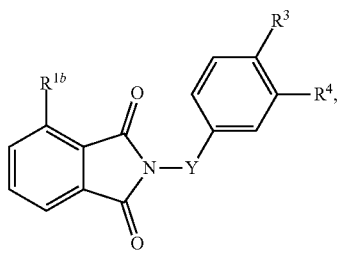

wherein Y is —($C_1$-$C_2$-alkyl);
$R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or
$R^2$ and X together with the atoms to which they are attached form

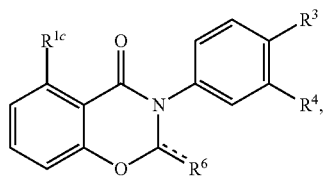

wherein
$R^{1c}$ is OH, O—($C_1$-$C_6$-alkyl), O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl;
$R^5$ is independently H or $C_1$-$C_4$-alkyl; and
==== is a double bond and $R^6$ is O, or
==== is a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3$$^+$halogen$^-$; or a pharmaceutically acceptable salt thereof.

In some embodiments, X is NH or —N(CH$_3$)—;
$R^1$ is H, OH, $C_1$-$C_3$-alkyl, $C_1$-$C_3$-haloalkyl, —O—($C_1$-$C_3$-alkyl), or —O—($C_1$-$C_3$-haloalkyl);
$R^2$ is H, OH, —O—($C_2$-$C_4$-alkyl)-N($R^5$)$_2$, —O—($C_2$-$C_4$-alkyl)-N($R^5$)$_3$$^+$halogen$^-$, —N($R^5$)—($C_2$-$C_4$-alkyl)-N($R^5$)$_2$, or —O—($C_1$-$C_4$-alkyl)-phenyl; wherein when $R^1$ is OH or $C_1$-$C_3$-alkyl, $R^2$ is OH, —O—($C_1$-$C_4$-alkyl)-phenyl, or —O—($C_2$-$C_4$-alkyl)-N($R^5$)$_3$$^+$halogen$^-$; when $R^1$ is H, $R^2$ is —N($R^5$)—($C_2$-$C_4$-alkyl)-N($R^5$)$_2$; and wherein $R^1$ and $R^2$ are not both H; or
$R^2$ and X together with the atoms to which they are attached form

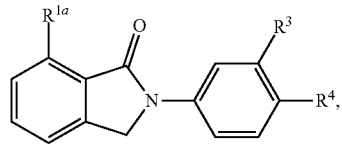

wherein $R^{1a}$ is OH or OCH$_3$; or
$R^2$ and X together with the atoms to which they are attached form

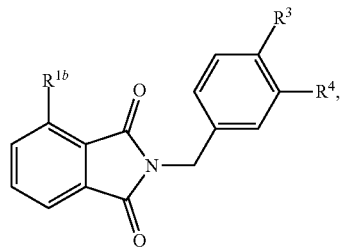

wherein $R^{1b}$ is OH, O—($C_1$-$C_3$-alkyl), or O—($C_2$-$C_4$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is OH, $C_1$-$C_3$-alkyl, $C_1$-$C_3$-haloalkyl, —O—($C_1$-$C_3$-alkyl), or —O—($C_1$-$C_3$-haloalkyl);
$R^2$ is OH, —O—($C_2$-$C_4$-alkyl)-N($R^5$)$_2$, —O—($C_2$-$C_4$-alkyl)-N($R^5$)$_3$$^+$halogen$^-$, —N($R^5$)—($C_2$-$C_4$-alkyl)-N($R^5$)$_2$, or —O—($C_1$-$C_4$-alkyl)-phenyl; wherein when $R^1$ is OH, $R^2$ is OH, —O—($C_1$-$C_4$-alkyl)-phenyl, or —O—($C_2$-$C_4$-alkyl)-N($R^5$)$_3$$^+$halogen$^-$; when $R^1$ is $C_1$-$C_3$-alkyl or —O—($C_1$-$C_3$-alkyl), $R^2$ is —O—($C_1$-$C_4$-alkyl)-phenyl or —O—($C_2$-$C_4$-alkyl)-N($R^5$)$_3$$^+$halogen$^-$; and wherein $R^1$ and $R^2$ are not both H; or $R^2$ and X together with the atoms to which they are attached form

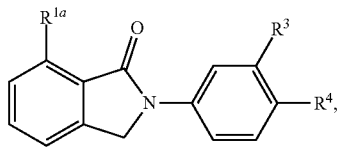

wherein $R^{1a}$ is OH; or
$R^2$ and X together with the atoms to which they are attached form

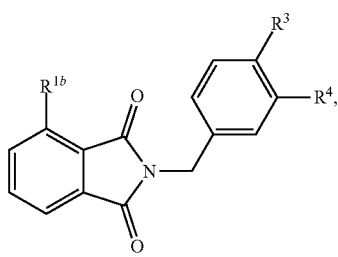

wherein $R^{1b}$ is OH, O—($C_1$-$C_3$-alkyl), or —O—($C_2$-$C_4$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
R is H, OH, $C_1$-$C_6$-alkyl, $C_1$-$C_6$-haloalkyl, —O—($C_1$-$C_6$-alkyl), or —O—($C_1$-$C_6$-haloalkyl);
$R^2$ is H, OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH or $C_1$-$C_6$-alkyl, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is H, $R^2$ is —N($R^5$)—($C_2$-$C_6$-alkyl)-N($R^5$)$_2$; and wherein $R^1$ and $R^2$ are not both H;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is OH, $C_1$-$C_6$-alkyl, $C_1$-$C_6$-haloalkyl, —O—($C_1$-$C_6$-alkyl), or —O—($C_1$-$C_6$-haloalkyl);
$R^2$ is OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is $C_1$-$C_6$-alkyl or —O—($C_1$-$C_6$-alkyl), $R^2$ is —O—($C_1$-$C_6$-alkyl)-phenyl or —O—($C_2$-$C_6$-alkyl)-N($R^5$)$_3$$^+$halogen$^-$; and wherein $R^1$ and $R^2$ are not both H;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments,
$R^2$ and X together with the atoms to which they are attached form

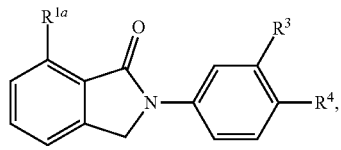

wherein $R^{1a}$ is OH or OCH$_3$; or
$R^2$ and X together with the atoms to which they are attached form

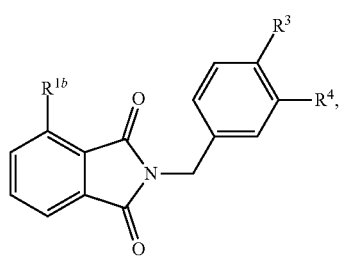

wherein $R^{1b}$ is OH, O—($C_1$-$C_6$-alkyl), or —O—($C_2$-$C_6$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments,
$R^2$ and X together with the atoms to which they are attached form

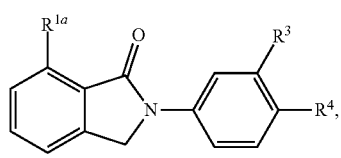

wherein $R^{1a}$ is OH; or
$R^2$ and X together with the atoms to which they are attached form

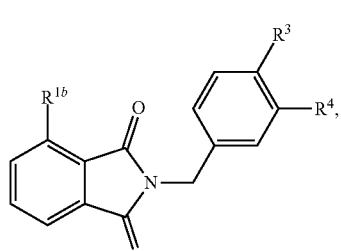

wherein $R^{1b}$ is OH, O—($C_1$-$C_6$-alkyl), or —O—($C_2$-$C_6$-alkyl)-N($R^5$)$_2$;

$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, $R^2$ and X together with the atoms to which they are attached form

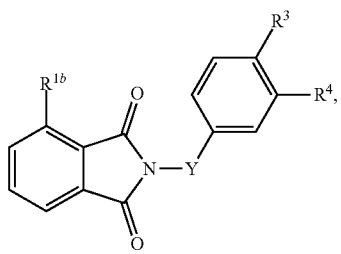

wherein Y is —($C_1$-$C_6$-alkyl); $R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$; $R^3$ is halogen or $C_1$-$C_2$-haloalkyl; and $R^4$ is halogen or $C_1$-$C_2$-haloalkyl; or a pharmaceutically acceptable salt thereof.

In some embodiments, the compound of formula (I) is a compound of formula (Ia) or (Ib):

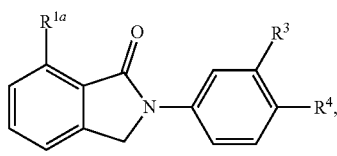 (Ia)

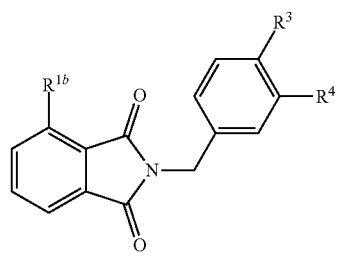 (Ib)

wherein $R^{1a}$ is OH or OCH$_3$;
$R^{1b}$ is OH, O—($C_1$-$C_6$-alkyl), or —O—($C_2$-$C_6$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, the compound of formula (I) is a compound of formula (Ia) or (Ib):

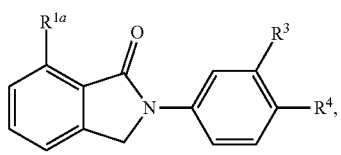 (Ia)

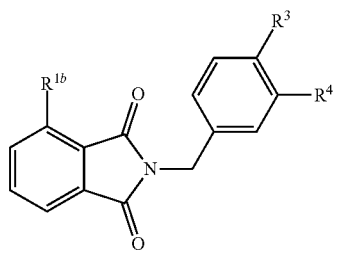 (Ib)

wherein $R^{1a}$ is OH;
$R^{1b}$ is OH, O—($C_1$-$C_6$-alkyl), or —O—($C_2$-$C_6$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is H, OH, halogen, or $C_1$-$C_6$-alkyl;
$R^2$ is OH, halogen, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH or $C_1$-$C_6$-alkyl, $R^2$ is OH, —O—($C_1$-$C_6$-alkyl)-phenyl, or —O—($C_2$-$C_6$-alkyl)-N($R^5$)$_3$$^+$halogen$^-$; when $R^1$ is H, $R^2$ is —N($R^5$)—($C_2$-$C_6$-alkyl)-N($R^5$)$_2$; or $R^2$ and X together with the atoms to which they are attached form

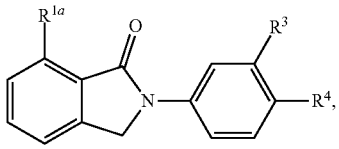

wherein $R^{1a}$ is OH or OCH$_3$; or
$R^2$ and X together with the atoms to which they are attached form

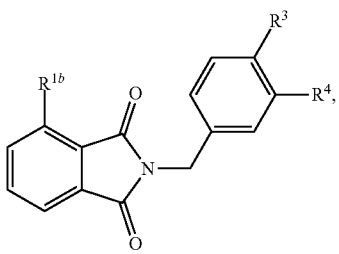

wherein $R^{1b}$ is OH, O—($C_1$-$C_6$-alkyl), or —O—($C_2$-$C_6$-alkyl)-N($R^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is OH, halogen, or $C_1$-$C_6$-alkyl;
$R^2$ is OH, halogen, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl; wherein when $R^1$ is OH, $R^2$ is OH, —O—($C_1$-$C_6$-alkyl)-phenyl, or —O—($C_2$-$C_6$-alkyl)-N($R^5$)$_3$$^+$halogen$^-$;

when R$^1$ is C$_1$-C$_6$-alkyl, R$^2$ is —O—(C$_1$-C$_6$-alkyl)-phenyl or —O—(C$_2$-C$_6$-alkyl)-N(R$^5$)$_3$$^+$halogen$^-$; or R$^2$ and X together with the atoms to which they are attached form

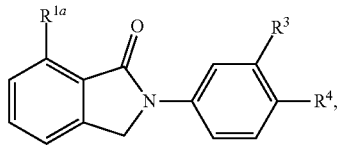

wherein R$^{1a}$ is OH; or

R$^2$ and X together with the atoms to which they are attached form

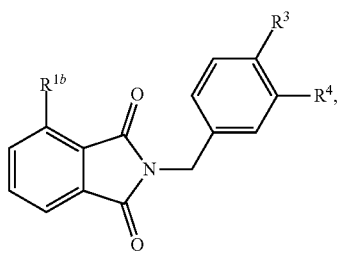

wherein R$^{1b}$ is OH, O—(C$_1$-C$_6$-alkyl), or —O—(C$_2$-C$_6$-alkyl)-N(R$^5$)$_2$;
R$^3$ is halogen or C$_1$-C$_2$-haloalkyl;
R$^4$ is halogen or C$_1$-C$_2$-haloalkyl; and
R$^5$ is independently H or C$_1$-C$_4$-alkyl; or a pharmaceutically acceptable salt thereof.

In some embodiments, X is NH or —N(CH$_3$)—;
R$^1$ is H, OH, or C$_1$-C$_6$-alkyl;
R$^2$ is OH, —O—(C$_2$-C$_6$-alkyl)-N(R$^5$)$_3$$^+$halogen$^-$, —N(R$^5$)—(C$_2$-C$_6$-alkyl)-N(R$^5$)$_2$, or —O—(C$_1$-C$_6$-alkyl)-phenyl; wherein when R$^1$ is OH or C$_1$-C$_6$-alkyl, R$^2$ is OH, —O—(C$_1$-C$_6$-alkyl)-phenyl, or —O—(C$_2$-C$_6$-alkyl)-N(R$^5$)$_3$$^+$halogen$^-$; when R$^1$ is H, R$^2$ is —N(R$^5$)—(C$_2$-C$_6$-alkyl)-N(R$^5$)$_2$; or R$^2$ and X together with the atoms to which they are attached form

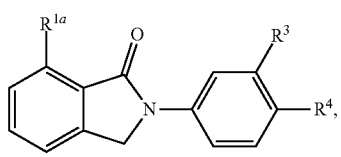

wherein R$^{1a}$ is OH or OCH$_3$; or

R$^2$ and X together with the atoms to which they are attached form

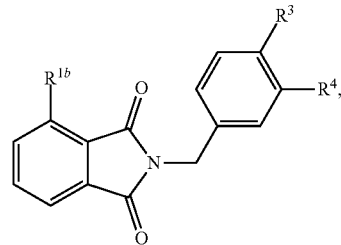

wherein R$^{1b}$ is OH, O—(C$_1$-C$_6$-alkyl), or —O—(C$_2$-C$_6$-alkyl)-N(R$^5$)$_2$;
R$^3$ is halogen or C$_1$-C$_2$-haloalkyl;
R$^4$ is halogen or C$_1$-C$_2$-haloalkyl; and
R$^5$ is independently H or C$_1$-C$_4$-alkyl; or a pharmaceutically acceptable salt thereof.

In some embodiments, X is NH or —N(CH$_3$)—;
R$^1$ is OH or C$_1$-C$_6$-alkyl;
R$^2$ is OH, —O—(C$_2$-C$_6$-alkyl)-N(R$^5$)$_3$$^+$halogen$^-$, —N(R$^5$)—(C$_2$-C$_6$-alkyl)-N(R$^5$)$_2$, or —O—(C$_1$-C$_6$-alkyl)-phenyl; wherein when R$^1$ is OH, R$^2$ is OH, —O—(C$_1$-C$_6$-alkyl)-phenyl, or —O—(C$_2$-C$_6$-alkyl)-N(R$^5$)$_3$$^+$halogen$^-$;
when R$^1$ is C$_1$-C$_6$-alkyl, R$^2$ is —O—(C$_1$-C$_6$-alkyl)-phenyl or —O—(C$_2$-C$_6$-alkyl)-N(R$^5$)$_3$$^+$halogen$^-$; or R$^2$ and X together with the atoms to which they are attached form

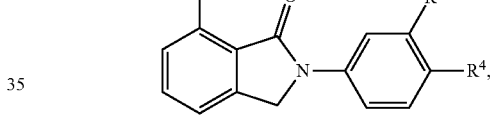

wherein R$^{1a}$ is OH; or

R$^2$ and X together with the atoms to which they are attached form

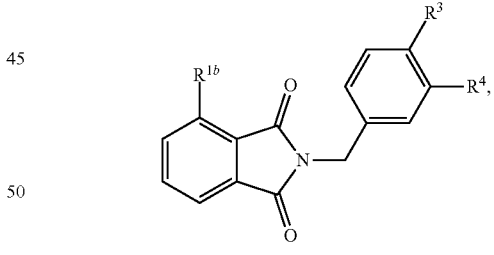

wherein R$^{1b}$ is OH, O—(C$_1$-C$_6$-alkyl), or —O—(C$_2$-C$_6$-alkyl)-N(R$^5$)$_2$;
R$^3$ is halogen or C$_1$-C$_2$-haloalkyl;
R$^4$ is halogen or C$_1$-C$_2$-haloalkyl; and
R$^5$ is independently H or C$_1$-C$_4$-alkyl; or a pharmaceutically acceptable salt thereof.

In some embodiments, X is NH or —N(CH$_3$)—;
R$^1$ is H, OH, or C$_1$-C$_6$-alkyl;
R$^2$ is OH, —O—(C$_2$-C$_6$-alkyl)-N(R$^5$)$_3$$^+$halogen$^-$, —N(R$^5$)—(C$_2$-C$_6$-alkyl)-N(R$^5$)$_2$, or —O—(C$_1$-C$_6$-alkyl)-phenyl; wherein when R$^1$ is OH or C$_1$-C$_6$-alkyl, R$^2$ is OH, —O—(C$_1$-C$_6$-alkyl)-phenyl, or —O—(C$_2$-C$_6$-alkyl)-N(R$^5$)$_3$$^+$halogen$^-$; when R$^1$ is H, R$^2$ is —N(R$^5$)—(C$_2$-C$_6$-alkyl)-N(R$^5$)$_2$;

$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is OH or $C_1$-$C_6$-alkyl;
$R^2$ is OH, —O—(C$_2$-C$_6$-alkyl)-N(R$^5$)$_3^+$halogen$^-$, —N(R$^5$)—(C$_2$-C$_6$-alkyl)-N(R$^5$)$_2$, or —O—(C$_1$-C$_6$-alkyl)-phenyl; wherein when $R^1$ is OH, $R^2$ is OH, —O—(C$_1$-C$_6$-alkyl)-phenyl, or —O—(C$_2$-C$_6$-alkyl)-N(R$^5$)$_3^+$halogen$^-$; when $R^1$ is $C_1$-$C_6$-alkyl, $R^2$ is —O—(C$_1$-C$_6$-alkyl)-phenyl or —O—(C$_2$-C$_6$-alkyl)-N(R$^5$)$_3^+$halogen$^-$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is H, OH, or $C_1$-$C_6$-alkyl;
$R^2$ is OH, —N(R$^5$)—(C$_2$-C$_6$-alkyl)-N(R$^5$)$_2$, or —O—(C$_1$-C$_6$-alkyl)-phenyl; wherein when $R^1$ is OH or $C_1$-$C_6$-alkyl, $R^2$ is OH, or —O—(C$_1$-C$_6$-alkyl)-phenyl; when $R^1$ is H, $R^2$ is —N(R$^5$)—(C$_2$-C$_6$-alkyl)-N(R$^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or —N(CH$_3$)—;
$R^1$ is OH or $C_1$-$C_6$-alkyl;
$R^2$ is OH, —N(R$^5$)—(C$_2$-C$_6$-alkyl)-N(R$^5$)$_2$, or —O—(C$_1$-C$_6$-alkyl)-phenyl; wherein when $R^1$ is OH, $R^2$ is OH or —O—(C$_1$-C$_6$-alkyl)-phenyl; when $R^1$ is $C_1$-$C_6$-alkyl, $R^2$ is —O—(C$_1$-C$_6$-alkyl)-phenyl;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH;
$R^1$ is H, OH, or $C_1$-$C_6$-alkyl;
$R^2$ is OH, —N(R$^5$)—(C$_2$-C$_6$-alkyl)-N(R$^5$)$_2$, or —O—(C$_1$-C$_6$-alkyl)-phenyl; wherein when $R^1$ is OH or $C_1$-$C_6$-alkyl, $R^2$ is OH, or —O—(C$_1$-C$_6$-alkyl)-phenyl; when $R^1$ is H, $R^2$ is —N(R$^5$)—(C$_2$-C$_6$-alkyl)-N(R$^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH;
$R^1$ is OH or $C_1$-$C_6$-alkyl;
$R^2$ is OH, —N(R$^5$)—(C$_2$-C$_6$-alkyl)-N(R$^5$)$_2$, or —O—(C$_1$-C$_6$-alkyl)-phenyl; wherein when $R^1$ is OH, $R^2$ is OH or —O—(C$_1$-C$_6$-alkyl)-phenyl; when $R^1$ is $C_1$-$C_6$-alkyl, $R^2$ is —O—(C$_1$-C$_6$-alkyl)-phenyl;
$R^3$ is halogen or $C_1$-$C_2$-haloalkyl;
$R^4$ is halogen or $C_1$-$C_2$-haloalkyl; and
$R^5$ is independently H or $C_1$-$C_4$-alkyl; or a pharmaceutically acceptable salt thereof.

In some embodiments, X is NH or N(CH$_3$);
$R^1$ is H, OH, or $C_1$-$C_2$-alkyl;
$R^2$ is OH, —N(R$^5$)—(C$_2$-C$_3$-alkyl)-N(R$^5$)$_2$, or —O—(C$_1$-C$_3$-alkyl)-phenyl; wherein when $R^1$ is OH or $C_1$-$C_2$-alkyl, $R^2$ is OH, or —O—(C$_1$-C$_3$-alkyl)-phenyl; when $R^1$ is H, $R^2$ is —N(R$^5$)—(C$_2$-C$_3$-alkyl)-N(R$^5$)$_2$;
$R^3$ is halogen or $C_1$-$C_2$-haloalkyl;
$R^4$ is halogen or $C_1$-$C_2$-haloalkyl; and
$R^5$ is independently H or $C_1$-$C_2$-alkyl; or a pharmaceutically acceptable salt thereof.

In some embodiments, X is NH or N(CH$_3$);
$R^1$ is OH or $C_1$-$C_2$-alkyl;
$R^2$ is OH, —N(R$^5$)—(C$_2$-C$_3$-alkyl)-N(R$^5$)$_2$, or —O—(C$_1$-C$_3$-alkyl)-phenyl; wherein when $R^1$ is OH, $R^2$ is OH or —O—(C$_1$-C$_3$-alkyl)-phenyl; when $R^1$ is $C_1$-$C_2$-alkyl, $R^2$ is —O—(C$_1$-C$_3$-alkyl)-phenyl;
$R^3$ is halogen or $C_1$-$C_2$-haloalkyl;
$R^4$ is halogen or $C_1$-$C_2$-haloalkyl; and
$R^5$ is independently H or $C_1$-$C_2$-alkyl; or a pharmaceutically acceptable salt thereof.

In some embodiments, X is NH or —N(CH$_3$)—. In some embodiments, X is NH. In some embodiments, X is —N(CH$_3$)—.

In some embodiments, $R^1$ is H, OH, halogen, $C_1$-$C_6$-alkyl, $C_1$-$C_6$-haloalkyl, —O—(C$_1$-C$_6$-alkyl), or —O—(C$_1$-C$_6$-haloalkyl). In some embodiments, $R^1$ is H, OH, $C_1$-$C_6$-alkyl, $C_1$-$C_6$-haloalkyl, —O—(C$_1$-C$_6$-alkyl), or —O—(C$_1$-C$_6$-haloalkyl). In some embodiments, $R^1$ is H, OH, $C_1$-$C_4$-alkyl, $C_1$-$C_4$-haloalkyl, —O—(C$_1$-C$_4$-alkyl), or —O—(C$_1$-C$_4$-haloalkyl). In some embodiments, $R^1$ is OH, $C_1$-$C_6$-alkyl, or —O—(C$_1$-C$_6$-alkyl). In some embodiments, $R^1$ is OH, $C_1$-$C_2$-alkyl, or —O—(C$_1$-C$_2$-alkyl). In some embodiments, $R^1$ is H, OH, $C_1$-$C_2$-alkyl, $C_1$-$C_2$-haloalkyl, —O—(C$_1$-C$_2$-alkyl), or —O—(C$_1$-C$_2$-haloalkyl). In some embodiments, $R^1$ is H, OH, or $C_1$-$C_6$-alkyl. In some embodiments, $R^1$ is H, OH, or $C_1$-$C_2$-alkyl. In some embodiments, $R^1$ is OH, or $C_1$-$C_6$-alkyl. In some embodiments, $R^1$ is OH, or $C_1$-$C_2$-alkyl. In some embodiments, $R^1$ is $C_1$-$C_6$-alkyl. In some embodiments, $R^1$ is $C_1$-$C_2$-alkyl.

In some embodiments, $R^1$ is OH, halogen, $C_1$-$C_6$-alkyl, $C_1$-$C_6$-haloalkyl, —O—(C$_1$-C$_6$-alkyl), or —O—(C$_1$-C$_6$-haloalkyl). In some embodiments, $R^1$ is OH, $C_1$-$C_6$-alkyl, $C_1$-$C_6$-haloalkyl, —O—(C$_1$-C$_6$-alkyl), or —O—(C$_1$-C$_6$-haloalkyl). In some embodiments, $R^1$ is OH, $C_1$-$C_4$-alkyl, $C_1$-$C_4$-haloalkyl, —O—(C$_1$-C$_4$-alkyl), or —O—(C$_1$-C$_4$-haloalkyl). In some embodiments, $R^1$ is OH, $C_1$-$C_6$-alkyl, or —O—(C$_1$-C$_6$-alkyl). In some embodiments, $R^1$ is OH, $C_1$-$C_2$-alkyl, or —O—(C$_1$-C$_2$-alkyl). In some embodiments, $R^1$ is OH, $C_1$-$C_2$-alkyl, $C_1$-$C_2$-haloalkyl, —O—(C$_1$-C$_2$-alkyl), or —O—(C$_1$-C$_2$-haloalkyl). In some embodiments, $R^1$ is OH or $C_1$-$C_6$-alkyl. In some embodiments, $R^1$ is OH or $C_1$-$C_2$-alkyl. In some embodiments, $R^1$ is $C_1$-$C_6$-alkyl. In some embodiments, $R^1$ is $C_1$-$C_2$-alkyl.

In some embodiments, $R^2$ is H, OH, halogen, —O—(C$_2$-C$_6$-alkyl)-N(R$^5$)$_2$, —O—(C$_2$-C$_6$-alkyl)-N(R$^5$)$_3^+$halogen$^-$, —N(R$^5$)—(C$_2$-C$_6$-alkyl)-N(R$^5$)$_2$, or —O—(C$_1$-C$_6$-alkyl)-phenyl. In some embodiments, $R^2$ is H, OH, —O—(C$_2$-C$_6$-alkyl)-N(R$^5$)$_2$, —O—(C$_2$-C$_6$-alkyl)-N(R$^5$)$_3^+$halogen$^-$, —N(R$^5$)—(C$_2$-C$_6$-alkyl)-N(R$^5$)$_2$, or —O—(C$_1$-C$_6$-alkyl)-phenyl. In some embodiments, $R^2$ is OH, —O—(C$_2$-C$_6$-alkyl)-N(R$^5$)$_2$, —O—(C$_2$-C$_6$-alkyl)-N(R$^5$)$_3^+$halogen$^-$, —N(R$^5$)—(C$_2$-C$_6$-alkyl)-N(R$^5$)$_2$, or —O—(C$_1$-C$_6$-alkyl)-phenyl. In some embodiments, $R^2$ is OH, —O—(C$_2$-C$_6$-alkyl)-N(R$^5$)$_3^+$halogen$^-$, —N(R$^5$)—(C$_2$-C$_6$-alkyl)-N(R$^5$)$_2$, or —O—(C$_1$-C$_6$-alkyl)-phenyl. In some embodiments, $R^2$ is H, OH, —O—(C$_2$-C$_4$-alkyl)-N(R$^5$)$_2$, —O—(C$_2$-C$_4$-alkyl)-N(R$^5$)$_3^+$halogen$^-$, —N(R$^5$)—(C$_2$-C$_4$-alkyl)-N(R$^5$)$_2$, or —O—(C$_1$-C$_4$-alkyl)-phenyl. In some embodiments, $R^2$ is OH, —N(R$^5$)—(C$_2$-C$_3$-alkyl)-N(R$^5$)$_2$, or —O—(C$_1$-C$_3$-alkyl)-phenyl. In some embodiments, $R^2$ is —N(R$^5$)—(C$_2$-C$_6$-alkyl)-N(R$^5$)$_2$, or —O—(C$_1$-C$_6$-alkyl)-phenyl. In some embodiments, $R^2$ is —N(R$^5$)—(C$_2$-C$_3$-alkyl)-N(R$^5$)$_2$, or —O—(C$_1$-C$_3$-alkyl)-phenyl. In some embodiments, $R^2$ is —N(R$^5$)—(C$_2$-C$_3$-alkyl)-N(R$^5$)$_2$, or —O—(C$_1$-C$_3$-alkyl)-phenyl. In some embodiments, $R^2$ is —N(R$^5$)—(C$_2$-C$_3$-alkyl)-N(R$^5$)$_2$. In some embodiments, $R^2$ is —O—(C$_1$-C$_3$-alkyl)-phenyl.

In some embodiments, $R^2$ is OH, halogen, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl. In some embodiments, $R^2$ is OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl. In some embodiments, $R^2$ is OH, —O—($C_2$-$C_6$-alkyl)-N($R^5$)$_2$, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl. In some embodiments, $R^2$ is OH, —O—($C_2$-$C_6$-alkyl)-N($R^5$)$_3$$^+$halogen$^-$, —N($R^5$)—($C_2$-$C_6$-alkyl)-N($R^5$)$_2$, or —O—($C_1$-$C_6$-alkyl)-phenyl. In some embodiments, $R^2$ is OH, —O—($C_2$-$C_4$-alkyl)-N($R^5$)$_2$, —O—($C_2$-$C_4$-alkyl)-N($R^5$)$_3$$^+$halogen$^-$, —N($R^5$)—($C_2$-$C_4$-alkyl)-N($R^5$)$_2$, or —O—($C_1$-$C_4$-alkyl)-phenyl. In some embodiments, $R^2$ is OH, —N($R^5$)—($C_2$-$C_3$-alkyl)-N($R^5$)$_2$, or —O—($C_1$-$C_3$-alkyl)-phenyl. In some embodiments, $R^2$ is —N($R^5$)—($C_2$-$C_6$-alkyl)-N($R^5$)$_2$, or —O—($C_1$-$C_6$-alkyl)-phenyl. In some embodiments, $R^2$ is —N($R^5$)—($C_2$-$C_3$-alkyl)-N($R^5$)$_2$, or —O—($C_1$-$C_3$-alkyl)-phenyl. In some embodiments, $R^2$ is —N($R^5$)—($C_2$-$C_3$-alkyl)-N($R^5$)$_2$, or —O—($C_1$-$C_3$-alkyl)-phenyl. In some embodiments, $R^2$ is —N($R^5$)—($C_2$-$C_3$-alkyl)-N($R^5$)$_2$. In some embodiments, $R^2$ is —O—($C_1$-$C_3$-alkyl)-phenyl.

In some embodiments, when $R^1$ is OH or $C_1$-$C_6$-alkyl, $R^2$ is OH, —O—($C_1$-$C_6$-alkyl)-phenyl, or —O—($C_2$-$C_6$-alkyl)-N($R^5$)$_3$$^+$halogen$^-$. In some embodiments, when $R^1$ is OH or $C_1$-$C_4$-alkyl, $R^2$ is OH, —O—($C_1$-$C_6$-alkyl)-phenyl, or —O—($C_2$-$C_6$-alkyl)-N($R^5$)$_3$$^+$halogen$^-$. In some embodiments, when $R^1$ is OH or $C_1$-$C_6$-alkyl, $R^2$ is —O—($C_1$-$C_6$-alkyl)-phenyl, or —O—($C_2$-$C_6$-alkyl)-N($R^5$)$_3$$^+$halogen$^-$. In some embodiments, when $R^1$ is OH or $C_1$-$C_6$-alkyl, $R^2$ is —O—($C_1$-$C_6$-alkyl)-phenyl. In some embodiments, when $R^1$ is OH or $C_1$-$C_6$-alkyl, $R^2$ is —O—($C_2$-$C_6$-alkyl)-N($R^5$)$_3$$^+$halogen$^-$.

In some embodiments, when $R^1$ is OH, $R^2$ is OH, —O—($C_1$-$C_6$-alkyl)-phenyl, or —O—($C_2$-$C_6$-alkyl)-N($R^5$)$_3$$^+$halogen$^-$. In some embodiments, when $R^1$ is $C_1$-$C_6$-alkyl, $R^2$ is —O—($C_1$-$C_6$-alkyl)-phenyl, or —O—($C_2$-$C_6$-alkyl)-N($R^5$)$_3$$^+$halogen$^-$. In some embodiments, when $R^1$ is OH, $R^2$ is OH, —O—($C_1$-$C_6$-alkyl)-phenyl, or —O—($C_2$-$C_6$-alkyl)-N($R^5$)$_3$$^+$halogen$^-$. In some embodiments, when $R^1$ is $C_1$-$C_4$-alkyl, $R^2$ is —O—($C_1$-$C_6$-alkyl)-phenyl, or —O—($C_2$-$C_6$-alkyl)-N($R^5$)$_3$$^+$halogen$^-$. In some embodiments, when $R^1$ is OH or $C_1$-$C_6$-alkyl, $R^2$ is —O—($C_1$-$C_6$-alkyl)-phenyl, or —O—($C_2$-$C_6$-alkyl)-N($R^5$)$_3$$^+$halogen$^-$. In some embodiments, when $R^1$ is OH or $C_1$-$C_6$-alkyl, $R^2$ is —O—($C_1$-$C_6$-alkyl)-phenyl. In some embodiments, when $R^1$ is OH or $C_1$-$C_6$-alkyl, $R^2$ is —O—($C_2$-$C_6$-alkyl)-N($R^5$)$_3$$^+$halogen$^-$.

In some embodiments, when $R^1$ is H, $R^2$ is —N($R^5$)—($C_2$-$C_6$-alkyl)-N($R^5$)$_2$. In some embodiments, when $R^1$ is H, $R^2$ is —N($R^5$)—($C_2$-$C_3$-alkyl)-N($R^5$)$_2$.

In some embodiments, $R^2$ and X together with the atoms to which they are attached form

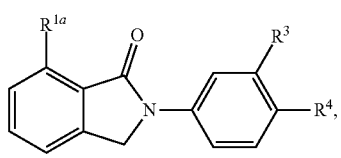

wherein $R^{1a}$ is OH or OCH$_3$; or
$R^2$ and X together with the atoms to which they are attached form

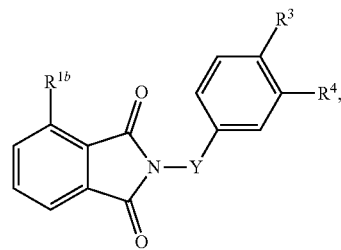

wherein Y is —($C_1$-$C_6$-alkyl); $R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$; or
$R^2$ and X together with the atoms to which they are attached form

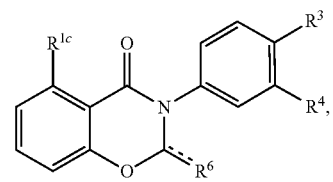

wherein
$R^{1c}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$;
$R^3$ is halogen or $C_1$-$C_2$-haloalkyl;
$R^4$ is halogen or $C_1$-$C_2$-haloalkyl;
$R^5$ is independently H or $C_1$-$C_4$-alkyl; and
==== is a double bond and $R^6$ is O, or
==== is a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3$ halogen.

In some embodiments, $R^2$ and X together with the atoms to which they are attached form

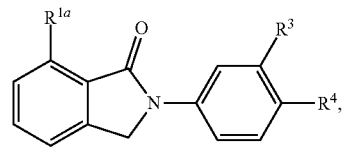

wherein $R^{1a}$ is OH; or
$R^2$ and X together with the atoms to which they are attached form

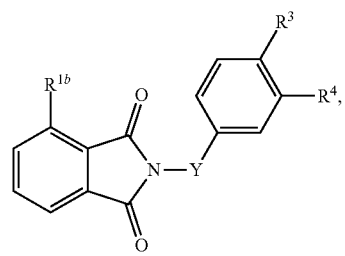

wherein Y is —($C_1$-$C_6$-alkyl); $R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$; or
$R^2$ and X together with the atoms to which they are attached form

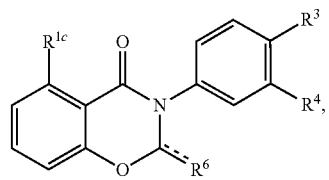

wherein $R^{1c}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3{}^+$halogen$^-$;

$R^3$ is halogen or $C_1$-$C_2$-haloalkyl;

$R^4$ is halogen or $C_1$-$C_2$-haloalkyl;

$R^5$ is independently H or $C_1$-$C_4$-alkyl; and

═══ is a double bond and $R^6$ is O, or

═══ is a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3{}^+$halogen$^-$.

In some embodiments, $R^2$ and X together with the atoms to which they are attached form

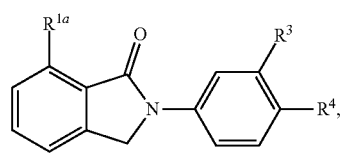

wherein $R^{1a}$ is OH or OCH$_3$; or $R^2$ and X together with the atoms to which they are attached form

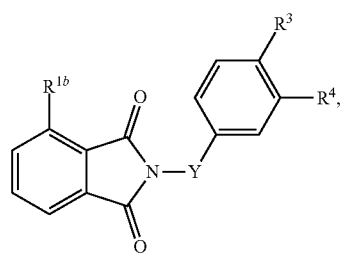

wherein Y is —($C_1$-$C_6$-alkyl); $R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3{}^+$halogen$^-$.

In some embodiments, $R^2$ and X together with the atoms to which they are attached form

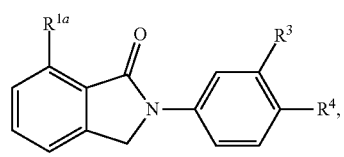

wherein $R^{1a}$ is OH; or $R^2$ and X together with the atoms to which they are attached form

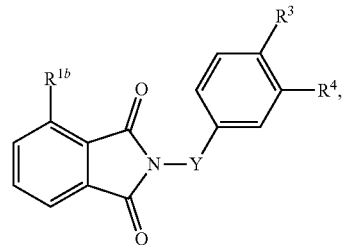

wherein Y is —($C_1$-$C_6$-alkyl); $R^{1b}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3{}^+$halogen$^-$.

In some embodiments, $R^2$ and X together with the atoms to which they are attached form

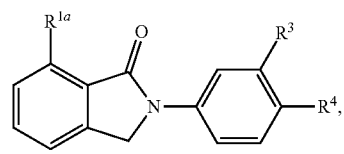

wherein $R^{1a}$ is OH or OCH$_3$; or $R^2$ and X together with the atoms to which they are attached form

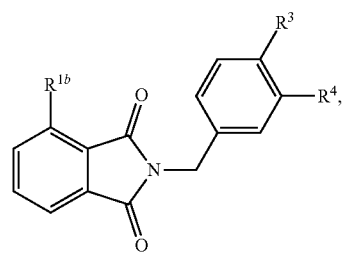

wherein $R^{1b}$ is OH, O—($C_1$-$C_6$-alkyl), or —O—($C_2$-$C_6$-alkyl)-N($R^5$)$_2$.

In some embodiments, $R^2$ and X together with the atoms to which they are attached form

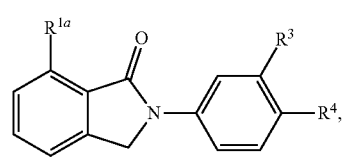

wherein $R^{1a}$ is OH; or $R^2$ and X together with the atoms to which they are attached form

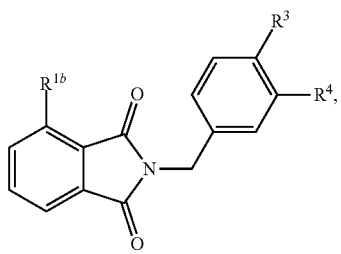

wherein $R^{1b}$ is OH, O—($C_1$-$C_6$-alkyl), or —O—($C_2$-$C_6$-alkyl)-N($R^5$)$_2$.

In some embodiments, $R^2$ and X together with the atoms to which they are attached form

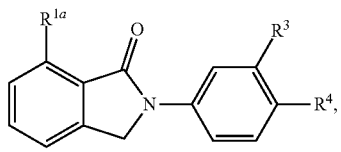

wherein $R^{1a}$ is OH or OCH$_3$; or
$R^2$ and X together with the atoms to which they are attached form

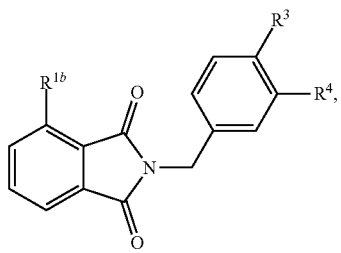

wherein $R^{1b}$ is OH, O—($C_1$-$C_3$-alkyl), or —O—($C_2$-$C_4$-alkyl)-N($R^5$)$_2$.

In some embodiments, $R^2$ and X together with the atoms to which they are attached form

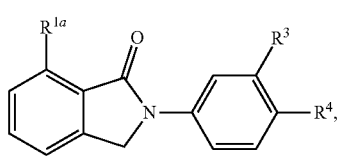

wherein $R^{1a}$ is OH; or
$R^2$ and X together with the atoms to which they are attached form

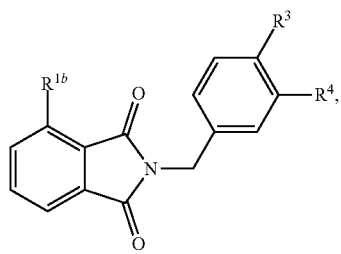

wherein $R^{1b}$ is OH, O—($C_1$-$C_3$-alkyl), or —O—($C_2$-$C_4$-alkyl)-N($R^5$)$_2$.

In some embodiments, $R^2$ and X together with the atoms to which they are attached form

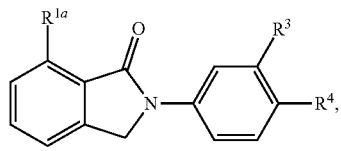

wherein $R^{1a}$ is OH or OCH$_3$.

In some embodiments, $R^2$ and X together with the atoms to which they are attached form

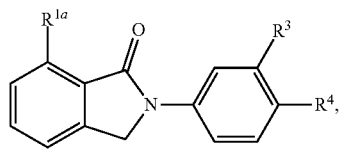

wherein $R^{1a}$ is OH.

In some embodiments, $R^2$ and X together with the atoms to which they are attached form

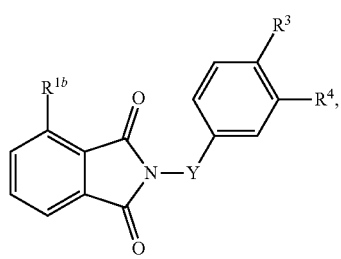

wherein Y is —($C_1$-$C_6$-alkyl); and $R^{1b}$ is OH, O—($C_1$-$C_6$-alkyl), or —O—($C_2$-$C_6$-alkyl)-N($R^5$)$_2$.

In some embodiments, $R^2$ and X together with the atoms to which they are attached form

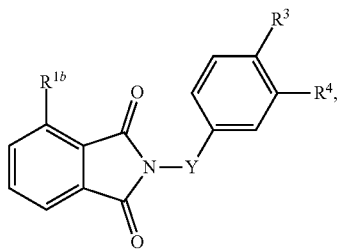

wherein Y is —(C$_1$-C$_3$-alkyl); and R$^{1b}$ is OH, O—(C$_1$-C$_3$-alkyl), or —O—(C$_2$-C$_4$-alkyl)-N(R$^5$)$_2$.

In some embodiments, R$^2$ and X together with the atoms to which they are attached form

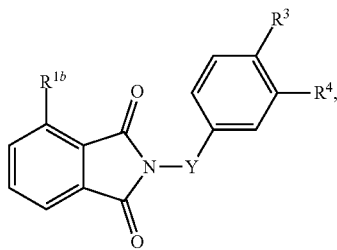

wherein Y is —(C$_1$-C$_2$-alkyl); and R$^{1b}$ is O—(C$_1$-C$_3$-alkyl), or —O—(C$_2$-C$_4$-alkyl)-N(R$^5$)$_2$.

In some embodiments, R$^2$ and X together with the atoms to which they are attached form

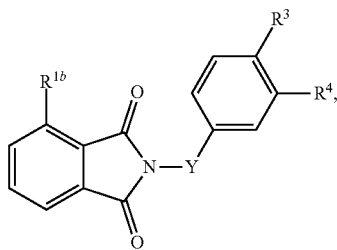

wherein Y is —(C$_1$-C$_2$-alkyl); and R$^{1b}$ is —O—(C$_2$-C$_4$-alkyl)-N(R$^5$)$_2$.

In some embodiments, R$^2$ and X together with the atoms to which they are attached form

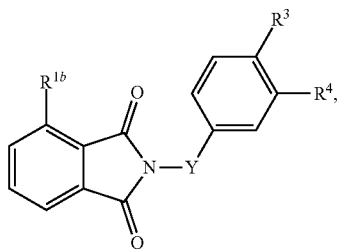

wherein Y is —(C$_1$-C$_6$-alkyl); and R$^{1b}$ is OH, O—(C$_1$-C$_6$-alkyl), or —O—(C$_2$-C$_6$-alkyl)-N(R$^5$)$_2$.

In some embodiments, R$^2$ and X together with the atoms to which they are attached form

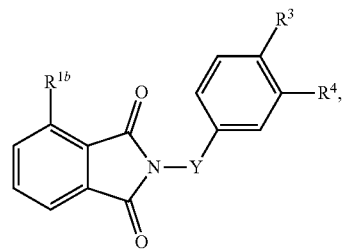

wherein Y is —(C$_1$-C$_3$-alkyl); and R$^{1b}$ is OH, O—(C$_1$-C$_3$-alkyl), or —O—(C$_2$-C$_4$-alkyl)-N(R$^5$)$_2$.

In some embodiments, R$^2$ and X together with the atoms to which they are attached form

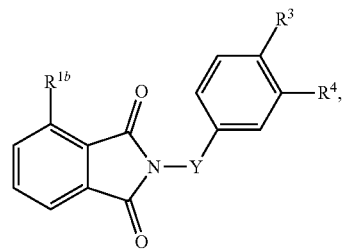

wherein Y is —(C$_1$-C$_2$-alkyl); and R$^{1b}$ is O—(C$_1$-C$_3$-alkyl), or —O—(C$_2$-C$_4$-alkyl)-N(R$^5$)$_2$.

In some embodiments, R$^2$ and X together with the atoms to which they are attached form

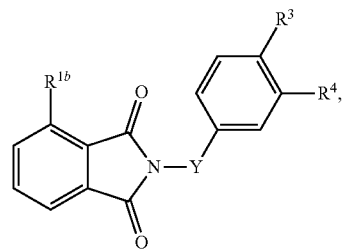

wherein Y is —(C$_1$-C$_2$-alkyl); and R$^{1b}$ is —O—(C$_2$-C$_4$-alkyl)-N(R$^5$)$_2$.

In some embodiments, R$^2$ and X together with the atoms to which they are attached form

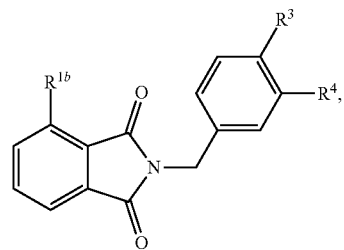

wherein R$^{1b}$ is OH, O—(C$_1$-C$_6$-alkyl), or —O—(C$_2$-C$_6$-alkyl)-N(R$^5$)$_2$.

In some embodiments, R$^2$ and X together with the atoms to which they are attached form

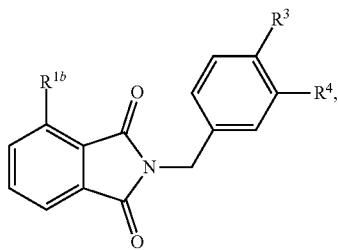

wherein $R^{1b}$ is OH, O—($C_1$-$C_3$-alkyl), or —O—($C_2$-$C_4$-alkyl)-N($R^5$)$_2$.

In some embodiments, $R^2$ and X together with the atoms to which they are attached form

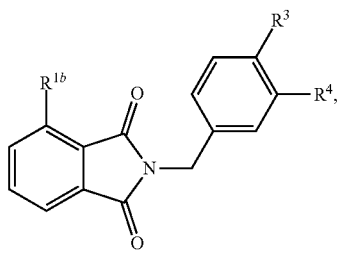

wherein $R^{1b}$ is O—($C_1$-$C_3$-alkyl), or —O—($C_2$-$C_4$-alkyl)-N($R^5$)$_2$.

In some embodiments, $R^2$ and X together with the atoms to which they are attached form

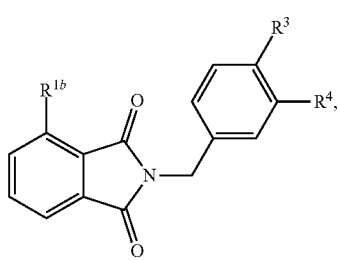

wherein $R^{1b}$ is —O—($C_2$-$C_4$-alkyl)-N($R^5$)$_2$.

In some embodiments, $R^2$ and X together with the atoms to which they are attached form

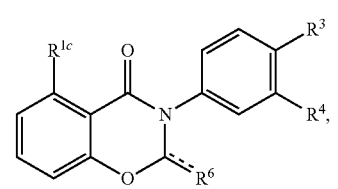

wherein $R^{1c}$ is OH, O—($C_1$-$C_6$-alkyl), —O—($C_2$-$C_6$-alkyl)-N($R^5$)$_2$, or —O—($C_2$-$C_6$-alkyl)-N($R^5$)$_3{}^+$halogen$^-$; $R^3$ is halogen or $C_1$-$C_2$-haloalkyl; $R^4$ is halogen or $C_1$-$C_2$-haloalkyl; $R^5$ is independently H or $C_1$-$C_4$-alkyl; and ═ is a double bond and $R^6$ is O, or ═ is a single bond and $R^6$ is —($C_1$-$C_6$-alkyl), —($C_1$-$C_6$-alkyl)-N($R^5$)$_2$, or —($C_1$-$C_6$-alkyl)-N($R^5$)$_3{}^+$halogen$^-$.

In some embodiments, $R^2$ and X together with the atoms to which they are attached form

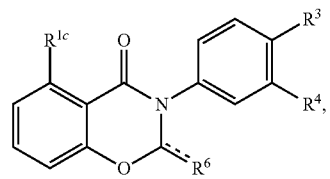

wherein $R^{1c}$ is OH, O—($C_1$-$C_3$-alkyl), —O—($C_2$-$C_4$-alkyl)-N($R^5$)$_2$, or —O—($C_2$-$C_4$-alkyl)-N($R^5$)$_3{}^+$halogen$^-$; and ═ is a double bond and $R^6$ is O, or ═ is a single bond and $R^6$ is —($C_1$-$C_3$-alkyl), —($C_1$-$C_3$-alkyl)-N($R^5$)$_2$, or —($C_1$-$C_3$-alkyl)-N($R^5$)$_3{}^+$halogen$^-$.

In some embodiments, $R^2$ and X together with the atoms to which they are attached form

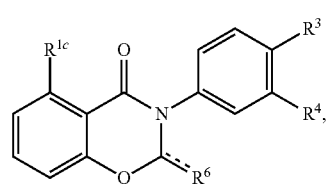

wherein $R^{1c}$ is OH, O—($C_1$-$C_3$-alkyl), —O—($C_2$-$C_4$-alkyl)-N($R^5$)$_2$, or —O—($C_2$-$C_4$-alkyl)-N($R^5$)$_3{}^+$halogen$^-$; and ═ is a double bond and $R^6$ is O.

In some embodiments, $R^2$ and X together with the atoms to which they are attached form

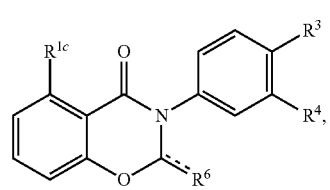

wherein $R^{1c}$ is OH, O—($C_1$-$C_3$-alkyl), —O—($C_2$-$C_4$-alkyl)-N($R^5$)$_2$, or —O—($C_2$-$C_4$-alkyl)-N($R^5$)$_3{}^+$halogen$^-$; and ═ is a single bond and $R^6$ is —($C_1$-$C_3$-alkyl), —($C_1$-$C_3$-alkyl)-N($R^5$)$_2$, or —($C_1$-$C_3$-alkyl)-N($R^5$)$_3{}^+$halogen$^-$.

In some embodiments, $R^3$ is halogen or $C_1$-$C_2$-haloalkyl. In some embodiments, $R^3$ is halogen or $C_1$-haloalkyl. In some embodiments, $R^3$ is halogen or trifluoromethyl. In some embodiments, $R^3$ is halogen. In some embodiments, $R^3$ is trifluoromethyl.

In some embodiments, $R^4$ is halogen or $C_1$-$C_2$-haloalkyl. In some embodiments, $R^4$ is halogen or $C_1$-haloalkyl. In some embodiments, $R^4$ is halogen or trifluoromethyl. In some embodiments, $R^4$ is halogen. In some embodiments, $R^4$ is trifluoromethyl.

In some embodiments, $R^5$ is independently H or $C_1$-$C_4$-alkyl. In some embodiments, $R^5$ is independently H or methyl. In some embodiments, $R^5$ is H. In some embodiments, $R^5$ is $C_1$-$C_4$-alkyl. In some embodiments, $R^5$ is methyl.

In some embodiments, $R^6$ is —($C_1$-$C_6$-alkyl), —($C_1$-$C_6$-alkyl)-N($R^5$)$_2$, or —($C_1$-$C_6$-alkyl)-N($R^5$)$_3{}^+$halogen$^-$. In some embodiments, $R^6$ is —($C_1$-$C_6$-alkyl), or —($C_1$-$C_6$-alkyl)-N($R^5$)$_2$. In some embodiments, $R^6$ is —($C_1$-$C_3$-alkyl), —($C_1$-$C_3$-alkyl)-N($R^5$)$_2$, or —($C_1$-$C_3$-alkyl)-N($R^5$)$_3{}^+$halogen$^-$. In some embodiments, $R^6$ is —($C_1$-$C_3$-alkyl), or —(C₁-C₃-alkyl)-N(R⁵)₂. In some embodiments, R⁶ is —(C₁-C₂-alkyl), —(C₁-C₂-alkyl)-N(R⁵)₂, or —(C₁-C₂-alkyl)-N(R⁵)₃⁺halogen⁻. In some embodiments, R⁶ is —(C₁-C₂-alkyl), or —(C₁-C₂-alkyl)-N(R⁵)₂.

In some embodiments, R⁶ is —(C₁-C₆-alkyl). In some embodiments, R⁶ is —(C₁-C₂-alkyl). In some embodiments, R⁶ is —(C₁-C₂-alkyl).

In some embodiments, R⁶ is —(C₁-C₆-alkyl)-N(R⁵)₂, In some embodiments, R⁶ is —(C₁-C₃-alkyl)-N(R⁵)₂, In some embodiments, R⁶ is —(C₁-C₃-alkyl)-N(R⁵)₂, In some embodiments, the compound is selected from the group consisting of

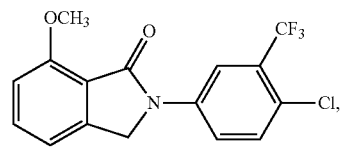

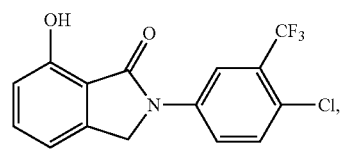

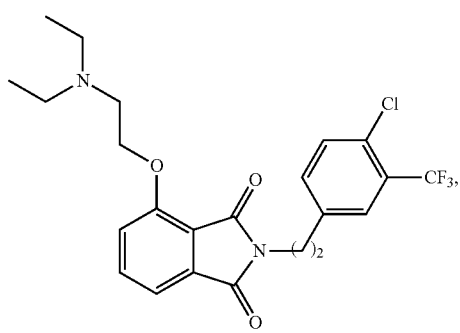

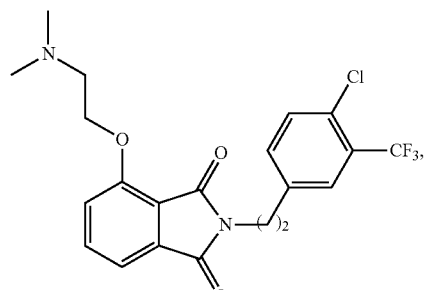

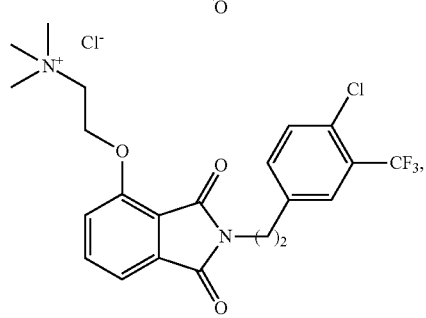

-continued

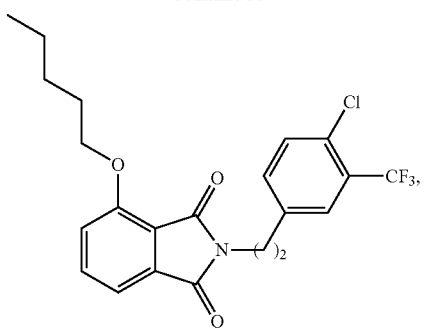

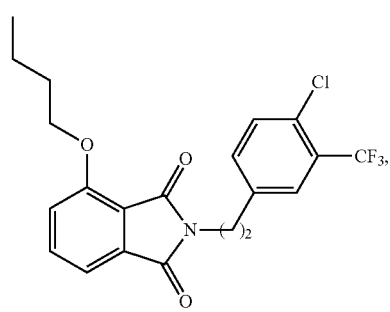

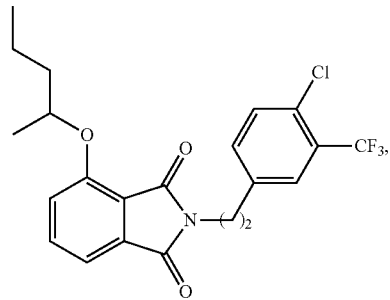

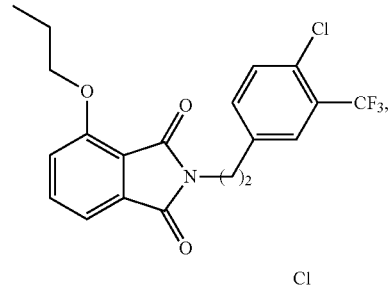

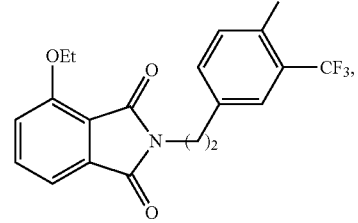

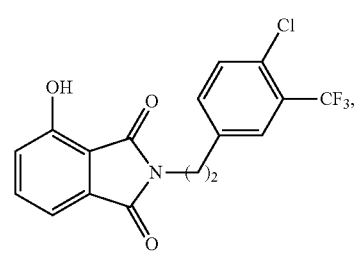

51
-continued
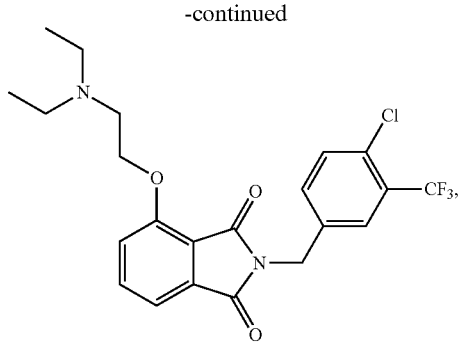
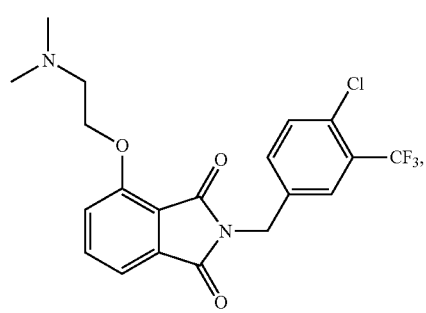
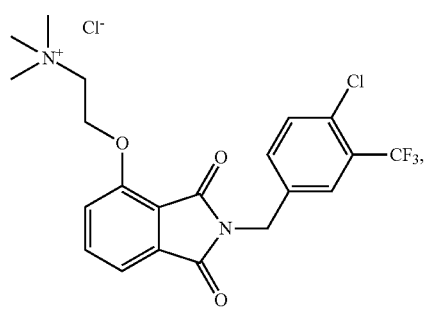
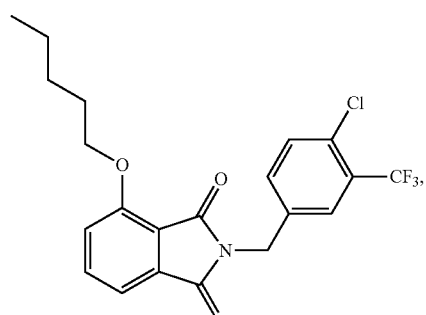
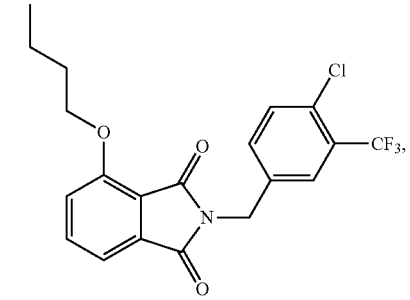
52
-continued
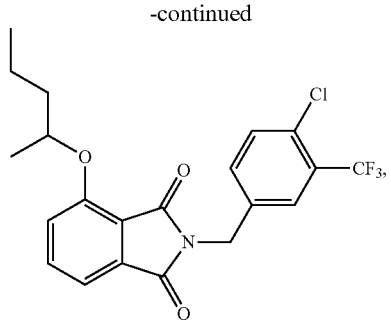
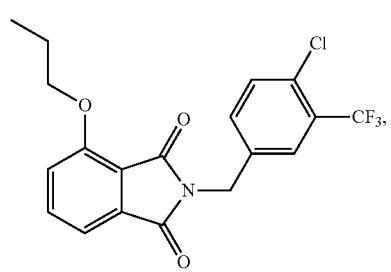
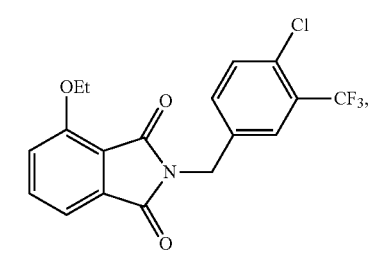
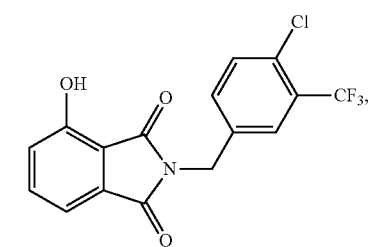
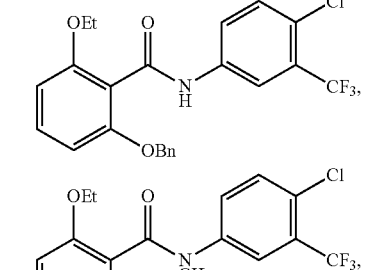
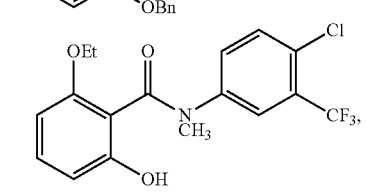

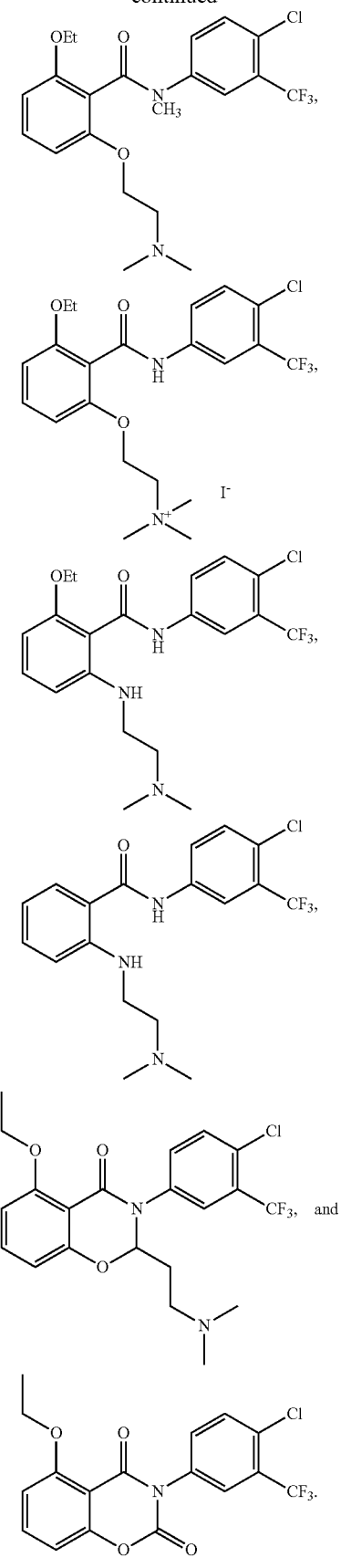
In some embodiments, the compound is selected from the group consisting of,
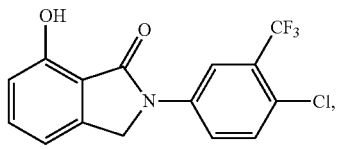
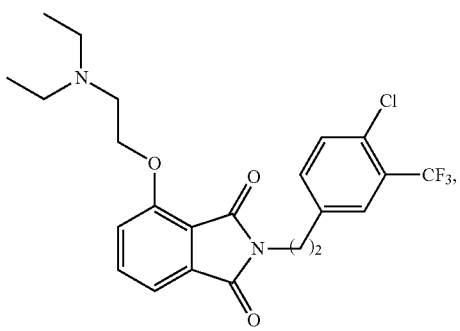
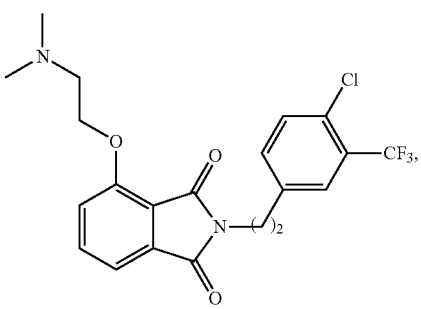
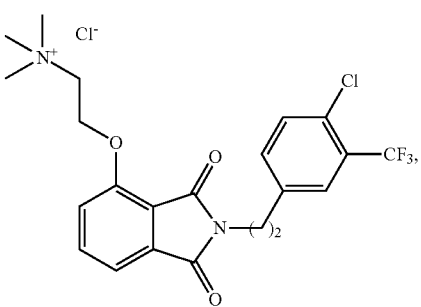
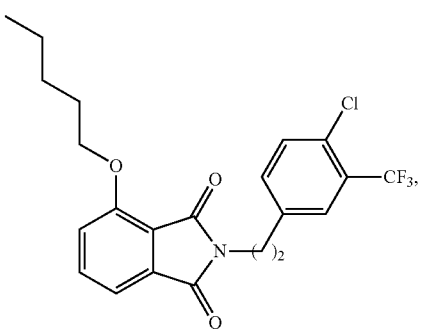

55
-continued
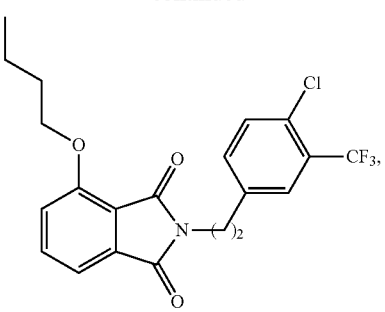
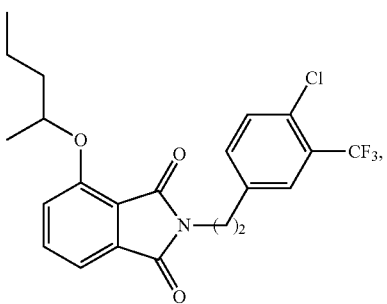
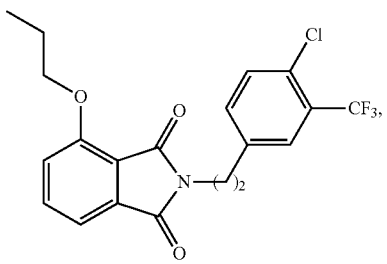
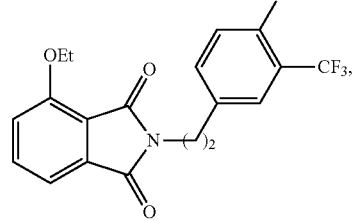
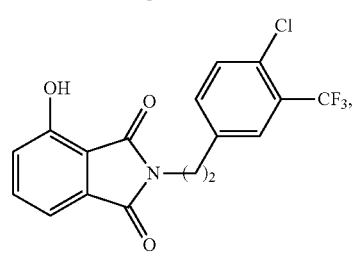
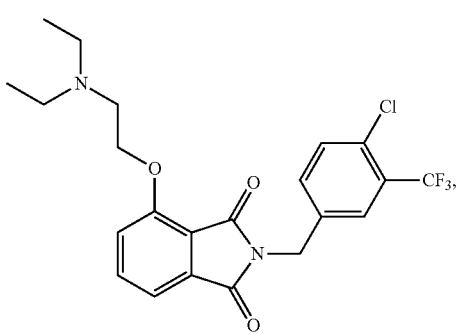
56
-continued
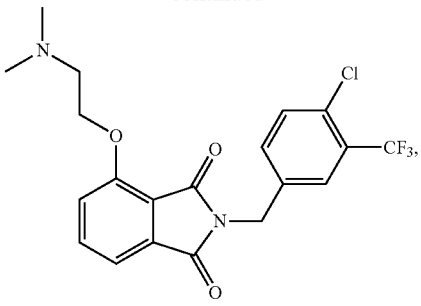
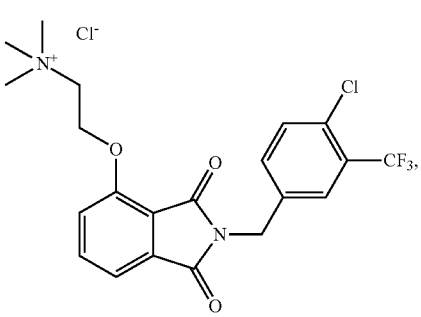
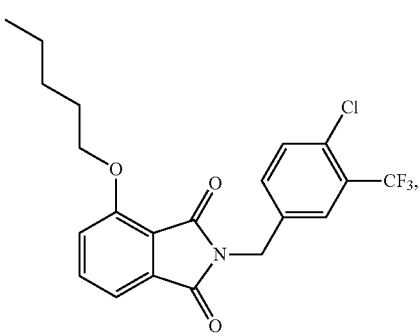
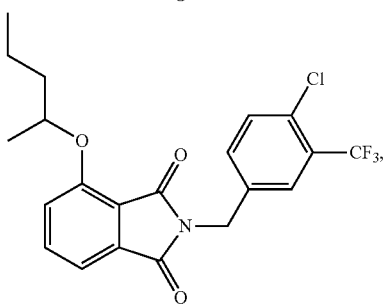

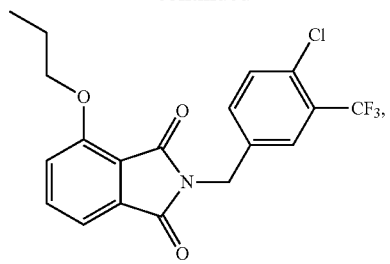
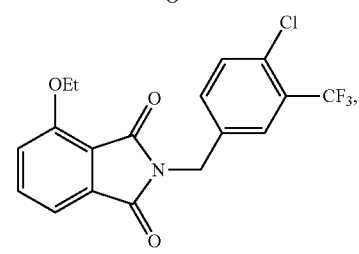
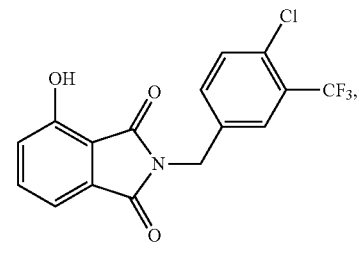
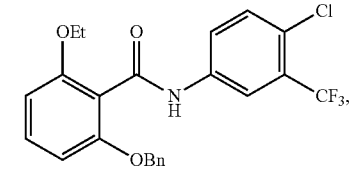
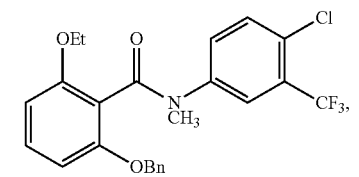
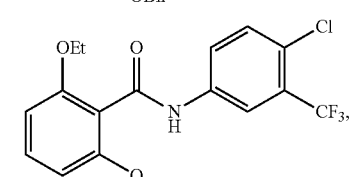
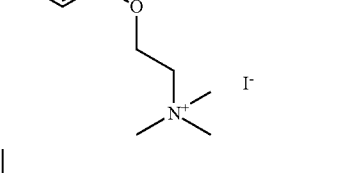
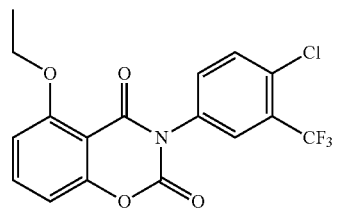
In some embodiments, the compound is selected from the group consisting of
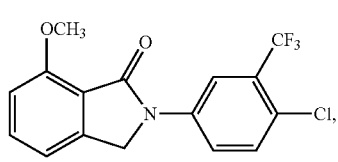
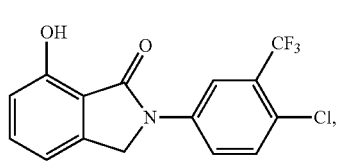
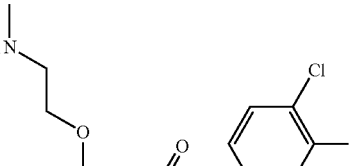
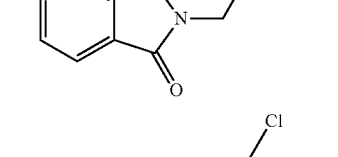
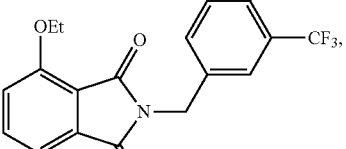
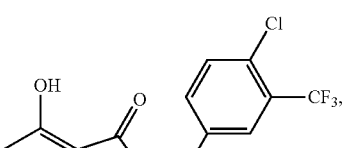

-continued
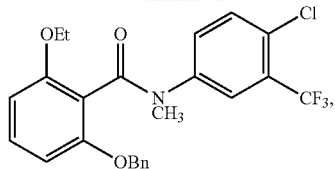
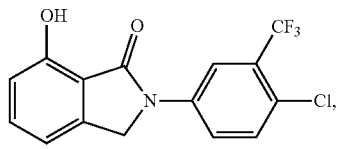
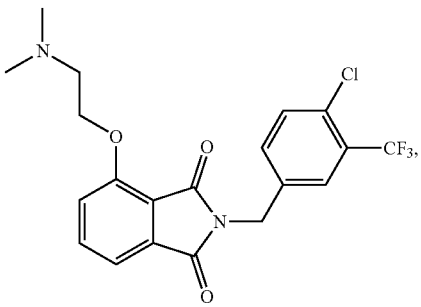
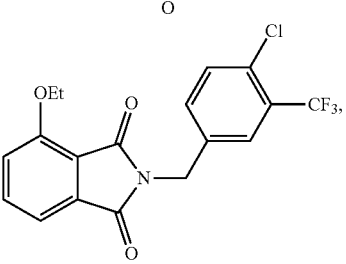
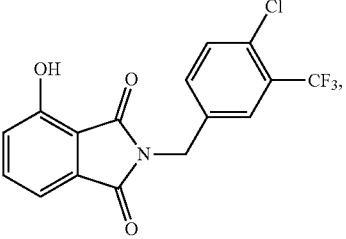
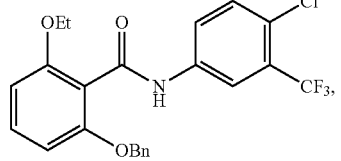
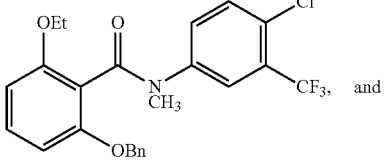 and
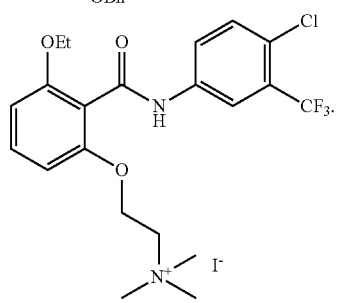
In some embodiments, the compound is selected from the group consisting of
In some embodiments, the compound is selected from the group consisting of

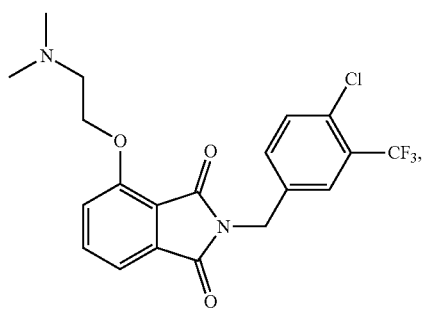
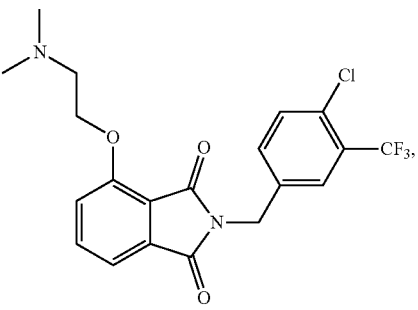
In some embodiments, the compound is selected from the group consisting of
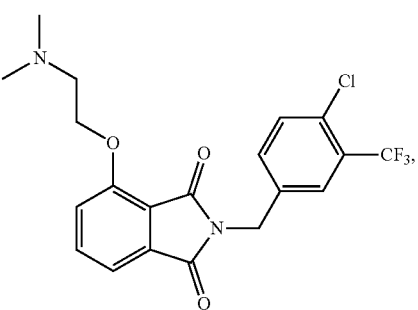
In some embodiments, the compound is selected from the group consisting of -continued
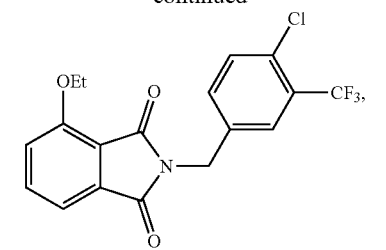
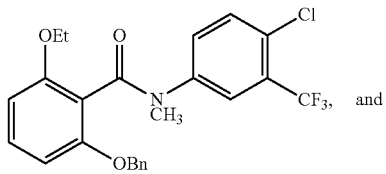
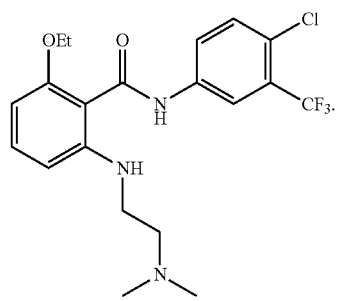
In some embodiments, the compound is selected from the group consisting of
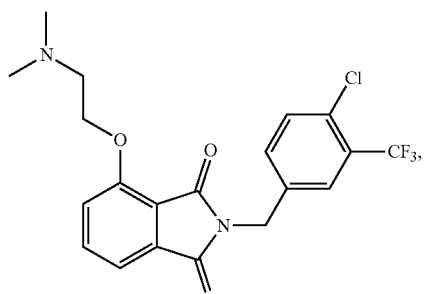
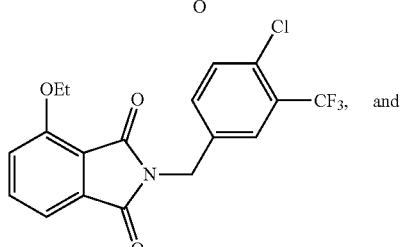
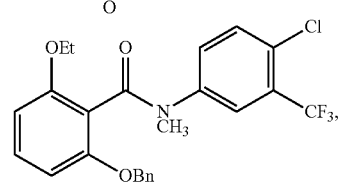
In some embodiments, the compound is selected from the group consisting of
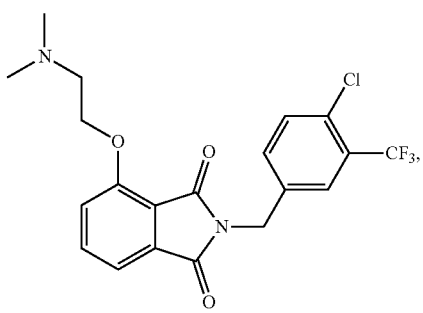
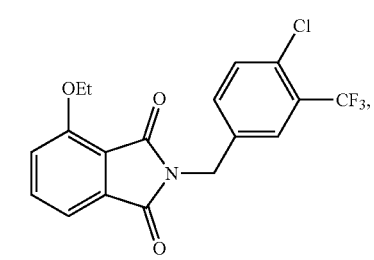
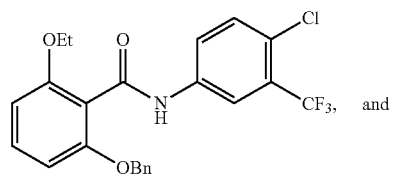
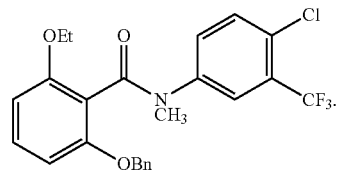
In some embodiments, the compound is selected from the group consisting of
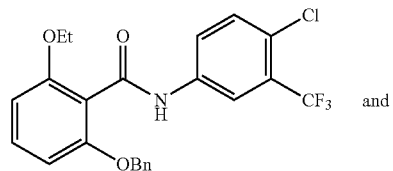
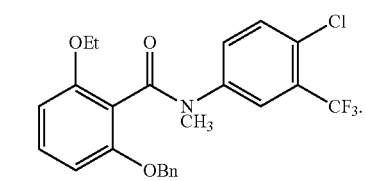
In some embodiments, the compound is selected from the group consisting of

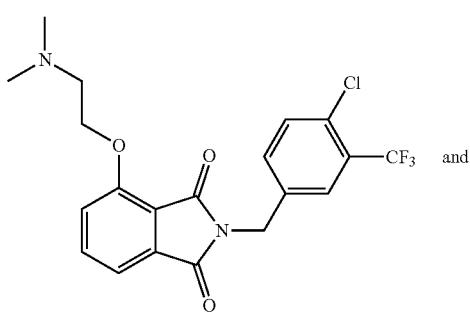 and
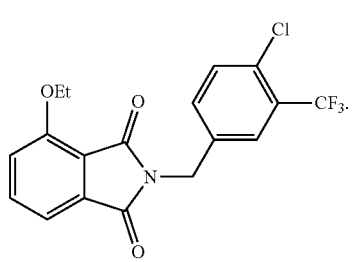
In some embodiments, the compound is selected from the group consisting of
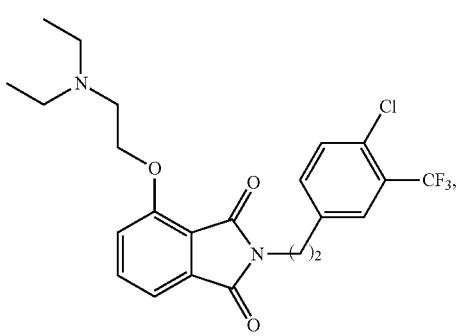
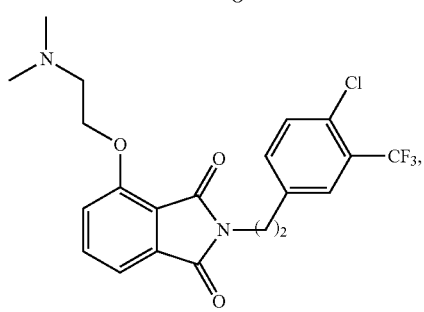
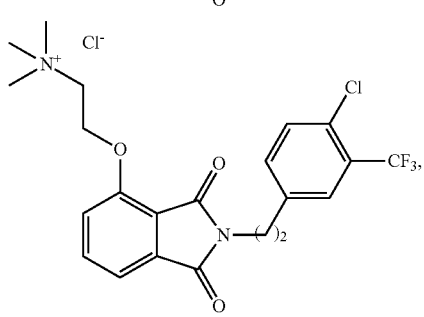
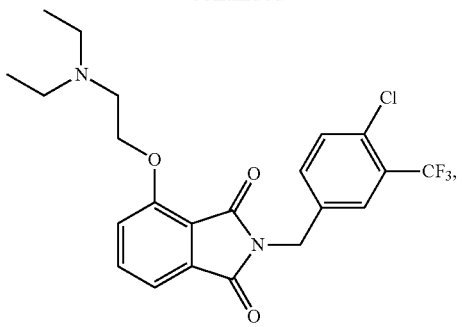
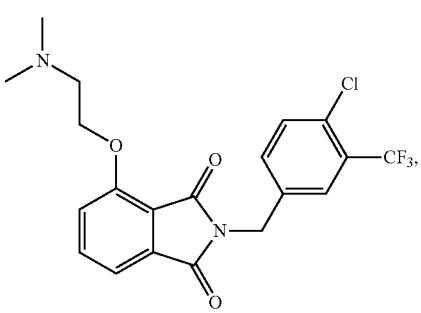
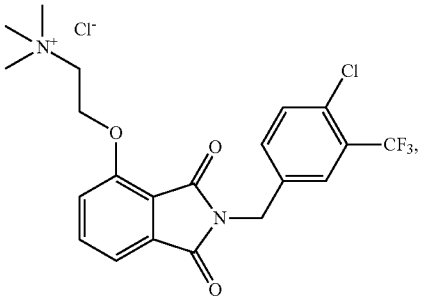
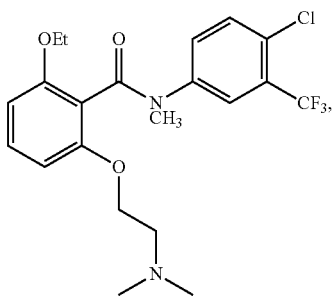
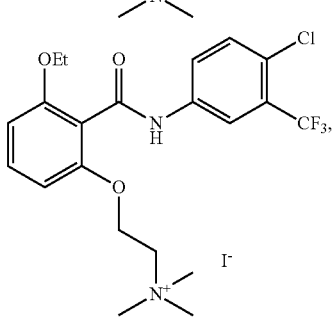

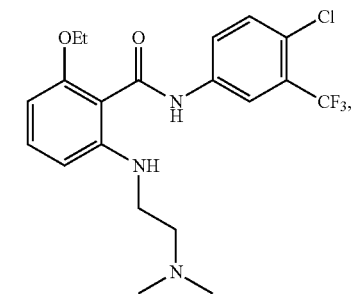
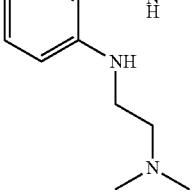
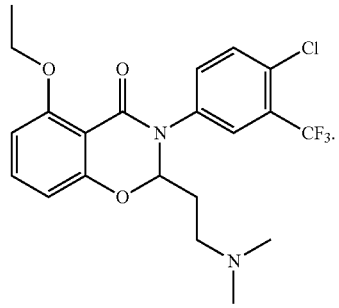
In some embodiments, the compound is selected from the group consisting of
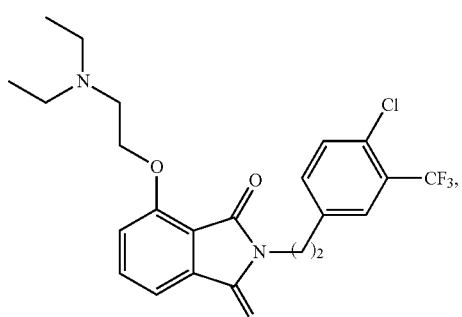
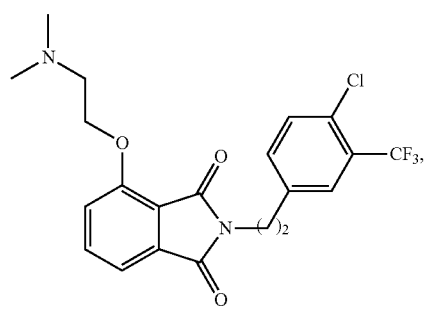
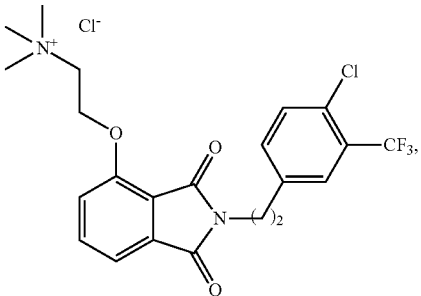
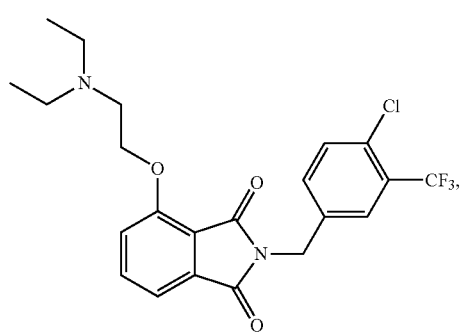
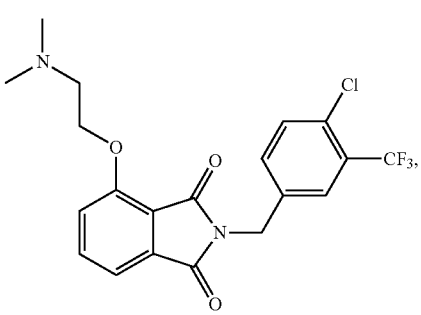
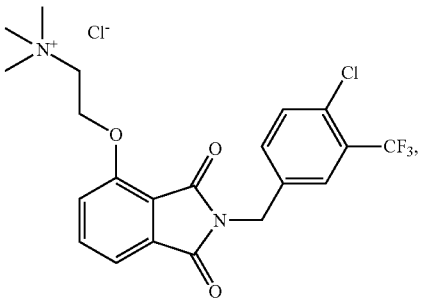
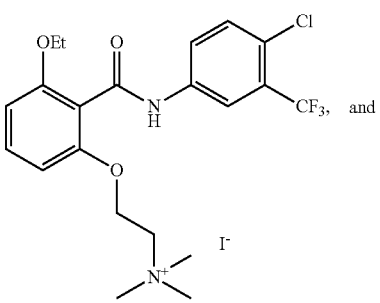

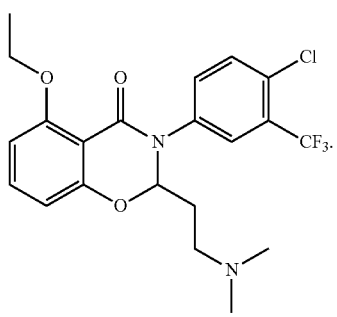
In some embodiments, the compound is selected from the group consisting of
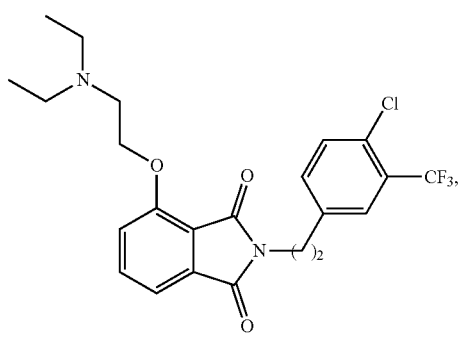
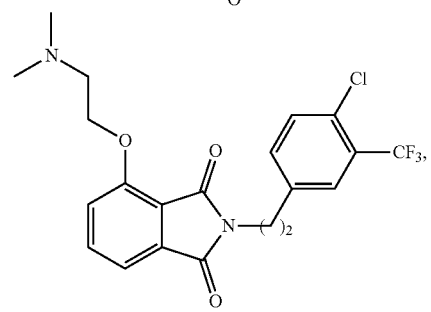
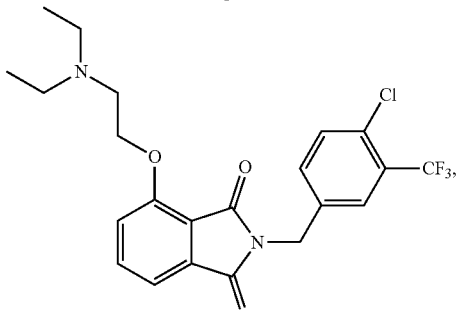
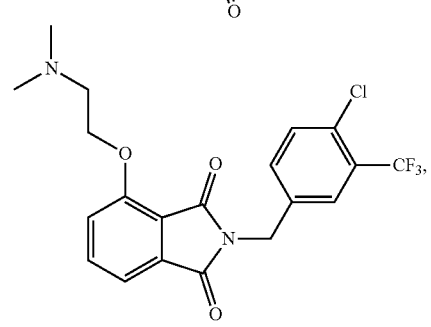
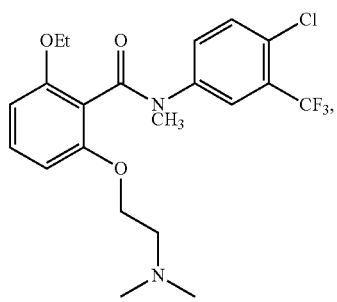
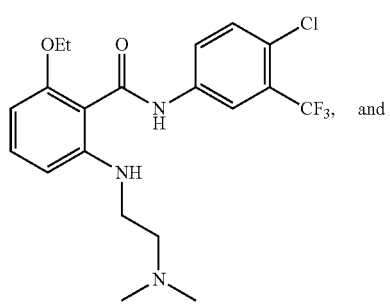
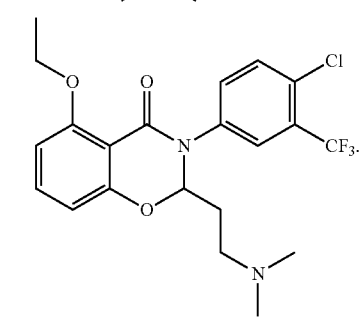
In some embodiments, the compound is selected from the group consisting of
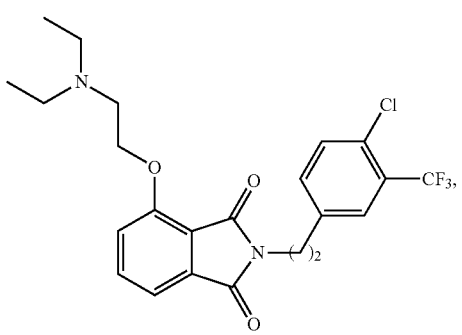
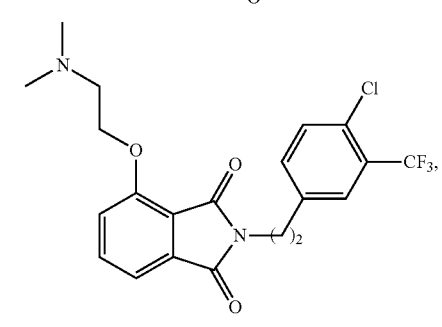

-continued

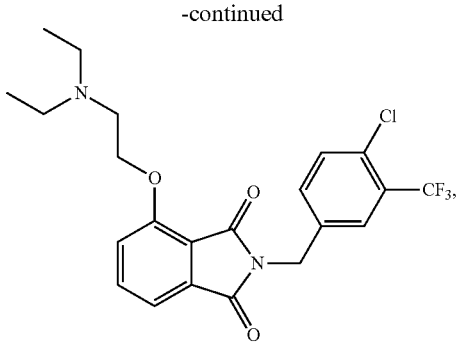

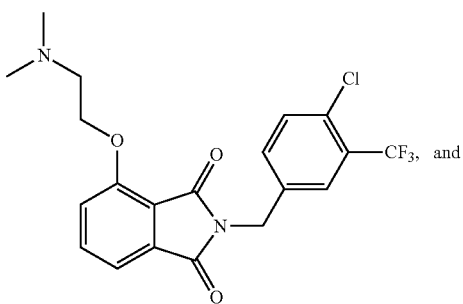

Exemplary methods of preparation of compounds of formula (I) are shown in Scheme A.

Scheme A.

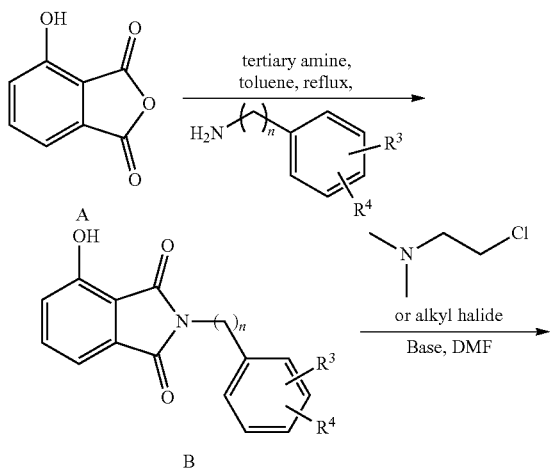

-continued

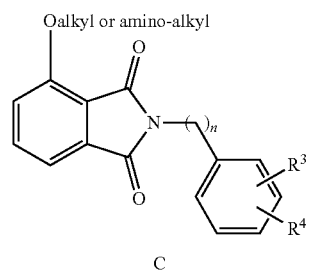

C

Compound A can be treated with a primary amine in the presence of a tertiary amine in a solvent such as toluene and heated to obtain compounds B. Compounds B can be alkylated using an alkyl halide or aminoalkyl halide in the presence of a base such as potassium carbonate in a solvent such as N,N-dimethylformamide to obtain compounds C. In the case of compounds C that contain amino-alkyl groups, treatment with methyl iodide can be performed to obtain the methylamino salt.

Further exemplary methods of preparation of compounds of formula (I) are shown in Scheme B.

Scheme B.

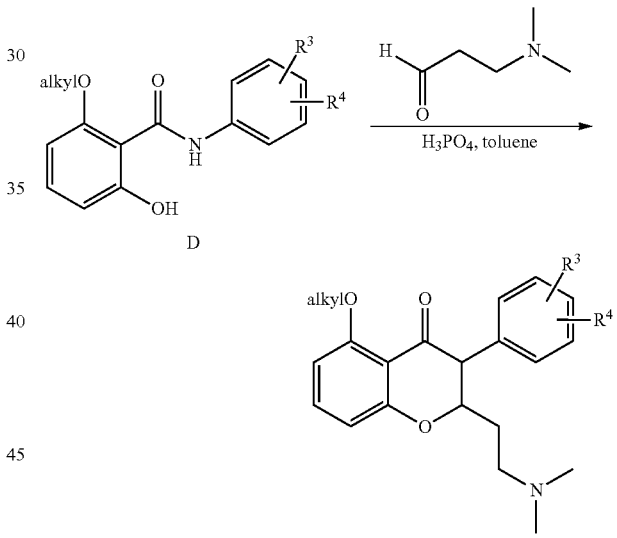

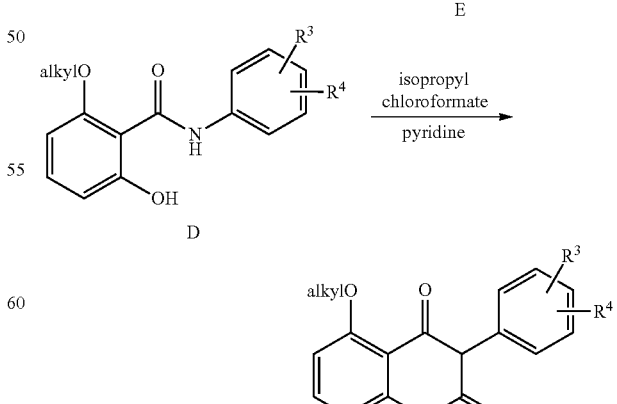

Compounds D can be treated with an amino-aldehyde in the presence of an acid such as phosphoric acid in a solvent such as toluene to obtain compounds E. Alternatively, compounds D can be treated with a formate source such as isopropyl chloroformate or triphosgene in a solvent such as pyridine to obtain compounds F.

Early amnesic changes in Alzheimer's disease (AD) are thought to be linked to synaptic dysfunction. β-amyloid (Aβ), a peptide that is present in high amounts in the disease, has been found to inhibit memory (*Proc Natl Acad Sci USA*, 2006. 103(23): p. 8852-7; *Nat Neurosci*, 2005. 8(1): p. 79-84; each herein incorporated by reference in its entirety) and its electrophysiological model, long-term potentiation (LTP) (*Neuroreport*, 1997, 8(15), 3213-7; *Eur J Pharmacol*, 1999, 382(3), 167-75; *Proc Natl Acad Sci* US A, 2002, 99(20), 13217-21; *Nature*, 2002, 416(6880), 535-9; *J Neurosci Res*, 2000, 60(1), 65-72; *Proc Natl Acad Sci* US A, 1998, 95(11), 6448-53; each herein incorporated by reference in its entirety). Memory is known to be modulated by epigenetics through regulation of gene expression. Epigenetics is defined as the mechanism that changes gene expression by 'marking' DNA or its associated proteins, through processes such as DNA methylation and histone modification, without changing the DNA sequence itself (*Biochem J*, 2001. 356(Pt 1): p. 1-10; herein incorporated by reference in its entirety). Modification of histones by, for example, the addition or removal of acetyl or methyl functional groups causes the chromatin structure to open or close, so that the information contained within the DNA is made more or less accessible to transcription factors. Deregulation of one of the epigenetic mechanisms may lead to memory disruption. For example, reduction of histone acetylation causes the chromatin structure to close, so that the information contained within the DNA can be less accessible to transcription factors and memory formation (*Biochem J*, 2001. 356(Pt 1): p. 1-10; herein incorporated by reference in its entirety).

Epigenetic modifications including acetylation of histones may contribute to gene expression changes important to learning and memory (*Science* 2010: 328(5979), 701-702; herein incorporated by reference in its entirety). Addition of acetyl groups to histones by histone acyltransferases (HAT) enhances gene expression, while their removal by histone deacetylases (HDAC) reduces gene expression. Reduction in histone acetylation has recently been linked to age-induced memory impairment and various neurodegenerative diseases (*Science* 2010: 328(5979), 701-702; herein incorporated by reference in its entirety). HDAC inhibitors have been shown to enhance memory in mice (*Nature* 459, 55-60 (7 May 2009); herein incorporated by reference in its entirety). Histone acetylation is discussed in, for example, U.S. Patent Publication Nos. 2010/0166781; 2010/0144885; 2009/0076155; *Neuroscience* 2011, 194, 272-281; and *J. Phys. Chem B* 2007, 111(17), 4527-4534 (each of which herein incorporated by reference in its entirety).

HAT activators can be a viable approach to enhance histone acetylation. Further details on HAT activators can be found in WO 2011/072243 and WO 2012/088420, each incorporated by reference herein in its entirety. HAT activators are also described in U.S. patent application Ser. Nos. 12/493,490; 13/493,490 and 13/996,483; each incorporated by reference herein in its entirety. Increasing histone acetylation has been shown to improve outcome in a wide variety of diseases as diverse as asthma, infectious disease and psychiatric diseases.

In some embodiments, the compounds improve cognition or memory in AD and Alzheimer's-like pathologies, as well as minimize the side effects for subjects afflicted with other neurodegenerative diseases. In some embodiments, the compounds of the invention can also be developed as anti-cancer therapies. In some embodiments, acylation of histone proteins increases gene expression in a subject resulting in enhanced memory and cognition.

In some embodiments, the invention provides for the utilization of a compound of formula (I) as a memory enhancer in aging subjects (for example, a subject that is greater than about 55 years old). In some embodiments, the invention provides for the utilization of a compound of formula (I) as a memory enhancer for other conditions associated with cognitive decrease/impairment. Non-limiting examples of conditions associated with cognitive decrease/impairment include a variety of syndromes associated with mental retardation and syndromes associated with learning disabilities, Parkinson's disease, Pick's disease, a Lewy body disease, amyotrophic lateral sclerosis, Huntington's disease, Creutzfeld-Jakob disease, Down syndrome, multiple system atrophy, neuronal degeneration with brain iron accumulation type I (Hallervorden-Spatz disease), pure autonomic failure, REM sleep behavior disorder, mild cognitive impairment (MCI), cerebral amyloid angiopathy (CAA), mild cognitive deficits, aging, vascular dementias mixed with Alzheimer's disease, a neurodegenerative disease characterized by abnormal amyloid deposition, and any combination thereof.

In some embodiments, the compound of formula (I) is used to treat a cancer in a subject in need thereof. Non-limiting examples of cancers include B cell lymphoma, colon cancer, lung cancer, renal cancer, bladder cancer, T cell lymphoma, mycloma, leukemia, chronic mycloid leukemia, acute mycloid leukemia, chronic lymphocytic leukemia, acute lymphocytic leukemia, hematopoietic neoplasias, thymoma, lymphoma, sarcoma, lung cancer, liver cancer, non-Hodgkin's lymphoma, Hodgkin's lymphoma, uterine cancer, renal cell carcinoma, hepatoma, adenocarcinoma, breast cancer, pancreatic cancer, liver cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, astrocytoma, medulloblastoma, craniopharyngioma, ependymoma, pinealoma, hemangioblastoma, acoustic neuroma, oligodendroglioma, meningioma, retinoblastoma, leukemia, melanoma, neuroblastoma, small cell lung carcinoma, bladder carcinoma, lymphoma, multiple myeloma, follicular lymphoma and medullary carcinoma.

In one embodiment, the cancer is colon cancer, renal cancer, T cell leukemia, myeloma, leukemia, acute myeloid leukemia, acute lymphocytic leukemia, renal cell carcinoma, adenocarcinoma, glioblastoma, breast carcinoma, prostate carcinoma, or lung carcinoma.

In one embodiment, the cancer is Hodgkin's lymphoma, non-Hodgkin's lymphoma, B cell lymphoma, T cell lymphoma, or follicular lymphoma. In another embodiment, the B cell lymphoma is diffuse large B-cell lymphoma. In a further embodiment, the diffuse large B-cell lymphoma is a germinal center-derived diffuse large B cell lymphoma, an activated B-cell-derived (ABC) diffuse large B-cell lymphoma, or a non-germinal center diffuse large B cell lymphoma.

Modulation of the acetylation state of histones, transcription factors, and other regulatory proteins is known to influence their activity within cancer and inflammatory cells. Classically, modulation of acetylation status is known to influence the condensation of chromatin. In cancer, histones are deacetylated maintaining a condensed chromatin structure, and a transcriptionally silenced state. This transcriptional inactivation is mediated by HDACs which remove acetyl groups from histone tails, maintain a condensed chromatic structure. Inhibitors of HDACs help maintain transcriptionally active chromatin, theoretically allowing for expression of tumor suppressor genes. One observation that has evolved is that histones are not the only targets of acetylation. It is now accepted that post-translational acetylation of intracellular proteins such as tumor suppressors (p53) and oncogenes (Bcl6) plays a critical role in influencing their activity. It has been established that there is a network of proteins and enzymes that can be modified by acetylation, now collectively referred to as the acetylome. It has been shown that modulation of key intracellular proteins with HDAC inhibitors can lead to profound effects in lymphoma cell lines, in mouse models of lymphoma and in patients with drug-resistant lymphoma. Treatment with HDAC inhibitors, like vorinostat, can inactivate the oncogene, Bcl6, while simultaneously activating the tumor suppressor, p53. The tumor suppress p53 plays an important role in many cancers, and mutations in p53 are critical in the development of many cancers. Enhancement of p53 activity through acetylation protects the tumor suppressor from proteosomal degradation and stimulates induction of apoptosis. In one embodiment, there is also provided a method for reducing the proliferation of a cancer cell or cells comprising contacting the cell(s) with the compound of formula (I). In a similar embodiment there is provided a use of the compound of formula (I) for reducing the proliferation of a cancer cell or cells. In one embodiment, there is provided a method for inducing cell death in a cancer cell or cells comprising contacting the cell(s) with the compound of formula (I). In a similar embodiment there is provided a use of the compound of formula (I) for inducing cell death in a cancer cell or cells. In one embodiment, the cancer cell may be in vivo or in vitro. The cancer cell may be a precancerous cell. In one embodiment, the cancer is Hodgkin's lymphoma, non-Hodgkin's lymphoma, B cell lymphoma, T cell lymphoma, or follicular lymphoma. In another embodiment, the B cell lymphoma is diffuse large B-cell lymphoma. In a further embodiment, the diffuse large B-cell lymphoma is a germinal center-derived diffuse large B cell lymphoma, an activated B-cell-derived (ABC) diffuse large B-cell lymphoma, or a non-germinal center diffuse large B cell lymphoma.

The compound of formula (I) can be can first be screened or selected based on their possession of certain characteristics, such as having a histone acetylation activity in vitro or in vivo. The compounds of formula (I) cane be tested by an activity assay comprising direct or indirect measurement of the activity of a HAT molecule. The assay can also be an expression assay comprising direct or indirect measurement of the expression of a HAT mRNA or protein. The various screening assays can be combined with an in vivo assay comprising measuring the effect of the compounds of formula (I) on cognitive and synaptic function in an animal model for neurodegenerative disorders, such as, but not limited to, AD or Huntington's disease. The assay can be an assay comprising measuring the effect of the test compounds on cell viability. In one embodiment, the cells are cancer cells, such as, but not limited to B-cell lymphoma cell lines, or T-cell lymphoma cell lines. The assay can be an assay comprising measuring the effect of the compounds of formula (I) on cell viability. In one embodiment, the cells are cancer cells, such as, but not limited to B-cell lymphoma cell lines, or T-cell lymphoma cell lines.

In some embodiments, the compound of formula (I) is used to treat a neurodegenerative disease in a subject in need thereof. Non-limiting examples of neurodegenerative diseases include Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases Progressive Supranuclear Palsy, Refsum's disease, Rett's syndrome, Tau-positive FrontoTemporal dementia, Tau-negative FrontoTemporal dementia, Sandhoff disease, Schilder's disease, Subacute combined degeneration of spinal cord secondary to Pernicious Anaemia, Spielmcycr-Vogt-Sjogrcn-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

An emerging view of the processes involved in memory impairment indicates that the subtlety and variability of the earliest amnesic symptoms, occurring in the absence of any other clinical signs of brain injury, could be due to discrete changes in the function of a single synapse, produced at least in part, by Aβ (*Proc Natl Acad Sci* USA, 2002. 99(20): p. 13217-21; *Neuroreport*, 1997. 8(15): p. 3213-7; *Eur J Pharmacol*, 1999. 382(3): p. 167-75; *Nature*, 2002. 416 (6880): p. 535-9; each herein incorporated by reference in its entirety).

Several evidences have indicate that LTM and synaptic plasticity rely on gene expression after an early induction phase characterized by the activation of a number of pathways (*Philos Trans R Soc Lond B Biol Sci*, 2003. 358(1432): p. 757-63; herein incorporated by reference in its entirety). More recently, a fine regulation of memory-related genes and long-term synaptic plasticity has been discovered to involve epigenetic factors (*Nat Rev Neurosci*, 2005. 6(2): p. 108-18; herein incorporated by reference in its entirety). Indeed, epigenetic modifications, such as DNA methylation and histone post-translational modifications profoundly affect the ability of polymerases to interact with the open reading frame of DNA without changing the DNA sequence itself. Deregulation of epigenetic mechanisms can lead to the disruption of memory-associated gene expression and synaptic plasticity (*Nat Rev Neurosci*, 2005. 6(2): p. 108-18;

herein incorporated by reference in its entirety), and contribute to the pathogenesis of diseases characterized by cognitive disorders, such as AD.

The process of memory storage has been described as a dialogue between genes and synapses (*Biosci Rep*, 2001. 21(5): p. 565-611; herein incorporated by reference in its entirety). The formation of long-term memory (LTM) is dependent upon gene transcription (*Nature*, 1990. 345 (6277): p. 718-21; herein incorporated by reference in its entirety), synthesis of new proteins (*Science*, 1986. 234 (4781): p. 1249-54; herein incorporated by reference in its entirety) and structural changes of the synapse (*Science*, 1983. 220(4592): p. 91-3; herein incorporated by reference in its entirety). In addition, the proper regulation of gene expression in LTM is modulated by epigenetics (*Nat Rev Neurosci*, 2005. 6(2): p. 108-18; herein incorporated by reference in its entirety). The N-terminal tails of histone proteins are known to undergo post-translational modifications, such as histone acetylation, ubiquitination, sumoylation, phosphorylation, citrullination, ADP-ribosylation, and methylation that can dictate the transitions between transcriptionally active or transcriptionally silent chromatin states (*Curr Biol*, 2004. 14(14): p. R546-5; herein incorporated by reference in its entirety). Deregulation of one of these mechanisms can lead to disruption of memory associated gene expression and cognitive disorders. Studies of the mechanisms underlying synaptic and memory dysfunction in AD have indicated central roles for the transcription factor CREB (CRE binding protein) and the coactivator CREB binding protein (CBP).

Alzheimer's disease (AD) is characterized by neuronal loss, extracellular senile plaques and intracellular neurofibrillary tangles, leading to memory loss. AD purportedly begins as a synaptic disorder produced at least in part, by Aβ (*Science* 298, 789-791 (2002); herein incorporated by reference in its entirety). Aβ-induced reduction in long-term-potentiation (LTP), a physiological correlate of synaptic plasticity that is thought to underlie learning and memory, and phosphorylation of the memory transcription factor CREB, are ameliorated by nitric oxide (NO) donors and cGMP-analogs (*J Neurosci* 25, 6887-6897 (2005); herein incorporated by reference in its entirety). Vice-versa, genetic ablation of NO-synthase 2 (NOS2) results in worsening of the AD phenotype in mice expressing mutated amyloid precursor protein (APP) (*Proceedings of the National Academy of Sciences* 103, 12867-12872 (2006); herein incorporated by reference in its entirety). These findings show that up-regulation of the NO pathway may be protective in AD.

Alzheimer's disease (AD) is a chronic progressive neurodegenerative disorder, in which the earliest stages are thought to be linked to synaptic dysfunction leading to memory disorders. In this regard, β-amyloid (Aβ) has been found to inhibit memory (*Proc Natl Acad Sci USA*, 2006. 103:8852-7; *Nat Neurosci*, 2005. 8:79 84; each herein incorporated by reference in its entirety) and its cellular model, long-term potentiation (LTP) (*Neuroreport*, 1997. 8:3213-7; *Eur J Pharmacol*, 1999. 382:167-75; *Proc Natl Acad Sci USA*, 2002. 99:13217-21; *Nature*, 2002. 416:535-9; *J Neurosci Res*, 2000. 60:65-72; *Proc Natl Acad Sci USA*, 1998. 95:6448-53; each herein incorporated by reference in its entirety).

AD is characterized neuropathologically by neuronal loss, extracellular senile plaques (SPs) and intracellular neurofibrillary tangles (NFTs). SPs are chiefly comprised of Aβ aggregates. The major component of NFTs is the microtubule binding protein tau. Clinically, AD is characterized by cognitive dysfunction and begins as a synaptic disorder that involves progressively larger areas of the brain over time (*Histol Histopathol*, 1995. 10(2): p. 509-19; herein incorporated by reference in its entirety). An emerging view of the processes involved in synaptic impairment shows that the subtlety and variability of the earliest amnesic symptoms, occurring in the absence of any other clinical signs of brain injury, can be due to discrete changes in the function of a single synapse, produced at least in part, by Aβ (*Neuroreport*, 1997. 8(15): p. 3213-7; *Eur J Pharmacol*, 1999. 382(3): p. 167-75; *Proc Natl Acad Sci USA*, 2002. 99(20): p. 13217-21; *Nature*, 2002. 416(6880): p. 535-9; herein incorporated by reference in its entirety).

Further details on Alzheimer's disease can be found in WO 2011/072243 and WO 2012/088420, each incorporated by reference herein in its entirety.

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, and Gould, P. L., *Int. J. Pharmaceutics* 1986, 33, 201-217; the contents of each are hereby incorporated by reference.

In some embodiments, a pharmaceutically acceptable salt of a compound of formula (I) is an acid addition salt, for example a hydrohalide (such as hydrochloride or hydrobromide), sulfate, or phosphate salt. In some embodiments, a pharmaceutically acceptable salt of a compound of formula (I) is a hydrochloride salt. In some embodiments, a pharmaceutically acceptable salt of a compound of formula (I) is a base addition salt, for example a sodium, potassium, calcium, or ammonium salt. In some embodiments, the base addition salt is a tetrafluoroboro salt.

In some embodiments, the methods comprise administering to the subject an effective amount of a composition comprising a compound of formula (I). In some embodiments, the subject exhibits abnormally elevated amyloid beta plaques, or elevated Tau protein levels, or accumulations of alpha-synuclein, or accumulations of lipofuscin, or accumulation of cleaved TARDBP (TDB-43) levels, or a combination thereof. In some embodiments, the Aβ protein deposit comprises an Aβ$_{40}$ isomer, an Aβ$_{42}$ isomer, or a combination thereof. In a further embodiment, the subject is afflicted with Alzheimer's disease, Lewy body dementia, inclusion body myositis, Huntington's disease, Parkinson's disease, or cerebral amyloid angiopathy. In some embodiments, the subject is afflicted with cancer. In a further embodiment, the cancer is Hodgkin's lymphoma, non-Hodgkin's lymphoma, B cell lymphoma, T cell lymphoma, or follicular lymphoma. In another embodiment, the B cell lymphoma is diffuse large B-cell lymphoma. In another embodiment, the diffuse large B-cell lymphoma is a germinal center-derived diffuse large B cell lymphoma, an activated B-cell-derived (ABC) diffuse large B-cell lymphoma, or a non-germinal center diffuse large B cell lymphoma.

The dosage administered can be a therapeutically effective amount of the composition sufficient to result in amelioration of symptoms of a neurodegenerative disease such as, but not limited to reducing inclusion bodies (e.g., amyloid beta (Aβ) protein deposits, native and phosphorylated Tau proteins, native and phosphorylated alpha-synuclein, lipofuscin, cleaved TARDBP (TDB-43), or a combination thereof), or reducing memory loss in a subject. For example, observing at least, about a 25% reduction, at least about a 30% reduction, at least about a 40% reduction, at least about a 50% reduction, at least about a 60% reduction, at least about a 70% reduction, at least about a 80% reduction, at least about a 85% reduction, at least about a 90% reduction, at least about a 95% reduction, at least about a 97% reduction, at least about a 98% reduction, or a 100% reduction in inclusion bodies or memory loss in a subject is indicative of amelioration of symptoms of a neurodegenerative disease (for example, including, but not limited to AD, Huntington's disease, and/or Parkinson's disease). This efficacy in reducing inclusion occurrence can be, for example, a measure of ameliorating symptoms of a neurodegenerative disease.

The dosage administered can be a therapeutically effective amount of the composition sufficient to result in treatment of a cancer such as, but not limited to reducing tumor size, reducing tumor growth, inhibiting tumor growth, reducing cancer cell growth, inhibiting cancer cell growth, cytotoxicity to cancer cells, reducing the number of cancerous cells, increasing the acetylation of p53 in cancer cells in a subject, increasing the acetylation of Bcl6 in cancer cells in a subject. For example, observing at least, about a 25% reduction, at least about a 30% reduction, at least about a 40% reduction, at least about a 50% reduction, at least about a 60% reduction, at least about a 70% reduction, at least about a 80% reduction, at least about a 85% reduction, at least about a 90% reduction, at least about a 95% reduction, at least about a 97% reduction, at least about a 98% reduction, or a 100% reduction in cancer cell growth or number of cancerous cells in a subject is indicative of amelioration of symptoms of a cancer (for example, including, but not limited to Hodgkin's lymphoma, non-Hodgkin's lymphoma, B cell lymphoma, T cell lymphoma, and/or follicular lymphoma). This efficacy in reducing cancer cells can be, for example, a measure of ameliorating symptoms of a cancer. In another example, observing at least, about a 10% cytotoxicity, about a 15% cytotoxicity, about a 20% cytotoxicity, about a 25% cytotoxicity, at least about a 30% cytotoxicity, at least about a 40% cytotoxicity, at least about a 50% cytotoxicity, at least about a 60% cytotoxicity, at least about a 70% cytotoxicity, at least about a 80% cytotoxicity, at least about a 85% cytotoxicity, at least about a 90% cytotoxicity, at least about a 95% cytotoxicity, at least about a 97% cytotoxicity, at least about a 98% cytotoxicity, or a 100% cytotoxicity to cancer cells is indicative of amelioration of symptoms of a cancer (for example, including, but not limited to Hodgkin's lymphoma, non-Hodgkin's lymphoma, B cell lymphoma, T cell lymphoma, and/or follicular lymphoma). This efficacy in cytotoxicity to cancer cells can be, for example, a measure of ameliorating symptoms of a cancer. In some embodiments, the dosage administered can be a therapeutically effective amount of the composition sufficient to result in sensitization of cancer cells to other cancer treatments, for example, including, but not limited to treatments for Hodgkin's lymphoma, non-Hodgkin's lymphoma, B cell lymphoma, T cell lymphoma, and/or follicular lymphoma. In some embodiments, the dosage administered can be a therapeutically effective amount of the composition sufficient to result in an increase in the effectiveness of other cancer treatments, for example, including, but not limited to treatments for Hodgkin's lymphoma, non-Hodgkin's lymphoma, B cell lymphoma, T cell lymphoma, and/or follicular lymphoma.

In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

The compound of formula (I) or composition comprising a compound of formula (I) can be administered to the subject one time (e.g., as a single injection or deposition). Alternatively, administration can be once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof.

The dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

Compounds of formula (I) can be incorporated into pharmaceutical compositions suitable for administration. Such compositions can comprise a compound of formula (I) and a pharmaceutically acceptable carrier. Thus, in some embodiments, the compounds of the invention are present in a pharmaceutical composition.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a mouse, a rat, a dog, a cat, a cow, a horse, a rabbit, a monkey, a pig, a sheep, a goat, or a human. In some embodiments, the subject is a mouse, rat or human. In some embodiments, the subject is a mouse. In some embodiments, the subject is a rat. In some embodiments, the subject is a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Scheme 1

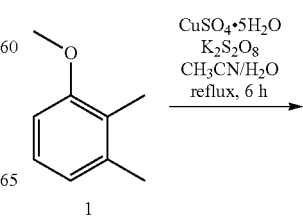

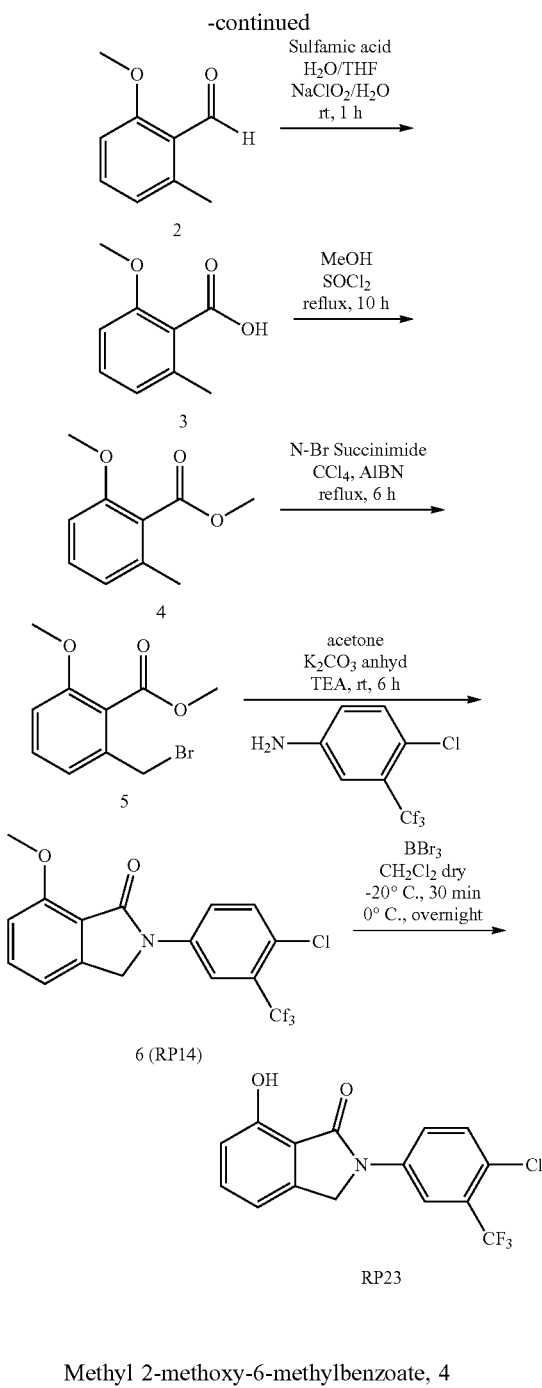

Methyl 2-methoxy-6-methylbenzoate, 4

A vigorously mixture of 1-methoxy-2,3-dimethylbenzene (1, 1.34 mL), Copper (II) Sulfate pentahydrate (2.5 g) and potassium peroxodisulfate (8.1 g) in acetonitrile/water 1:1 (70 mL) was heated at reflux for 6 h. The reaction was cooled to room temperature and was extracted with dichloromethane (3 times). The organic layer was dried over $Na_2SO_4$, filtered and evaporated to produce the desired liquid product (2) suitable for further reaction without purification. A solution of 2 (1.50 g) and sulfamic acid (1.30 g) in water (22.5 mL) and THF (11.2 mL) was stirred at room temperature and after 5 min a solution of $NaClO_2$ (1.180 g) in water (5 mL) was added. The reaction was stirred at room temperature for 1 h and then was extracted with ethyl acetate. The organic layer was separated and extracted with NaOH 1M. The aqueous solution was acidified with HCl 6N and extracted with dichloromethane. The organic layer was dried over $Na_2SO_4$, filtered and evaporated to obtain the solid product (3, 1.071 g). Thionyl chloride (0.55 mL) was added dropwise to a solution of 3 (83 mg) in methanol (0.5 mL) and the reaction was refluxed for 10 h. The methanol was removed by rotary evaporator and the residue was dilutes with water and extracted with ethyl acetate. The organic layer was washed with saturated solution of $NaHCO_3$ and then separated, dried over $Na_2SO_4$, filtered and evaporated to produce the crude product. Purification by flash chromatography gave the desired product as colorless oil (70 mg, yield 80%). $C_{10}H_{12}O_3$, MS-ESI: [M+H]$^+$=181 m/z. $^1$H-NMR: (CDCl$_3$, 300 MHz) δ 2.29 (s, 3H, —CH$_3$), 3.83 (s, 3H, —OCH$_3$), 3.92 (s, 3H, —C(=O) OCH$_3$), 6.76 (d, 1H, Jo=8.7 Hz, H-5), 6.80 (dd, 1H, Jo=7.8 Hz, Jm=0.6 Hz, H-3), 7.25 (t, 1H, Jo=7.5 Hz, Jm=8.4 Hz, H-4).

methyl 2-(bromomethyl)-6-methoxybenzoate, 5

N-Bromosuccinimide (250 mg) and catalytic amount of 2,2'-Azobis(2-methylpropionitrile) was added to a solution of 4 (252 mg) in carbon tetrachloride (3.5 mL). The reaction was heated to reflux in the present of visible light for 6 h. After cooling to room temperature the reaction was filtered and the filtrate was evaporated. The residue was diluted with water and extracted with diethyl ether. The organic layer was dried over $Na_2SO_4$, filtered and evaporated. The obtained residue was purified by flash chromatography to produce the desired product (195 mg, yield 60%). $C_{10}H_{11}BrO_3$, MS-ESI: [M+H]$^+$=259 m/z, [M+H]$^+$+2=261 m/z. $^1$H-NMR: (CDCl$_3$, 300 MHz) δ 3.83 (s, 3H, —OCH$_3$), 3.94 (s, 3H, —C(=O) OCH$_3$), 4.48 (s, 2H, —CH$_2$Br), 6.89 (d, 1H, Jo=8.4 Hz, H-5), 7.00 (d, 1H, Jo=7.5 Hz, H-3), 7.33 (t, 1H, Jo=8.1 Hz, H-4).

2-(4-chloro-3-(trifluoromethyl)phenyl)-7-methoxyisoindolin-1-one, 6

A solution of 5 (130 mg), 4-chloro-3-(trifluoromethyl) aniline (98 mg), triethylamine (105 μL) and K$_2$CO$_3$ (10 mg) was refluxed in acetone (1 mL) for 6 h. The reaction was extracted with ethyl acetate and water. The organic layer was dried over $Na_2SO_4$, filtered and evaporated. The crude product was purified by flash chromatography (dichloromethane/ethyl acetate, 9.5:0.5) to obtain the desired product (65 mg, yield 80%). $C_{16}H_{11}ClF_3NO_2$, MS-ESI: [M+H]$^+$=342 m/z. $^1$H-NMR: (CDCl$_3$, 300 MHz) δ 4.01 (s, 3H, —OCH$_3$), 4.80 (s, 2H, —CH$_2$), 6.95 (d, 1H, Jo=8.1 Hz, H-4), 7.08 (d, 1H, Jo=7.2 Hz, H-6), 7.52 (d, 1H, Jo=9.0 Hz, H-5'), 7.56 (t, 1H, Jo=8.0 Hz, H-5), 8.06 (dd, 1H, Jo=9.2 Hz, Jm=2.7 Hz, H-6'), 8.23 (d, 1H, Jm=2.7 Hz, H-2').

2-(4-chloro-3-(trifluoromethyl)phenyl)-7-hydroxyisoindolin-1-one, RP23

Boron tribromide (1M in dichloromethane, 0.4 mL) was added dropwise to a solution of 6 (34 mg) in 1 mL of dichloromethane at −20° C. The reaction was stirred for 30 min at −20° C. and overnight at 0° C. The mixture was poured into ice-cold water and stirred for 30 min at room temperature. The product was filtered and washed with water to obtain the desired product (30 mg, yield: 89%). $C_{15}H_9ClF_3NO_2$, MS-ESI: [M+H]$^+$=328 m/z. $^1$H-NMR: (CDCl$_3$, 300 MHz) δ 4.86 (s, 2H, —CH$_2$), 6.93 (dd, 1H, Jo=8.7 Hz, Jm=0.6 Hz, H-4), 7.02 (dd, 1H, Jo=7.8 Hz, Jm=0.6 Hz, H-6), 7.51 (t, 1H, Jo=8.0 Hz, H-5), 7.55 (d, 1H, Jo=9.0 Hz, H-5'), 8.04 (dd, 1H, Jo=8.7 Hz, Jm=2.7 Hz, H-6'), 8.14 (d, 1H, Jm=2.7, H-2'), 8.57 (s, 1H, sc. D$_2$O, OH).

Example 2

Scheme 2

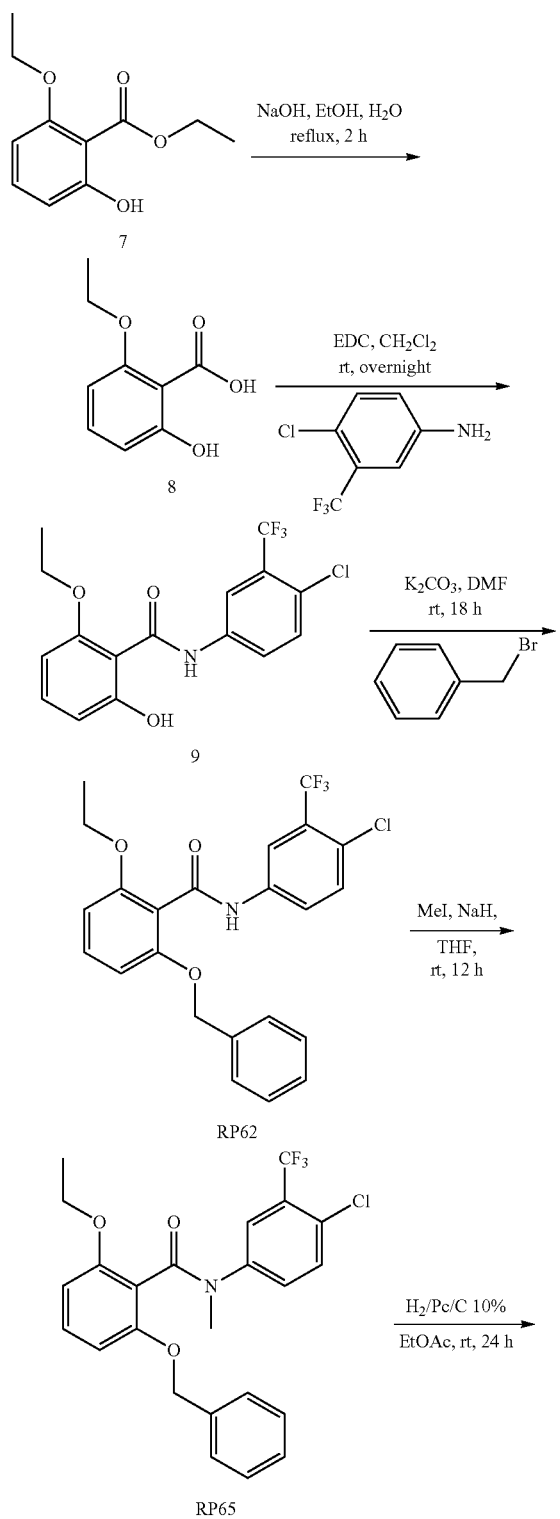

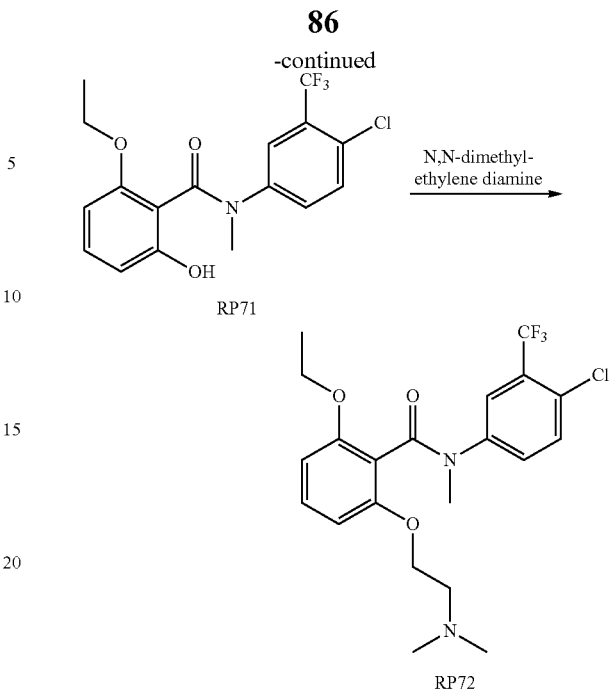

2-ethoxy-6-hydroxybenzoic Acid, 8

NaOH 1N (6 mL) was added dropwise to a solution of ethyl 2-ethoxy-6-hydroxybenzoate (7, 1 g) in ethanol (3 mL). The reaction was refluxed for 2 h and then concentrated and extracted with water and dichloromethane (3 times). The aqueous solution was separated and acidified to pH=1 to obtain the precipitation of the product (660 mg, yield: 76%), which was filtrated and washed with water. C$_9$H$_{10}$O$_4$, MS-ESI: [M+H]$^+$=183 m/z. $^1$H-NMR: (CDCl$_3$, 300 MHz) δ 1.57 (t, 3H, Jv=7.2 Hz, —CH$_2$CH$_3$), 4.32 (q, 2H, Jv=7.2 Hz, —CH$_2$CH$_3$), 6.47 (d, 1H, Jo=8.4 Hz, H-5), 6.71 (d, 1H, Jo=8.4 hz, H-3), 7.39 (t, 1H, Jo=8.4 Hz, H-4), 11.60 (s, 1H, C(=O)OH), 12.16 (s, 1H, OH).

N-(4-chloro-3-(trifluoromethyl)phenyl)-2-ethoxy-6-hydroxybenzamide, 9

N-(3-Dimethylaminopropyl)-N'-ethylcarbodiimide hydrochloride (900 mg) was added gradually to a solution of 8 (660 mg) and 4-chloro-3-(trifluoromethyl)aniline (780 mg) in dichloromethane (5 mL) at 0° C. The reaction was stirred at room temperature overnight then filtered and the precipitate was crystallized from methanol (608 mg, yield: 67%). C$_{16}$H$_{13}$ClF$_3$NO$_3$, MS-ESI: [M+H]$^+$=360 m/z. $^1$H-NMR: (CDCl$_3$, 300 MHz) δ 1.65 (t, 3H, Jv=6.9 Hz, —CH$_2$CH$_3$), 4.27 (q, 2H, Jv=6.9 Hz, —CH$_2$CH$_3$), 6.44 (d, 1H, Jo=8.4 Hz, H-5), 6.67 (d, 1H, Jo=8.4 Hz, H-3), 7.32 (t, 1H, Jo=8.4 Hz, H-4), 7.48 (d, 1H, Jo=8.7 Hz, H-5'), 7.77 (dd, 1H, Jo=8.7 Hz, Jm=2.4 Hz, H-6'), 7.91 (d, 1H, Jm=2.1 Hz, H-2'), 10.66 (s, 1H, —C(=O)NH), 13.29 (s, 1H, OH).

2-(benzyloxy)-N-(4-chloro-3-(trifluoromethyl)phenyl)-6-ethoxybenzamide, RP62

Benzyl bromide (24 μL) was added to a suspension of 9 (70 mg) and K$_2$CO$_3$ (36 mg) in DMF (1.5 mL). The reaction was stirred at room temperature and after 18 h the solvent was evaporated under vacuum and the residue partitioned between saturated aqueous solution of NaHCO$_3$ and ethyl acetate. The organic layer was separated, dried over Na$_2$SO$_4$, filtered and evaporated. Purification by flash chromatography (Hexane/Ethyl acetate, 8:2) gave the desired product (50 mg, yield: 60%). C$_{23}$H$_{19}$ClF$_3$NO$_3$, MS-ESI: [M−H]$^-$=448 m/z, [M+H]$^+$=450 m/z. $^1$H-NMR: (DMSO-d$_6$, 400 MHz) δ 1.20 (t, 3H, Jv=6.9 Hz, —CH$_2$—CH$_3$), 4.02 (q, 2H, Jv=6.9 Hz, —CH$_2$—CH$_3$), 5.10 (s, 2H, CH$_2$-Ph), 6.70 (d, 1H, Jo=7.6 Hz, H-3), 6.74 (d, 1H, Jo=8.4 Hz, H-5), 7.12-7.34 (m, 6H), 7.49 (d, 1H, Jo=9.2 Hz, H-5'), 7.90 (dd, 1H, Jo=8.8 Hz, Jm=2.4 Hz, H-6'), 8.25 (d, 1H, Jm=2.4 Hz, H-2'), 10.67 (s, 1H, NH).

2-(benzyloxy)-N-(4-chloro-3-(trifluoromethyl)phenyl)-6-ethoxy-N-methylbenzamide, RP65

Iodomethane (20 μL) was added to suspension of RP62 (70 mg) and NaH (60% oil disp., 9 mg) in THF (2 mL) at room temperature. The reaction was stirred and after 12 h the solvent was evaporated and the residue was diluted with HCl 1M and extracted with dichloromethane (2 times). The organic layer was dried over Na$_2$SO$_4$, filtered and evaporated obtaining the desired product (80 mg, yield: 30%). C$_{24}$H$_{21}$ClF$_3$NO$_3$, MS-ESI: [M+H]$^+$=464 m/z. $^1$H-NMR: (CDCl$_3$, 400 MHz) δ 1.40 (dt, 3H, Jv=7.2 Hz, —CH$_2$CH$_3$), 3.40 (s, 3H, N—CH$_3$), 3.90 (dd, 1H, Jv=7.2 Hz, —CH$_2$CH$_3$), 4.03 (dd, 1H, Jv=7.2, —CH$_2$CH$_3$), 4.90 (d, 1H, Jv=12 Hz, CH$_2$-Ph), 5.05 (d, 1H, Jv=12 Hz, CH$_2$-Ph), 6.33 (dd, 2H, Jo=7.6 Hz, H-3 and H-5), 7.04 (t, 1H, Jo=8.8 Hz, H-4), 7.11 (dd, 1H, Jm=2.8 Hz, Jo=9.0 Hz, H-6'), 7.18 (d, 1H, Jo=8.8 Hz, H-5'), 7.26-7.38 (m, 5H), 7.46 (d, 1H, Jm=2.4 Hz, H-2').

N-(4-chloro-3-(trifluoromethyl)phenyl)-2-ethoxy-6-hydroxy-N-methylbenzamide, RP71

A solution of RP65 (80 mg) in ethyl acetate was hydrogenated at atmospheric pressure over 10% Pd/C (19 mg) for 24 h. The mixture was filtered and the filtrate was evaporated to give the product (60 mg, yield: 94%). C$_{17}$H$_{15}$ClF$_3$NO$_3$. $^1$H-NMR: (CDCl$_3$, 400 MHz) δ 1.20-1.22 (m, 3H, —CH$_2$CH$_3$), 3.42 (s, 3H, N—CH$_3$), 3.54-3.60 (m, 2H, —CH$_2$CH$_3$), 6.06 (d, 1H, Jo=8.4 Hz, H-3), 6.49 (d, 1H, Jo=8.4 Hz, H-5), 7.02-7.06 (m, 2H, H-6' and H-5'), 7.02-7.08 (m, 1H, H4), 7.40-7.42 (m, 1H, H-2'), 7.68 (s, 1H, OH).

Example 3

Scheme 3

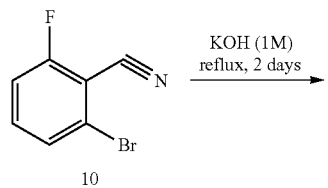

10

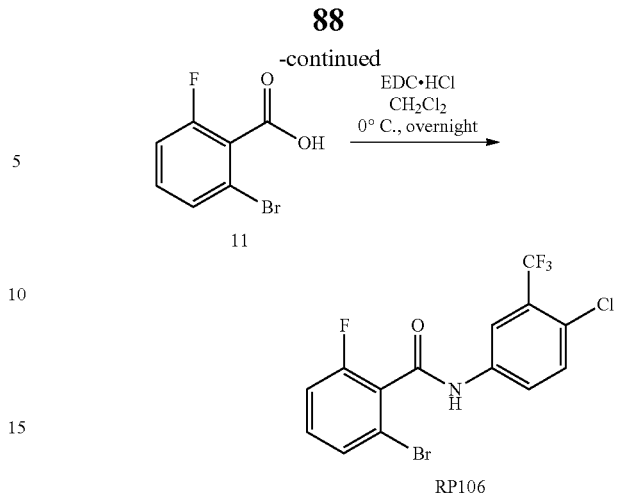

2-bromo-6-fluorobenzoic Acid, 11

A solution 2-bromo-6-fluorobenzonitrile 10 in KOH 1M (25 mL) was stirred to reflux for 2 day. The reaction was cooled to room temperature and the HCl concentrate was added to pH=2-3. The aqueous solution was extracted with ethyl acetate (3 times). The organic layer was separated, dried and evaporated to obtain the desired product (126 mg, yield: 95%). C$_7$H$_4$BrFO$_2$, MS-ESI: [M−H]$^-$=218 m/z. $^1$H-NMR: (CDCl$_3$, 400 MHz) δ 7.14 (t, 1H, Jo=8.4 Hz, H-4), 7.29-7.35 (m, 1H, H-3), 7.45 (d, 1H, H-5).

2-bromo-N-(4-chloro-3-(trifluoromethyl)phenyl)-6-fluorobenzamide, RP106

N-(3-Dimethylaminopropyl)-N'-ethylcarbodiimide hydrochloride (EDC.HCl, 74 mg) was added to a solution of 11 (65 mg) in dichloromethane (0.5 mL) at 0° C., and then 4-chloro-3-(trifluoromethyl)aniline (64 mg) was added. The solution was stirred at room temperature for 24 h. The solvent was evaporated and the residue was crystallized from methanol (55 mg, yield: 47%). C$_{14}$H$_7$BrClF$_4$NO, MS-ESI: [M−H]$^-$=394 m/z. $^1$H-NMR: (CDCl$_3$, 400 MHz) δ 7.10 (t, 1H, Jo=8.4 Hz, H-4), 7.30-7.40 (m, 3H, H-3, H-6' and H-5'), 7.02-7.08 (m, 1H, H-5), 7.40-7.42 (m, 1H, H-2'), 7.60 (s, 1H, NH).

Example 4

Scheme 4

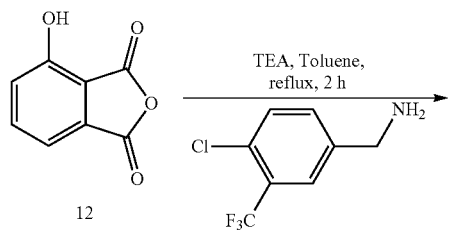

12

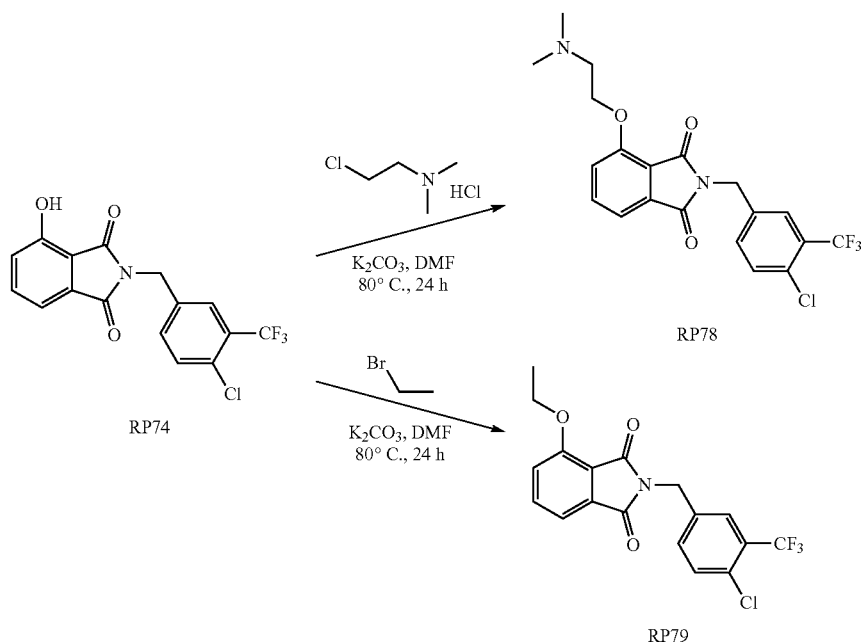

2-(4-chloro-3-(trifluoromethyl)benzyl)-4-hydroxy-isoindoline-1,3-dione, RP74

A solution of 12 (100 mg) and 4-chloro-3-(trifluoromethyl)benzylamine (111 L) in acetic acid (3 mL) was heated to reflux for 2 h. The solvent was evaporated and the residue was extracted with dichloromethane and water. The organic layer was dried over Na2SO4, filtered and evaporated. The crude product was purified by flash chromatography (dichloromethane/methanol, 9.9:0.1)(89 mg, yield: 45%). $C_{16}H_9ClF_3NO_3$, MS-ESI: $[M-H]^-=354$ m/z. $^1$H-NMR: (CDCl$_3$, 400 MHz) δ 4.79 (s, 2H, CH$_2$-Ph), 7.16 (d, 1H, Jo=8.0 Hz, H-7), 7.38 (d, 1H, Jo=6.8 Hz, H-5), 7.45 (d, 1H, Jo=8.4 Hz, H-5'), 7.52 (dd, 1H, Jo=7.6 Hz, Jm=2.0 Hz, H-6'), 7.51-7.53 (brs, 1H, OH), 7.58 (dd, 1H, Jo=8.8 Hz, Jo=8.4 Hz, H-6), 7.72 (d, 1H, Jm=2.0 Hz, H-2').

2-(4-chloro-3-(trifluoromethyl)benzyl)-4-(2-(dimethylamino)ethoxy)isoindoline-1,3-dione, RP78

A suspension of RP74 (89 mg), 2-Chloro-N,N-dimethylethylamine hydrochloride (40 mg), and K$_2$CO$_3$ (86 mg) in DMF (2 mL) was stirred at 80° C. for 24 h. The reaction mixture was diluted with dichloromethane and washed with water (3 times). The organic layer was dried over Na$_2$SO$_4$, filtered and evaporated. The crude product was purified by flash chromatography (methanol/ethyl acetate, 5:5) to provide the desired product (40 mg, yield: 40%). $C_{20}H_{18}ClF_3N_2O_3$, MS-ESI: $[M+H]^+=427$ m/z. $^1$H-NMR: (CDCl$_3$, 400 MHz) δ 2.37 (s, 6H, —N(CH$_3$)$_2$), 2.83 (t, 2H, Jv=6.0 Hz, —OCH$_2$CH$_2$—N—), 4.26 (t, 2H, Jv=6.0 Hz, —OCH$_2$CH$_2$—N—), 4.78 (s, 2H, CH$_2$-Ph), 7.18 (d, 1H, Jo=8.0 Hz, H-7), 7.42 (d, 1H, Jo=8.4 Hz, H-5), 7.43 (d, 1H, Jo=6.8 Hz, H-5'), 7.53 (dd, 1H, Jo=8.4 Hz, Jo=8.0 Hz, Jm=2.0 Hz, H-6'), 7.63 (dd, 1H, Jo=8.8 Hz, Jo=8.4 Hz, H-6), 7.72 (d, 1H, Jm=2.0 Hz, H-2').

2-(4-chloro-3-(trifluoromethyl)benzyl)-4-ethoxy-isoindoline-1,3-dione, RP79

A suspension of RP74 (95 mg), bromoethane (23 μL), and K$_2$CO$_3$ (93 mg) in DMF (2.5 mL) was stirred at 80° C. for 24 h. The reaction mixture was diluted with dichloromethane and washed with water (3 times). The organic layer was dried over Na$_2$SO$_4$, filtered and evaporated. The crude product was purified by flash chromatography (hexane/ethyl acetate, 6:4) to provide the desired product (95 mg, yield: 93%). $C_{18}H_{13}ClF_3NO_3$, MS-ESI: $[M+H]^+=384$ m/z. $^1$H-NMR: (CDCl$_3$, 400 MHz) δ 1.50 (t, 3H, Jv=7.2 Hz, —CH$_2$CH$_3$), 4.24 (q, 2H, Jv=7.2 Hz, —CH$_2$CH$_3$), 4.78 (s, 2H, CH$_2$-Ph), 7.16 (d, 1H, Jo=8.0 Hz, H-7), 7.40 (d, 1H, Jo=7.2 Hz, H-5), 7.41 (d, 1H, Jo=8.4 Hz, H-5'), 7.54 (dd, 1H, Jo=8.4 Hz, Jm=2.0 Hz, H-6'), 7.62 (dd, 1H, Jo=7.2 Hz, H-6), 7.72 (d, 1H, Jm=2.0 Hz, H-2').

Example 5

Scheme 5

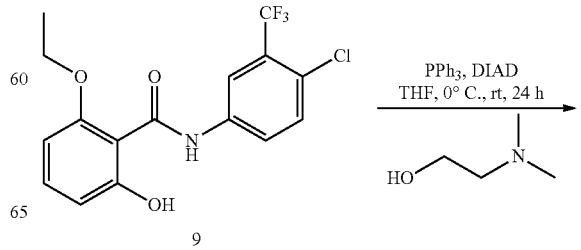

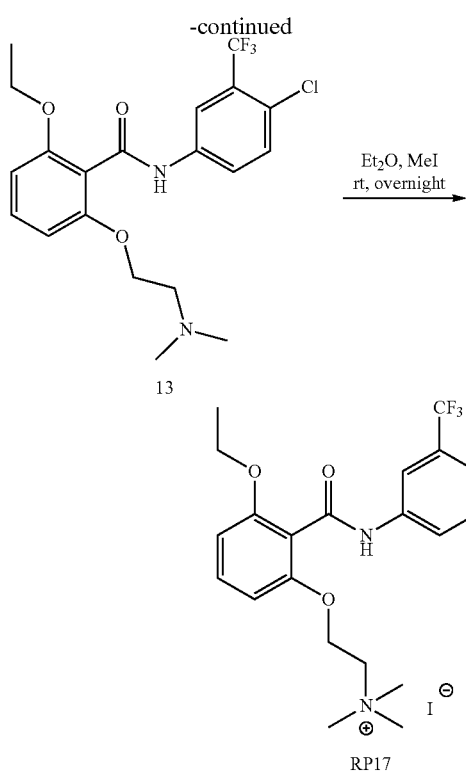

N-(4-chloro-3-(trifluoromethyl)phenyl)-2-(2-(dimethylamino)ethoxy)-6-ethoxybenzamide, 13

Diisopropyl azodicarboxylate (128 µL) was added to a solution of 9, 2-Dimethylaminoethanol (65 µL) and triphenylphosphine (170 mg) in THF (2.5 mL) at 0° C. The solution was stirred at room temperature overnight. The solvent was evaporated and the residue was diluted in ethyl acetate and washed with water and brine (3 times). The organic layer was dried over $Na_2SO_4$, filtered and evaporated. Purification by flash chromatography (dichloromethane/methanol, 9.4:0.6) gave the desired colorless oil. $C_{20}H_{22}ClF_3N_2O_3$, MS-ESI: $[M+H]^+=431$ m/z. $^1$H-NMR: ($CDCl_3$, 400 MHz) δ 1.39 (t, 3H, Jv=6.9 Hz, O—$CH_2\underline{CH_3}$), 2.25 (s, 6H, $N(CH_3)_2$), 2.65 (t, 2H, Jv=5.4 Hz, —$OCH_2\underline{CH_2}N$—), 4.09 (q, 2H, Jv=6.9 Hz, —$O\underline{CH_2}CH_3$), 4.19 (t, 2H, Jv=5.4 Hz, —$O\underline{CH_2}CH_2N$—), 6.59 (d, 1H, Jo=8.7 Hz, H-3), 6.60 (d, 1H, Jo=8.7 Hz, H-5), 7.28 (t, 1H, Jo=8.4 Hz, Jo=8.7 Hz, H-4), 7.46 (d, 1H, Jo=8.4 Hz, H-5'), 7.80 (s, 1H, H-2'), 7.98 (d, 1H, Jo=8.1, H-6'), 8.71 (s, 1H, NH).

2-(2-((4-chloro-3-(trifluoromethyl)phenyl)carbamoyl)-3-ethoxyphenoxy)-N,N,N-trimethylethan-1-aminium Iodide, RP17

Iodomethane (21 µL) was added to a solution of 13 (86 mg) in diethyl ether (1.2 mL) and the reaction was stirred at room temperature overnight. The white precipitate was collected by filtration and dried under vacuum to give the desired product (75 mg, yield: 65%). $C_{21}H_{25}ClF_3IN_2O_3$, MS-ESI: $[M]^+=445$ m/z. $^1$H-NMR: (DMSO-$d_6$, 400 MHz) δ 1.22 (t, 3H, Jv=7.1 Hz, —$OCH_2\underline{CH_3}$), 3.04 (s, 9H, —$N(CH_3)_3$), 3.64 (m, 2H, —$OCH_2\underline{CH_2}N$), 4.06 (q, 2H, Jv=6.9 Hz, —$O\underline{CH_2}CH_3$), 4.45 (m, 2H, —$O\underline{CH_2}CH_2N$), 6.79 (dd, 2H, Jo=8.7 Hz, Jm=2.0 Hz, H-4 and H-6), 7.39 (t, 1H, Jo=8.4 Hz, H-5), 7.67 (d, 1H, Jo=8.7 Hz, H-5'), 7.86 (d, 1H, Jo=8.1 Hz, H-6'), 8.27 (d, 1H, Jm=2.4 Hz, H-2'), 10.67 (s, 1H, NH).

Example 6

Isatoic anhydride was reacted with 4-chloro-3-trifluoromethyl aniline to provide RP 95:

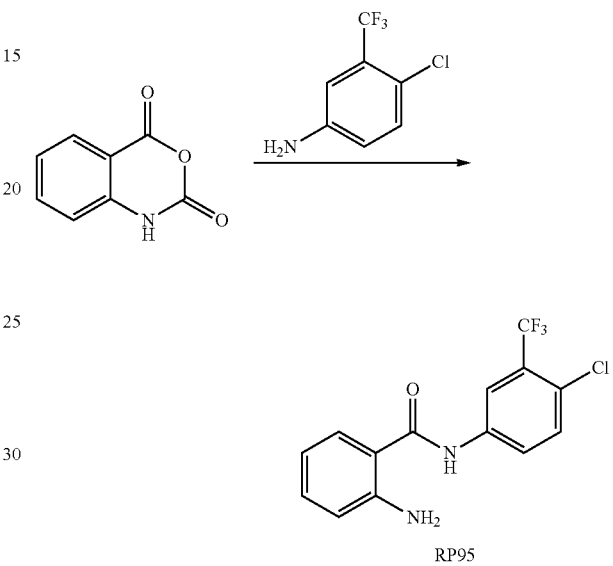

Example 7

2-bromo benzoic acid was reacted with 4-chloro-3-trifluoromethyl aniline to provide RP 101. RP 102 was obtained via reaction of RP 101 with N, N-dimethylethane diamine.

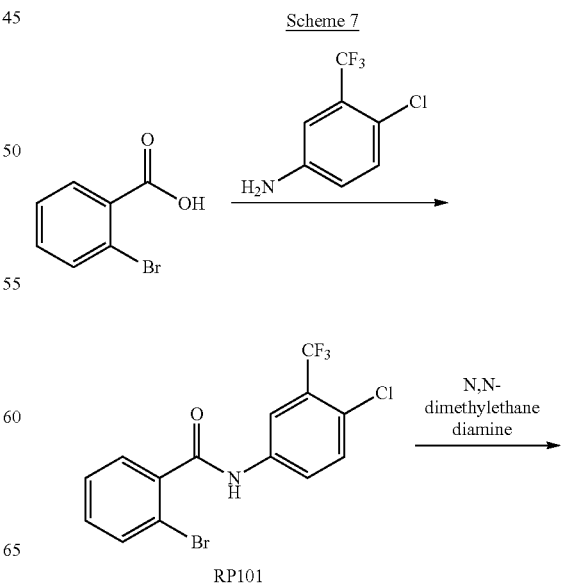

-continued

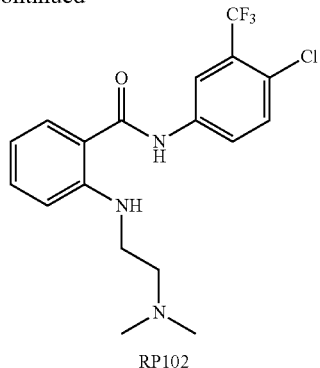

RP102

Example 8

In vitro measurements of pCAF enzymatic activity were performed with radioassay in which active pCAF (recombinant protein expressed in *E. Coli*, Millipore) was used to acetylate core histones (chicken erythrocyte histones, Millipore) in vitro with tracer levels of tritiated acetyl-CoA (Perkin Elmer) as the acetyl donor. Results are shown in FIG. 1.

Example 9

HAT activator YF2 (U.S. patent application Ser. No. 13/493,490; herein incorporated by reference in its entirety) was tested in the YAC128 Huntington disease model. Animals were treated with YF2 (5 mg/kg, i.p, daily) or vehicle, starting at the age of 2 months. Consistent with previously published findings, 4 month old male YAC128 mice fell off of the accelerating rotarod significantly sooner (and hence stay on the rod for a shorter period of time) than control littermates (ANOVA, $F(1,22)=8.768$; $p=0.0072$). Post-hoc analysis (Fisher PLSD) in male mice revealed that although YAC128 mice treated with vehicle performed significantly worse than WT mice treated with vehicle ($p=0.0021$), this significance was lost once YAC128 mice were treated with YF2 (WT mice treated with YF2 ($p=0.1946$) or WT mice treated with vehicle ($p=0.0792$). At 6 months of age, post-hoc analysis in female mice revealed a similar effect: although YAC128 mice treated with vehicle performed significantly worse than WT mice treated with vehicle ($p=0.0100$), this significance was lost once YAC128 mice were treated with YF2 (WT mice treated with YF2 ($p=0.12734$) or WT mice treated with vehicle ($p=0.1690$)).

Example 10: Histone Acetyl Transferase Activators as a Therapeutic Agent for Cancer and Inflammatory Diseases Modulation of the acetylation state of histones, transcription factors, and other regulatory proteins is known to influence their activity within cancer and inflammatory cells. The acetylation state of a protein is controlled by the activity of two main groups of enzymes, histone deacetylases (HDAC) and histone acetyl transferases (HAT). The HDAC removes acetyl-groups while the HATs transfer acetyl-groups to the protein of interest. Classically, modulation of acetylation status is known to influence the condensation of chromatin. In cancer, histones are deacetylated maintaining a condensed chromatin structure, and a transcriptionally silenced state. This transcriptional inactivation is mediated by HDACs which remove acetyl groups from histone tails, maintain a condensed chromatic structure. Inhibitors of HDACs help maintain transcriptionally active chromatin, theoretically allowing for expression of tumor suppressor genes. Two HDAC inhibitors have been approved for the treatment of cancer, including vorinostat and romidepsin, currently FDA approved for the treatment of cutaneous T-cell lymphoma and peripheral T-cell lymphoma.

Since these approvals, the pharmacology of this class of drugs have been extensively studied. One observation that has evolved is that histones are not the only targets of acetylation. It is now accepted that post-translational acetylation of intracellular proteins such as tumor suppressors (p53) and oncogenes (Bcl6) plays a critical role in influencing their activity. It has been established that there is a network of proteins and enzymes that can be modified by acetylation, now collectively referred to as the acetylome. It has been shown that modulation of key intracellular proteins with HDAC inhibitors can lead to profound effects in lymphoma cell lines, in mouse models of lymphoma and in patients with drug-resistant lymphoma. Treatment with HDAC inhibitors, like vorinostat, can inactivate the oncogene, Bcl6, while simultaneously activating the tumor suppressor, p53. The tumor suppress p53 plays an important role in many cancers, and mutations in p53 are critical in the development of many cancers. Enhancement of p53 activity through acetylation protects the tumor suppressor from proteosomal degradation and stimulates induction of apoptosis.

It has also recently been recognized that many patients with diffuse large B-cell lymphoma and follicular lymphoma, the two most common subtypes of lymphoma, harbor inactivating mutations in one of two families of HAT enzymes, CREBBP and p300. These mutations portend a more aggressive phenotype of disease, and shortened survival in mouse models. These mutations are mostly heterozygous, suggesting that the normal haploallele may still be amenable to modification, potentially reversing this malignant phenotype. These mutations have also been identified in B-cell derived acute leukemias.

Currently, there are no clinically approved drugs targeting HATs. Given the clinical success of HDAC inhibitors, and the specific HAT mutations in lymphomas, HAT activators may modify the acetylation state of the proteome and may therefore represent a rational therapeutic target for cancer. Furthermore, combined targeting of acetylation through HAT activation and HDAC inhibition may induce profound post-translational modification of key regulatory proteins and 'acetylation stress,' leading to the induction of programmed cell death.

Figure 6A:
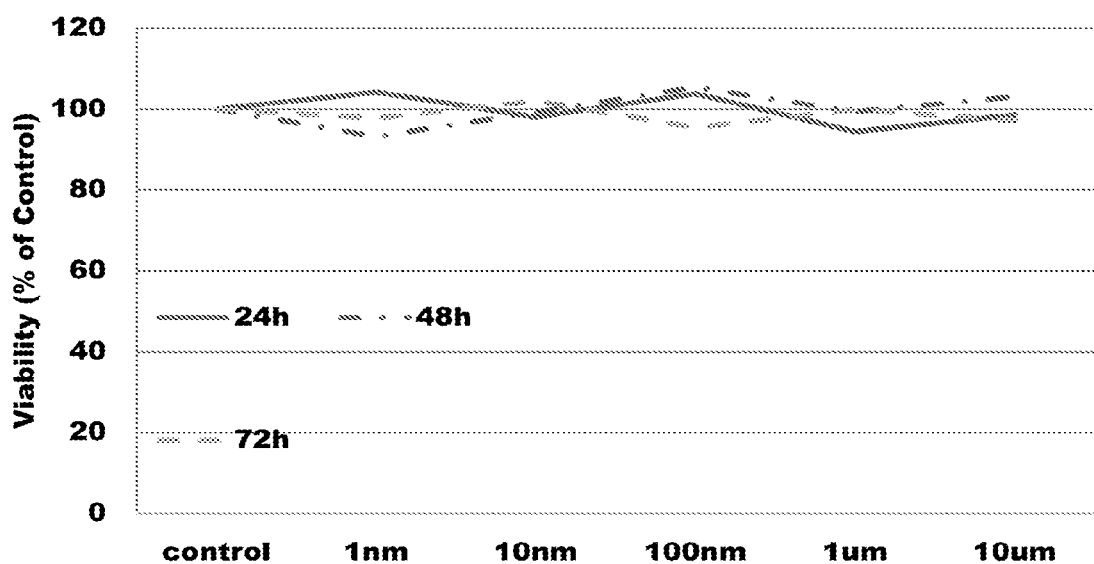
FIGS. 6A-B shows the effect relationship of RP14 for a panel of lymphoma cell lines. Cytotoxicity was evaluated using Cell-titer Glo Reagent (Promega). Cells were seeded at $0.3 \times 10^6$ cell/mL and treated with increasing concentrations of RP14 as indicated. Cytotoxicity was measured at 24 (blue line), 48 (red line), and 72 (green line) hours and compared to untreated cells. Cell lines Ly7 (A), and Su-DHL6 (B) were treated.
Figure 6B:
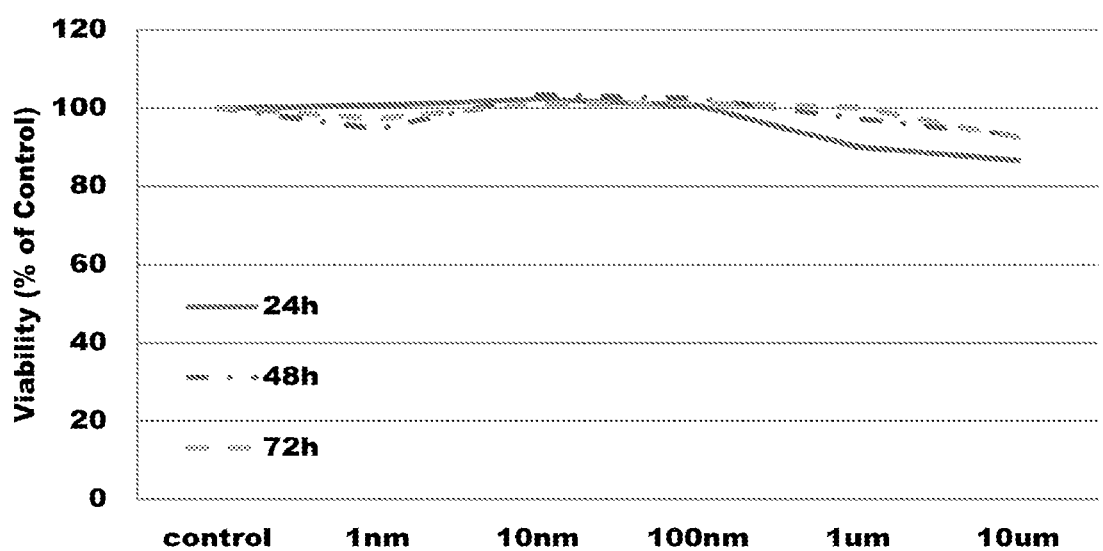
Figure 7A:
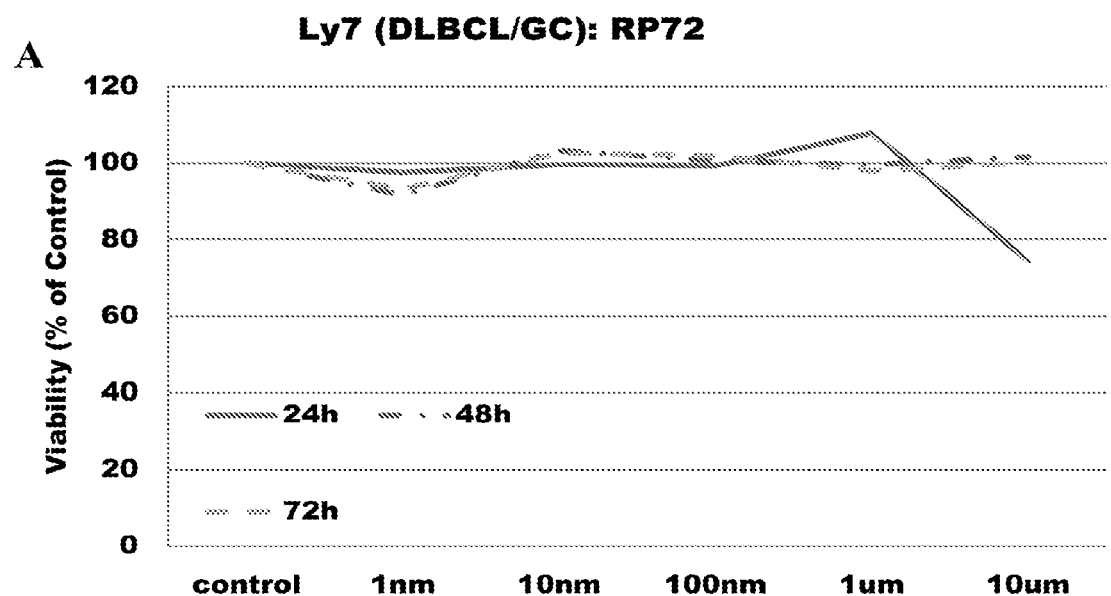
FIGS. 7A-B shows the effect relationship of RP72 for a panel of lymphoma cell lines. Cytotoxicity was evaluated using Cell-titer Glo Reagent (Promega). Cells were seeded at $0.3 \times 10^6$ cell/mL and treated with increasing concentrations of RP72 as indicated. Cytotoxicity was measured at 24 (blue line), 48 (red line), and 72 (green line) hours and compared to untreated cells. Cell lines Ly7 (A), and Su-DHL6 (B) were treated.
Figure 7B:
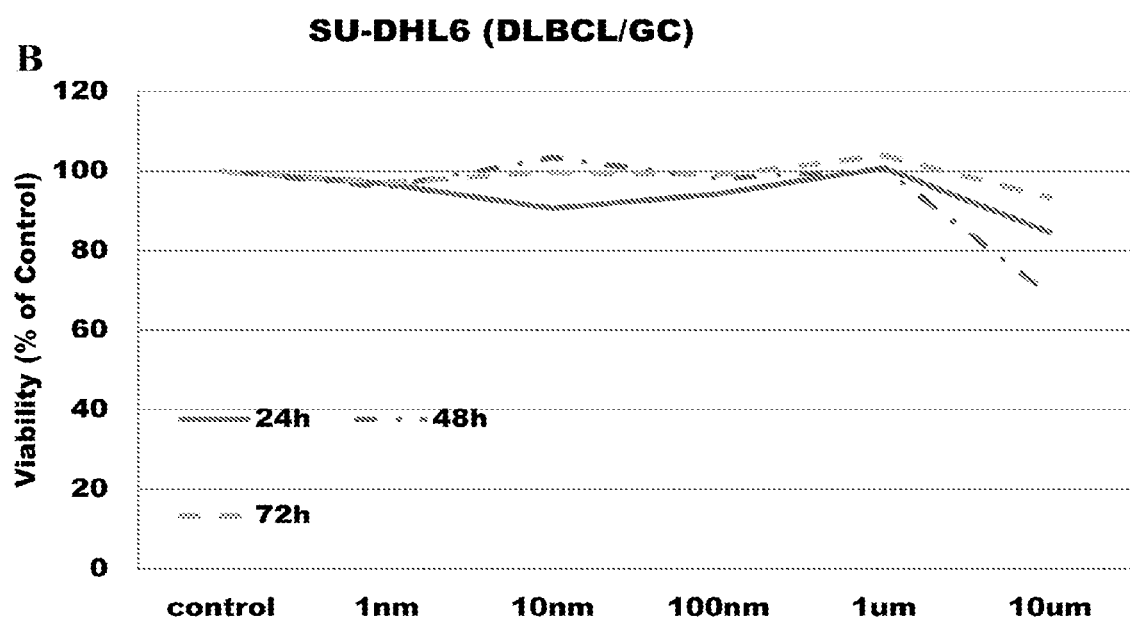
Figures 8A, 8B, 8C:
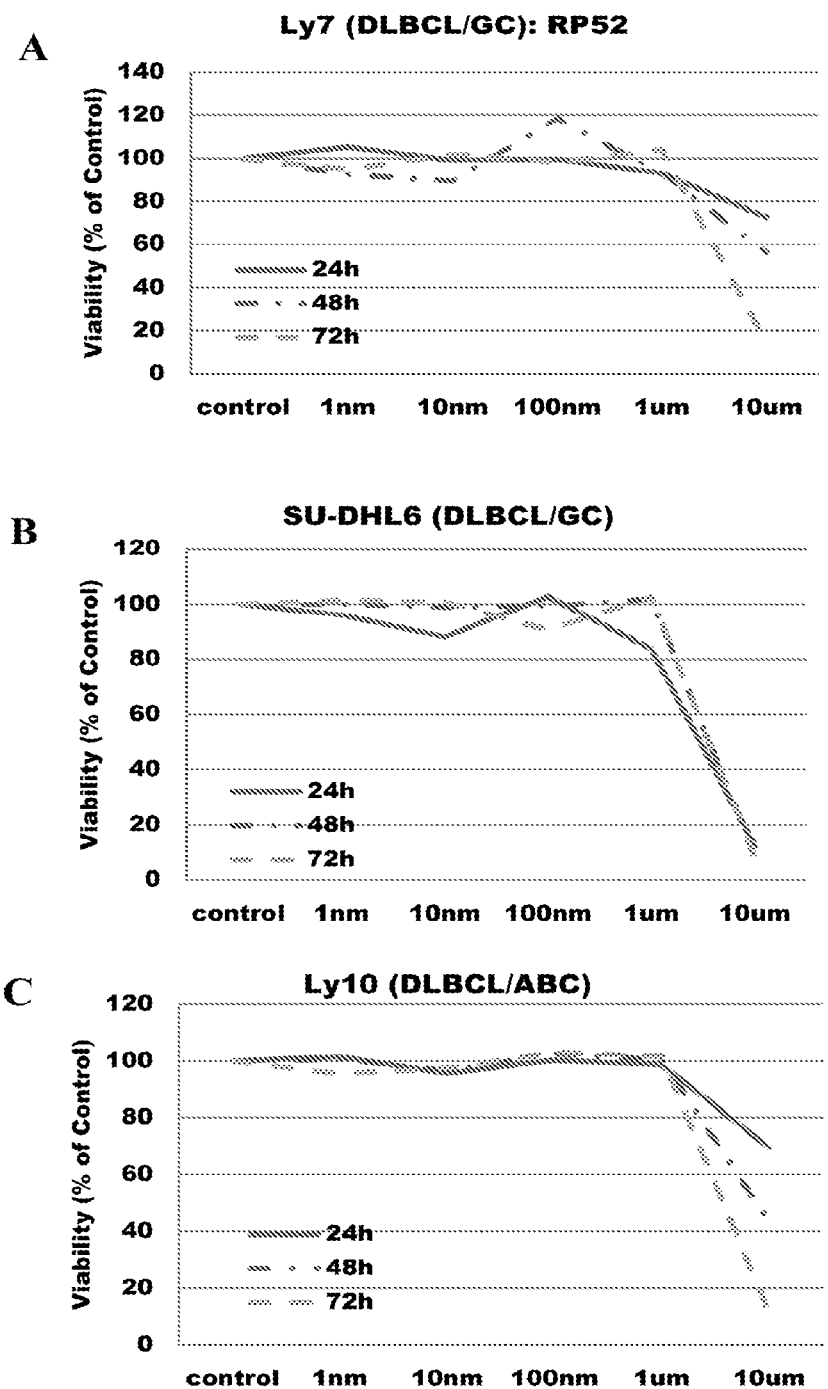
FIGS. 8A-C shows the effect relationship of RP52 for a panel of lymphoma cell lines. Cytotoxicity was evaluated using Cell-titer Glo Reagent (Promega). Cells were seeded at $0.3 \times 10^6$ cell/mL and treated with increasing concentrations of RP52 as indicated. Cytotoxicity was measured at 24 (blue line), 48 (red line), and 72 (green line) hours and compared to untreated cells. Cell lines Ly7 (A), Su-DHL6 (B), and Ly10 (C) were treated.
Figures 9A, 9B, 9C:
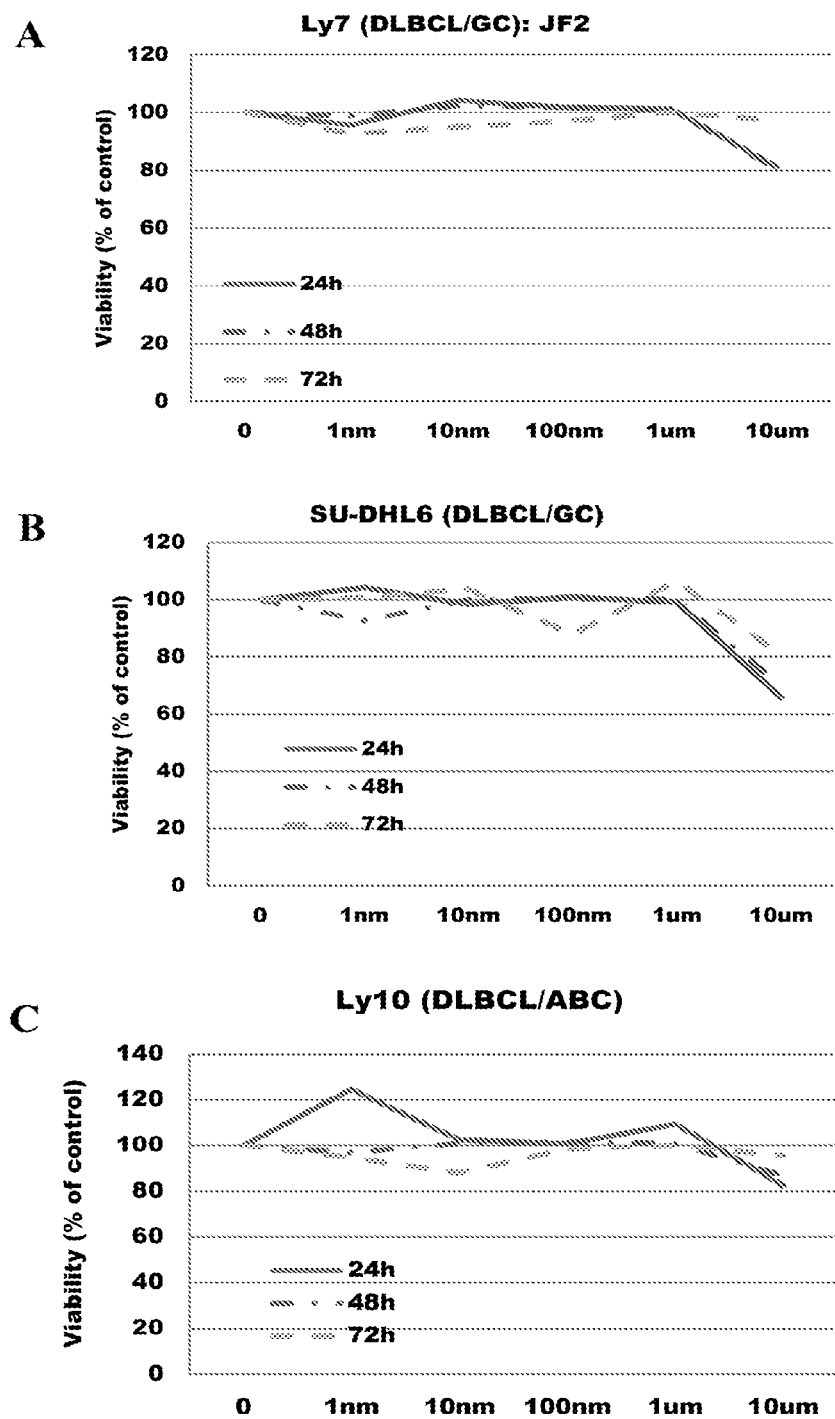
FIGS. 9A-C shows the effect relationship of JF2 for a panel of lymphoma cell lines. Cytotoxicity was evaluated using Cell-titer Glo Reagent (Promega). Cells were seeded at $0.3 \times 10^6$ cell/mL and treated with increasing concentrations of JF2 as indicated. Cytotoxicity was measured at 24 (blue line), 48 (red line), and 72 (green line) hours and compared to untreated cells. Cell lines Ly7 (A), Su-DHL6 (B), and Ly10 (C) were treated.
Figure 10A:
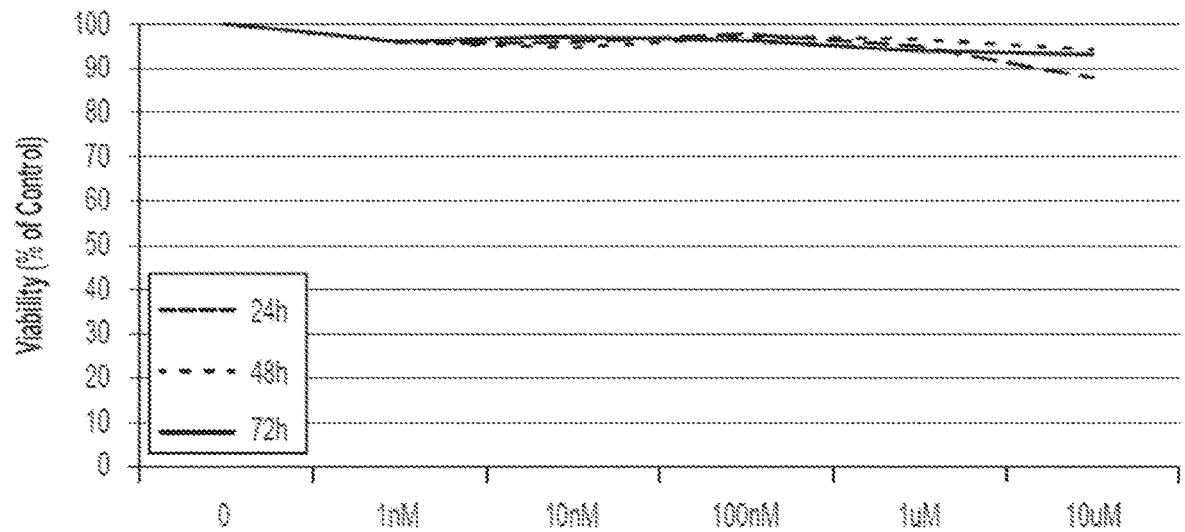
FIGS. 10A-B shows the effect relationship of RP14 for a panel of lymphoma cell lines. Cytotoxicity was evaluated using Cell-titer Glo Reagent (Promega). Cells were seeded at $0.3 \times 10^6$ cell/mL and treated with increasing concentrations of RP14 as indicated. Cytotoxicity was measured at 24 (blue line), 48 (red line), and 72 (green line) hours and compared to untreated cells. Cell lines H9 (A), and HH (B) were treated.
Figure 10B:
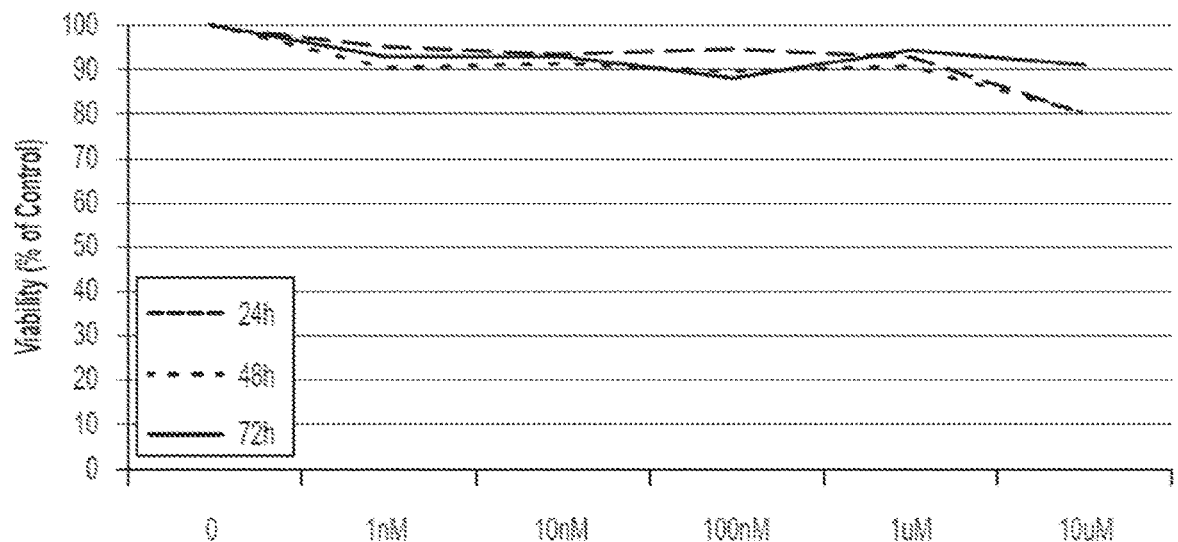
Figure 11A:
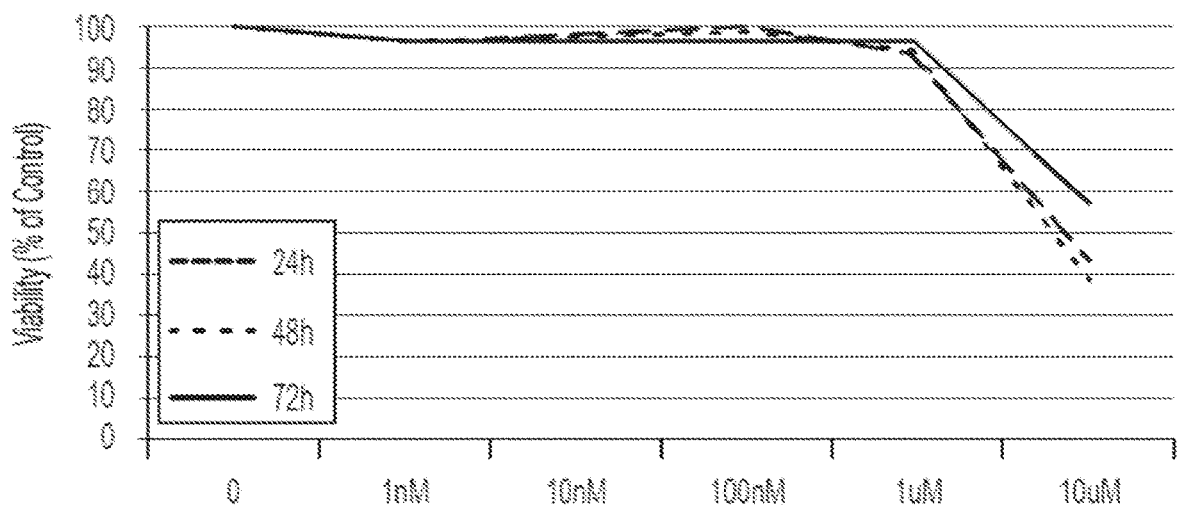
FIGS. 11A-B shows the effect relationship of RP52 for a panel of lymphoma cell lines. Cytotoxicity was evaluated using Cell-titer Glo Reagent (Promega). Cells were seeded at $0.3 \times 10^6$ cell/mL and treated with increasing concentrations of RP52 as indicated. Cytotoxicity was measured at 24 (blue line), 48 (red line), and 72 (green line) hours and compared to untreated cells. Cell lines H9 (A), and HH (B) were treated.
Figure 11B:
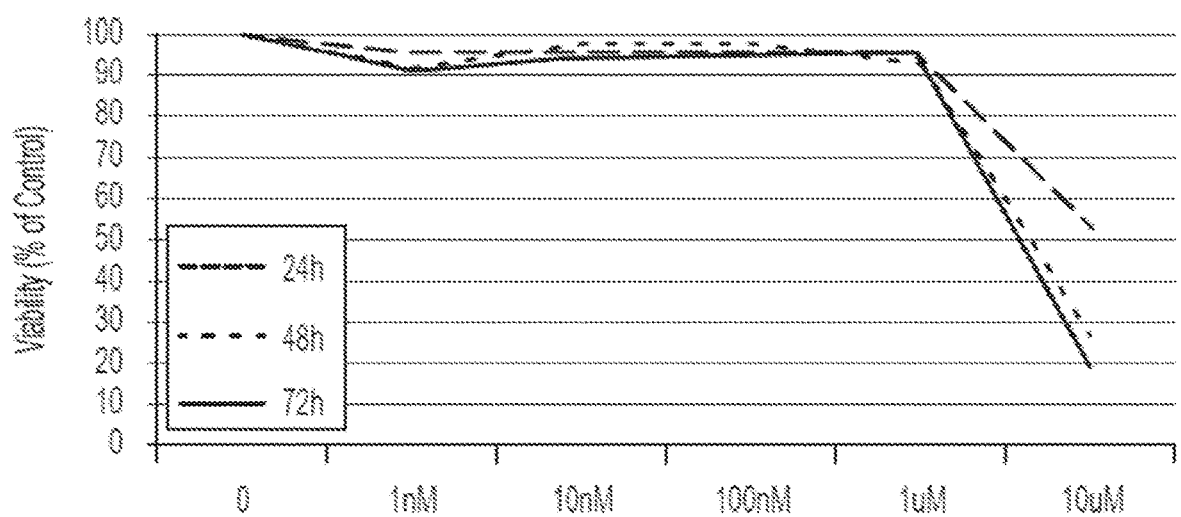
Figure 12A:
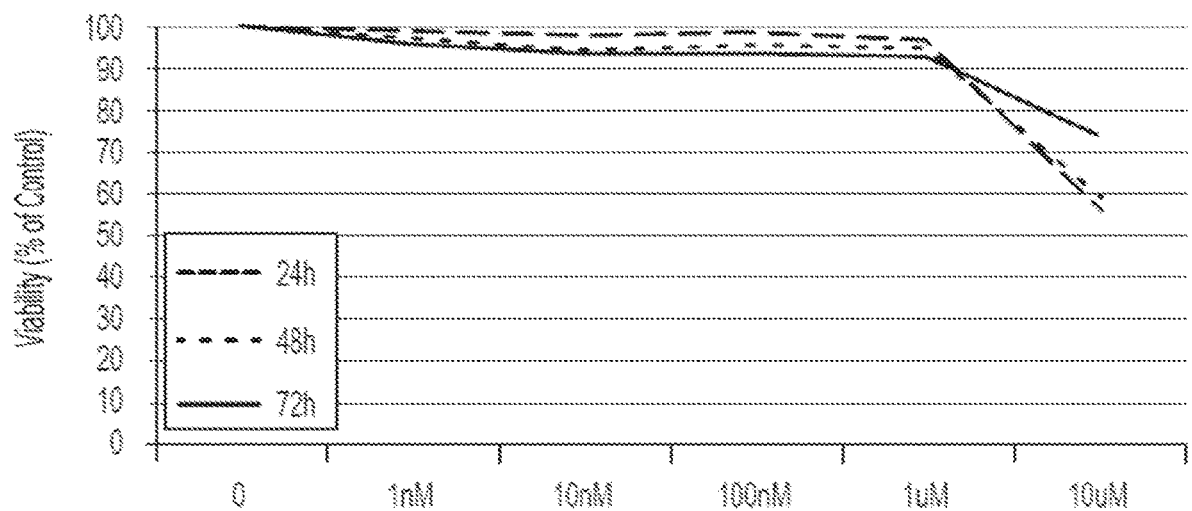
FIGS. 12A-B shows the effect relationship of RP72 for a panel of lymphoma cell lines. Cytotoxicity was evaluated using Cell-titer Glo Reagent (Promega). Cells were seeded at $0.3 \times 10^6$ cell/mL and treated with increasing concentrations of RP72 as indicated. Cytotoxicity was measured at 24 (blue line), 48 (red line), and 72 (green line) hours and compared to untreated cells. Cell lines H9 (A), and HH (B) were treated.
Figure 12B:
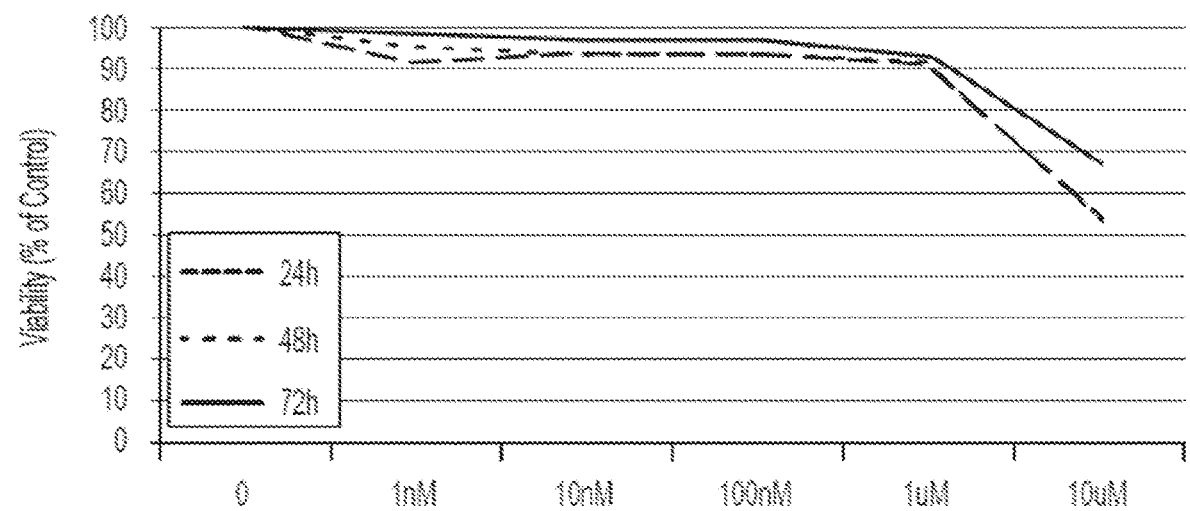
Figure 13A:
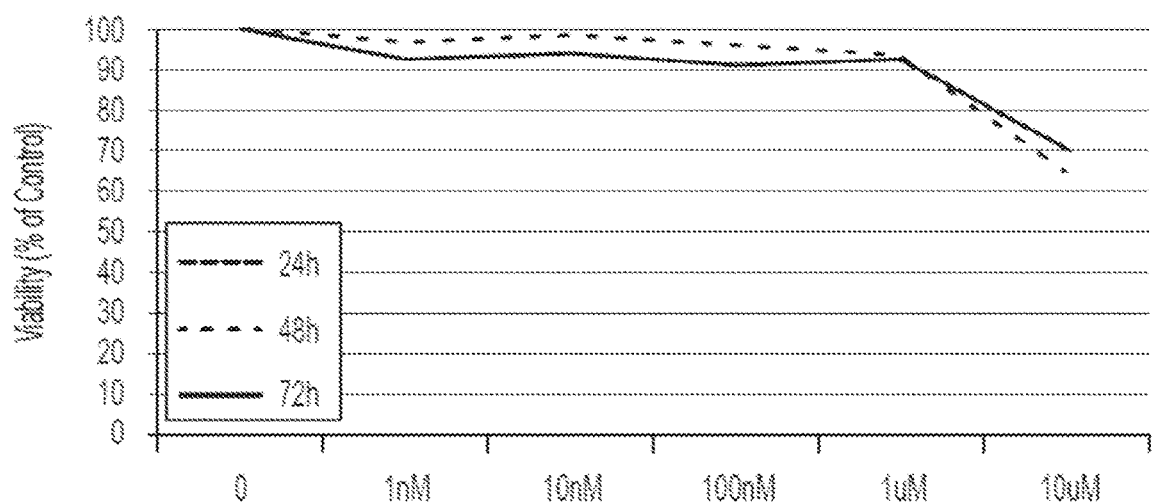
FIGS. 13A-B shows the effect relationship of JF2 for a panel of lymphoma cell lines. Cytotoxicity was evaluated using Cell-titer Glo Reagent (Promega). Cells were seeded at $0.3 \times 10^6$ cell/mL and treated with increasing concentrations of JF2 as indicated. Cytotoxicity was measured at 24 (blue line), 48 (red line), and 72 (green line) hours and compared to untreated cells. Cell lines H9 (A), and HH (B) were treated.
Figure 13B:
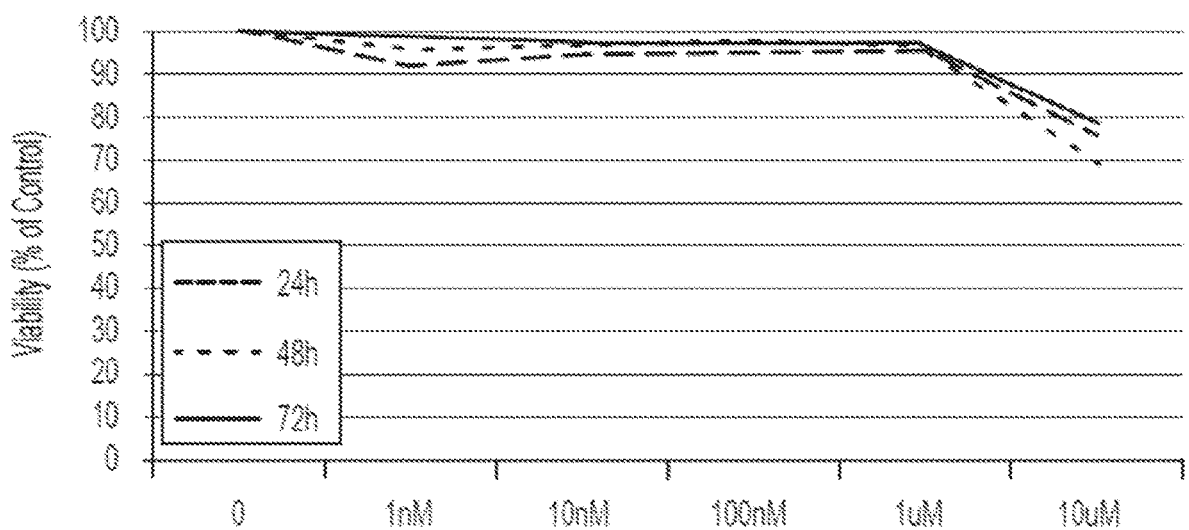
Figures 14A, 14B:
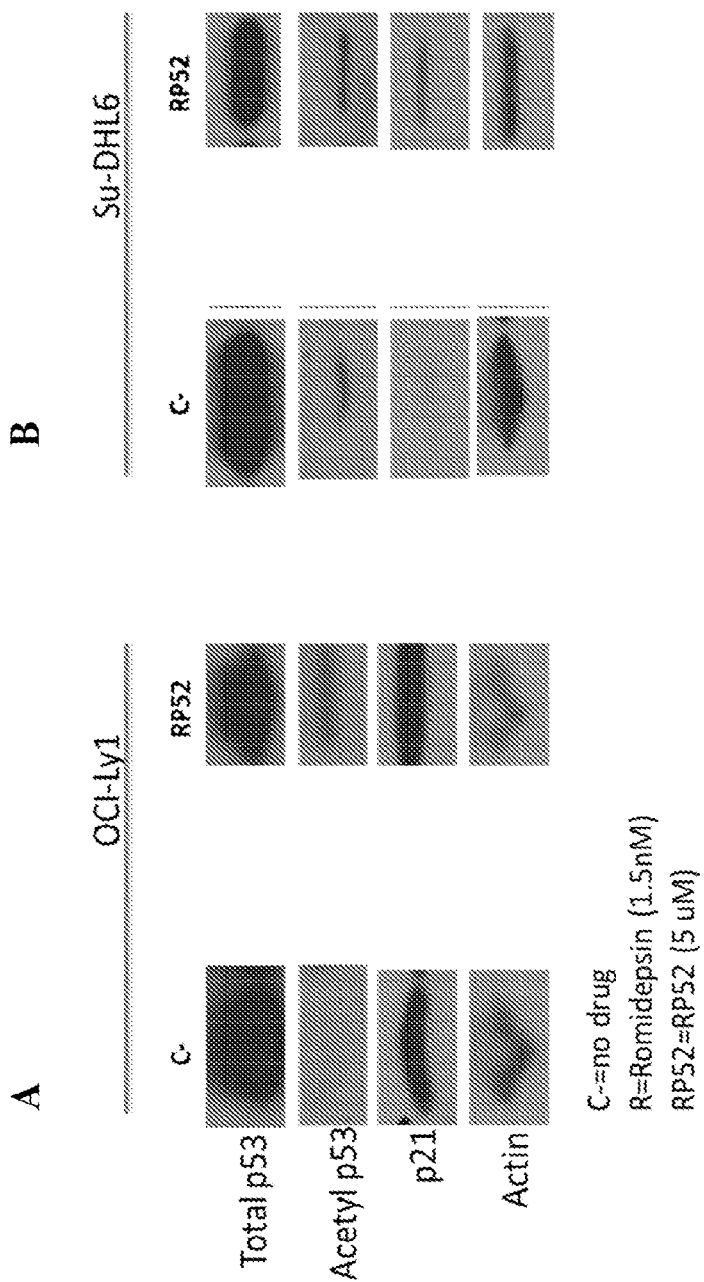
FIGS. 14A-B show acetylation of p53 and modulation of p21 by HAT activator RP52 in diffuse large B-cell lymphoma cell lines Ly1 (A) and Su-DHL6 (B). Cells were treated with Romidepsin 1.5 nM, or RP52 5 uM for 24 hours then lysed with RIPA buffer. Levels of total p53, acetylated p53, and p21 were detected by Western Blot analysis. Antibodies used were anti-acetyl-p53 (Santa Cruz), anti-p53 DO-1 (Abcam), anti-p21 (Cell Signaling).

FIGS. 2A-D shows the effect relationship of RP59 for a panel of lymphoma cell lines. FIGS. 3A-D shows the effect relationship of YF2 for a panel of lymphoma cell lines. FIGS. 4A-D shows the effect relationship of RP23 for a panel of lymphoma cell lines. FIGS. 5A-D shows the effect relationship of RP58 for a panel of lymphoma cell lines. FIGS. 6A-B shows the effect relationship of RP14 for a panel of lymphoma cell lines. FIGS. 7A-B shows the effect relationship of RP72 for a panel of lymphoma cell lines. FIGS. 8A-C shows the effect relationship of RP52 for a panel of lymphoma cell lines. FIGS. 9A-C shows the effect relationship of JF2 for a panel of lymphoma cell lines. FIGS. 10A-B shows the effect relationship of RP14 for a panel of lymphoma cell lines. FIGS. 11A-B shows the effect relationship of RP52 for a panel of lymphoma cell lines. FIGS. 12A-B shows the effect relationship of RP72 for a panel of lymphoma cell lines. FIGS. 13A-B shows the effect relationship of JF2 for a panel of lymphoma cell lines. FIGS. 14A-B show acetylation of p53 and modulation of p21 by HAT activator RP52 in diffuse large B-cell lymphoma cell lines Ly1 (A) and Su-DHL6 (B). Cells were treated with Romidepsin 1.5 nM, or RP52 5 uM for 24 hours then lysed with RIPA buffer. Levels of total p53, acetylated p53, and p21 were detected by Western Blot analysis. Antibodies used were anti-acetyl-p53 (Santa Cruz), anti-p53 DO-1 (Abeam), anti-p21 (Cell Signaling).

Relapsed and refractory T-cell lymphoma continues to be a rare but extraordinarily aggressive disease. HDAC inhibitors are approved for use in peripheral T-cell lymphoma and cutaneous T-cell lymphoma. In addition, diffuse large B-cell lymphoma and follicular lymphomas are the two most common subtypes of lymphoma and harbor heterogenous inactivating mutations in HATs. Without being bound by theory, the effects of these mutations can be mitigated by enhancement of their effect through pharmacologic modification. Treatment with HAT activators in cells with HAT mutations can reverse the malignant phenotype. These mutations can not be modulated by existing HDAC inhibitors.

Histone deacetylase inhibitors have activity on a set of enzymes that remove acetyl groups from histones and transcription factors. Although HAT activators and HDAC inhibitors have converse mechanisms of action, their end result is to enforce acetylation of histones and transcription factors. HAT activators have a converse mechanism of action from known agents with similar effects. They can reverse the malignant genotype of mutated HATs in follicular and diffuse large B-cell lymphomas as well as B-cell derived acute leukemias. These actions would not be possible with HDAC inhibitors alone. HAT activators can be used to overcome inactivating mutations of HATs, which is not possible with any known or existing technology. This invention can enhance HDAC inhibitors activity. They may reverse a malignant phenotype of diffuse large B-cell lymphoma and follicular lymphoma harboring HAT mutations. HAT activators can activate key tumor suppressor proteins such as p53.

The invention described herein can be used to treat inflammatory diseases such as lupus, rheumatoid arthritis, and Sjogren's syndrome, as well as, a host of neurodegenerative diseases including Alzheimer's Disease, Huntington disease, Friederich Ataxia, and others.

Example 11: Selecting HAT Modulators that Rescue LTP in APP/PS1 Mice

Synaptic dysfunction is a major hallmark of AD (*Histol Histopathol,* 1995. 10(2): p. 509-19; herein incorporated by reference in its entirety). An aspect of the drug screening protocol can include a measurement of the effect of compounds onto synaptic function. The APP/PS1 mouse presents an impairment of LTP by the age of 3 months (*Ann Neurol,* 2004. 55(6): p. 801-14; herein incorporated by reference in its entirety), and therefore permits a relatively fast assessment of synaptic function without waiting a long time for mice aging. LTP can be examined because it is a type of synaptic plasticity thought to underlie learning and memory. YF2 can rescue the Aβ-induced reduction of LTP, and other compounds can also be screened to identify those that can re-establish normal LTP. The compounds can be applied for 30 min. Controls can be performed on slices from APP/PS1 mice treated with vehicle, and WT mice treated with compound or vehicle. If the compounds re-establish normal LTP in APP/PS1 slices, one can conclude that the compounds rescue impairment of synaptic plasticity in APP/PS1 mice. Cognitive impairment can also be investigated (see Example 12).

Animals: Tg mice can be obtained by crossing APP (K670M:N671L) with PS1(M146L) (line 6.2) animals. The genotype can be identified by PCR on tail samples (*Nature,* 1996. 383(6602): p. 710-3; *Science,* 1996. 274(5284): p. 99-102; *J Mol Neurosci,* 2002. 19(1-2): p. 135-41; each hereby incorporated by reference in its entirety).

Electrophysiology can be performed on males (see description in *Cell,* 2006. 126(4): p. 775-88; hereby incorporated by reference in its entirety).

Statistical Analyses: see Example 12.

Example 12: Screening for Amelioration of Cognitive Abnormalities in APP/PS1 Mice Treatment with a new HAT modulator indicated by Example 11 will study rescue of cognitive deficits in 3 and 6 month old APP/PS1 mice. As behavioral tasks, the RAWM and contextual FC will be used, two types of tests that assess different types of memory (reference ad associative) that are affected in AD patients. The treatment can be performed with the same timing (i.e. 30 min before training for fear conditioning or before the $1^{st}$ and $2^{nd}$ group of tests for the RAWM). Conditions to be tested can include: APP/PS1 and WT treated with HAT activators, APP/PS1 and WT treated with vehicle. After behavioral testing, mice can be sacrificed and their blood and brains used for Aβ level, Tau protein, TARDBP and TDB levels, and alpha-synuclein measurements. As a control for effectiveness of HAT modulator, hippocampal acetyl-H4 levels can be measured after administration of the compounds 30 min prior to training for fear conditioning and removal of the hippocampi 1 hr after the electric shock (APP/PS1 mice have been shown to have a reduction of acetylated H4 after the electric shock (*J Alzheimers Dis,* 2009. 18(1): p. 131-9; hereby incorporated by reference in its entirety). Further screening can include assays focusing on two areas that have resulted in the withdrawal of many drugs from the market: drug-drug interactions, hERG channel blockage.

Animals: see Example 11.

Behavioral Studies: Experiments can be performed in blind only on male animals to reduce variability. A) Spatial memory. This type of reference memory will be studied with the 2-day RAWM test, as described (*Nat Protoc,* 2006. 1(4): p. 1671-9; hereby incorporated by reference in its entirety). The task is a hybrid of the Morris Water Maze (MWM) and the radial arm land maze. For these experiments, visible platform testing can be conducted to exclude that visual, motor and motivation deficits affect the mouse performance, as described (*Ann Neurol,* 2004. 55(6): p. 801-14; hereby incorporated by reference in its entirety). B) Fear Conditioning to examine both contextual and cued learning will be assessed as described (*J. Clin. Invest.,* 2004. 114: p. 1624-1634; hereby incorporated by reference in its entirety). For these experiments, threshold assessment test can be performed to check sensory perception of electric foot in different groups of mice (*J. Clin. Invest.,* 2004. 114: p. 1624-1634; hereby incorporated by reference in its entirety). In addition, the open-field test can be conducted to evaluate exploratory as described (Neuroscience, 2007. 147(1): p. 28-36; *J Neurosci,* 2008. 28(53): p. 14537-45; each hereby incorporated by reference in its entirety).

Histone acetylation assay: Western blot can be performed from snap-frozen in liquid nitrogen hippocampi. Tissue can be homogenized in RIPA buffer, then sonicated before centrifugation at 10,000 rpm for 5 min. Whole cell extracts can be electrophoresed on 10-20% gradient PAGE gel (Invitrogen) and then immunoblotted. Antibodies can be used at a 1:1,000 concentration for immunoblotting. All anti-histone antibodies can be purchased from Millipore. Immunoblot data can be quantified by measuring the band intensity using imaging software (NIH ImageJ).

Determination of Aβ levels can be performed on homogenates of frozen hemi-brains and plasma as previously described (Ann Neurol, 2004. 55(6): p. 801-14; hereby incorporated by reference in its entirety).

Determination of alpha-synuclein levels can be performed on homogenates of frozen hemi-brains using an α-Synuclein ELISA Kit (Catalog #NS400; Millipore, Billerica, Mass.) according to manufacturer's instructions.

Determination of TARDBP/TDP-43 levels can be performed on homogenates of frozen hemi-brains using a Human TAR DNA binding protein 43, TARDBP/TDP-43 ELISA Kit (Catalog #E1951 h; Wuhan EIAab Science Co, Wuhan, China) according to manufacturer's instructions.

Determination of total Tau and phosphorylated Tau (Thr 231) levels can be performed on homogenates of frozen hemi-brains and plasma using assay and kits according to manufacturer's instructions available from MesoScale Discovery (Gaithersburg, Md.) (see http://www.mesoscalc.com/catalogsystemweb/webroot/products/assays/alzheimers.aspx; hereby incorporated by reference in its entirety).

Statistics: Experiments involving mice can be performed in blind. Results can be expressed as Standard Error Mean (SEM). Level of significance can be set for p<0.05. Results can be analyzed with ANOVA with post-hoc correction with drug or genotype as main effect.

Example 13: Screening for Amelioration of Cognitive Abnormalities in Mouse Models for Huntington's Disease Treatment with a HAT compound to assess whether the compound can rescue the cognitive deficits in a mouse model of Huntington's Disease (e.g., FVB-Tg(YAC128) 53Hay/J and FVB/NJ-Tg(YAC72)2511Hay/J mice, available from the Jackson Laboratory, Bar Harbor Me.) can be examined. As behavioral tasks, the RAWM and contextual FC can be employed, two types of tests assessing different types of memory (reference ad associative). The treatment can be performed with the same timing (i.e. 30 min before training for fear conditioning or before the $1^{st}$ and $2^{nd}$ group of tests for the RAWM). Conditions to be tested can include: Huntington's Disease mice and WT treated with HAT modulator, Huntington's Disease mice and WT treated with vehicle. After behavioral testing mice can be sacrificed and their blood and brains used for Huntingtin protein level measurement. As a control for effectiveness of HAT modulation, hippocampal acetyl-H4 levels can be measured after administration of the compounds 30 min prior to training for fear conditioning and removal of the hippocampi 1 hr after the electric shock. Assays focusing on two areas that have resulted in the withdrawal of many drugs from the market can also be employed: drug-drug interactions, hERG channel blockage.

Animals: Mouse models of Huntington's Disease (e.g., FVB-Tg(YAC128)53Hay/J [Stock no. 004938] and FVB/NJ-Tg(YAC72)2511Hay/J mice [Stock no. 003640]) can be obtained from the Jackson Laboratory (Bar Harbor Me.). See also, Hodgson et al., (May 1999) Neuron, Vol. 23, 181-192; hereby incorporated by reference in its entirety.

Behavioral Studies: Experiments can be performed in blind only on male animals to reduce variability. A) Spatial memory. This type of reference memory can be studied with the 2-day RAWM test, as described (Nat Protoc, 2006. 1(4): p. 1671-9; hereby incorporated by reference in its entirety). The task is a hybrid of the Morris Water Maze (MWM) and the radial arm land maze. For these experiments, visible platform testing can be conducted to exclude that visual, motor and motivation deficits affect the mouse performance, as described (Ann Neurol, 2004. 55(6): p. 801-14; hereby incorporated by reference in its entirety). B) Fear Conditioning to examine both contextual and cued learning can be assessed as described (J. Clin. Invest., 2004. 114: p. 1624-1634; hereby incorporated by reference in its entirety). For these experiments, threshold assessment test can performed to check sensory perception of electric foot in different groups of mice (J. Clin. Invest., 2004. 114: p. 1624-1634; hereby incorporated by reference in its entirety). In addition, the open-field test can be conducted to evaluate exploratory as described (Neuroscience, 2007. 147(1): p. 28-36; J Neurosci, 2008. 28(53): p. 14537-45; each hereby incorporated by reference in its entirety).

Histone acctylation assay: Western blot can be performed from snap-frozen in liquid nitrogen hippocampi. Tissue can be homogenized in RIPA buffer, then sonicated before centrifugation at 10,000 rpm for 5 min. Whole cell extracts can be electrophoresed on 10-20% gradient PAGE gel (Invitrogen) and then immunoblotted. Antibodies can be used at a 1:1,000 concentration for immunoblotting. All anti-histone antibodies can be purchased from Millipore. Immunoblot data can be quantified by measuring the band intensity using imaging software (NIH ImageJ).

Determination of huntingtin levels can be performed on homogenates of frozen hemi-brains and plasma using a Huntingtin (Htt) ELISA Kit (Catalog #ABIN423526; Antibodies-online, Atlanta, Ga.) according to manufacturer's instructions.

Statistics: Experiments on mice can be performed in blind. Results can be expressed as Standard Error Mean (SEM). Level of significance can be set for p<0.05. Results can be analyzed with ANOVA with post-hoc correction with drug or genotype as main effect.

Example 14: Screening for Amelioration of Cognitive Abnormalities in Mouse Models for Parkinson's Disease Parkinson's Disease (PD) is a degenerative disease with a neuronal death up to 75-95% of the dopamine neurons in the substantia nigra nucleus. Treatment with a HAT modulator compound indicated by Example 11 to assess rescue of abnormal motor movements in a mouse model of PD (e.g., see Parkinson's Disease mice models available from the Jackson Laboratory, Bar Harbor Me. at http://jaxmice.jax-.org/list/ra1594.html; see also Emborg, Journal of Neuroscience Methods 139 (2004) 121-143; Lane, Psychopharmacology (2008) 199:303-312; and Meredith et al., Acta Neuropathol (2008) 115:385-398; each hereby incorporated by reference in its entirety) can be assessed. Behavioral tasks, for example, dyskinesia, bradykinesia, tremor, and/or grip force for the evaluation of the compound's efficacy, can be examined at various stages of PD. Conditions to be tested can include: PD mice and WT treated with HAT modulator, PD mice and WT treated with vehicle. After behavioral evaluation, mice can be sacrificed and their brains used for aggregated alpha-synuclein protein measurement. As a control for effectiveness of HAT modulation, hippocampal acetyl-H4 levels can be measured.

Animals: Mouse models of Parkinson's Disease can be obtained from the Jackson Laboratory (Bar Harbor Me.). See also, Meredith et al., *Acta Neuropathol* (2008) 115:385-398; hereby incorporated by reference in its entirety).

Behavioral Studies: Experiments can be performed in blind only on male animals to reduce variability, according to methods described by Fleming et al., ((2004) The Journal of Neuroscience, 24(42):9434-9440) and Hwang et al., ((2005) The Journal of Neuroscience, 25(8):2132-2137; each hereby incorporated by reference in its entirety).

Histone acctylation assay: Western blot can be performed from snap-frozen in liquid nitrogen hippocampi. Tissue can be homogenized in RIPA buffer, then sonicated before centrifugation at 10,000 rpm for 5 min. Whole cell extracts can be electrophoresed on 10-20% gradient PAGE gel (Invitrogen) and then immunoblotted. Antibodies can be used at a 1:1,000 concentration for immunoblotting. All anti-histone antibodies can be purchased from Millipore. Immunoblot data can be quantified by measuring the band intensity using imaging software (NIH ImageJ).

Determination of alpha-synuclein levels can be performed on homogenates of frozen hemi-brains using an α-Synuclein ELISA Kit (Catalog #NS400; Millipore, Billerica, Mass.) according to manufacturer's instructions or via standard neuropathological methods (brain tissue histology).

Statistics: Experiments in mice can be performed in blind. Results can be expressed as Standard Error Mean (SEM). Level of significance can be set for p<0.05. Results can be analyzed with ANOVA with post-hoc correction with drug or genotype as main effect.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A compound of formula (I):

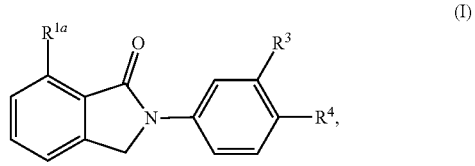

or a pharmaceutically acceptable salt or solvate thereof, wherein $R^{1a}$ is OH;
$R^3$ is halogen or $C_1$-$C_2$-haloalkyl; and
$R^4$ is halogen or $C_1$-$C_2$-haloalkyl.

2. A compound having the structure:

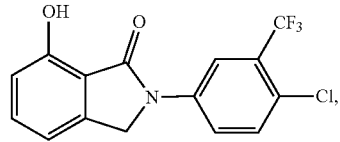 [SMILES: O=C1c2c(O)cccc2CN1c1ccc(Cl)c(C(F)(F)F)c1]

or a pharmaceutically acceptable salt thereof.

3. A pharmaceutical composition comprising a compound according to claim 1, or a pharmaceutically acceptable salt or solvate thereof; and a pharmaceutically acceptable carrier.

4. A pharmaceutical composition comprising a compound according to claim 2, or a pharmaceutically acceptable salt or solvate thereof; and a pharmaceutically acceptable carrier.

* * * * *